(12) United States Patent
Zhang

(10) Patent No.: US 10,722,479 B2
(45) Date of Patent: Jul. 28, 2020

(54) DIMETHOXYPHENYL INHIBITORS OF VESICULAR MONOAMINE TRANSPORTER 2

(71) Applicant: AUSPEX PHARMACEUTICALS, INC., La Jolla, CA (US)

(72) Inventor: Chengzhi Zhang, La Jolla, CA (US)

(73) Assignee: AUSPEX PHARMACEUTICALS, INC., North Wales, PA (US)

( * ) Notice: Subject to any disclaimer, the term of this patent is extended or adjusted under 35 U.S.C. 154(b) by 0 days.

(21) Appl. No.: 15/550,152

(22) PCT Filed: Feb. 17, 2016

(86) PCT No.: PCT/US2016/018222
§ 371 (c)(1),
(2) Date: Aug. 10, 2017

(87) PCT Pub. No.: WO2016/133989
PCT Pub. Date: Aug. 25, 2016

(65) Prior Publication Data
US 2018/0036260 A1    Feb. 8, 2018

Related U.S. Application Data

(60) Provisional application No. 62/117,654, filed on Feb. 18, 2015.

(51) Int. Cl.
*A61K 31/137*    (2006.01)
*A61K 31/138*    (2006.01)
*A61K 31/4375*   (2006.01)
*C07C 217/60*    (2006.01)
*C07B 59/00*     (2006.01)

(52) U.S. Cl.
CPC .......... *A61K 31/137* (2013.01); *A61K 31/138* (2013.01); *A61K 31/4375* (2013.01); *C07B 59/001* (2013.01); *C07C 217/60* (2013.01); *C07B 2200/05* (2013.01)

(58) Field of Classification Search
CPC ................ A61K 31/137; A61K 31/138; A61K 31/4375; C07C 217/60; C07B 2200/05
USPC ........................................................ 564/336
See application file for complete search history.

(56) References Cited

U.S. PATENT DOCUMENTS

2010/0130480 A1*  5/2010  Gant .................... C07D 455/06
                                                       514/220
2010/0143287 A1   6/2010  Gant
2015/0004231 A1   1/2015  Sommer et al.

FOREIGN PATENT DOCUMENTS

EP         0165682 A1    12/1985
WO         2008/122010 A1  10/2008
WO         WO2014202646    * 12/2014

OTHER PUBLICATIONS

Latts, J.R., "Clinical Pharmacokinetics and Metabolism of Bevantolol, Angiology—Journal of Vascular Diseases," Mar. 1986, pp. 221-225. (Year: 1986).*
Erickson et al. "Reserpine- and tetrabenazine-sensitive transport of 3H-histamine by the neuronal isoform of the vesicular monoamine transporter", Journal of Molecular Neuroscience, 1995, 6(4), 277-287.
Fishman et al., "Bevantolol. A preliminary review of its pharmacodynamics and pharmacokinetic properties, and therapeutic efficacy in hypertension and angina pectoris", Drugs, 1988, 35, 1-21.
Kaplan, "Pharmacology of bevantolol hydrochloride", Am J Cardio, 1986 58(12), 3E-7E.
Kilbourn et al., Synapse, In Vivo Measures of Dopaminergic Radioligands in the Rat Brain: Equilibrium Infusion Studies 2002, 43(3), 188-194.
Ko et al., "In vitro inhibition of the cytochrome P450 (CYP450) system by the antiplatelet drug ticlopidine: potent effect on CYP2C19 and CYP2D6", British Journal of Clinical Pharmacology, 2000, 49, 343-351.
Omura et al., "Ca(2+)-antagonistic action of bevantolol on hypothalamic neurons in vitro: its comparison with those of other beta-adrenoreceptor antagonists, a local anesthetic and a Ca(2+)-antagonist", Brain Res. 1996, 706, 289-292.
Scherman et al., Journal of Neurochemistry, [3H] Dihydrotetrabenazine, a New In Vitro Monoaminergic Probe for Human Brain 1988, 50(4), 1131-1136.
Uebelhack et al., :Inhibition of Platelet MAO-B by Kava Pyrone-Enriched Extract from *Piper methysticum* Forger (Kava-Kava), Pharmacopsychiatry, 1998, 31, 187-192.
Weyler et al., J. Biol Chem., Purification and Properties of Monoamine Oxidase Type A from Human Placenta, 1985, 260, 13199-13207.
Williams, "Bevantolol: a beta-1 adrenoreceptor antagonist with unique additional actions", J. Clin. Pharmacol. 1987, 27, 450-460.

* cited by examiner

*Primary Examiner* — Ana Z Muresan
(74) *Attorney, Agent, or Firm* — BakerHostetler

(57) ABSTRACT

Described are dimethoxyphenyl inhibitors of VMAT2, pharmaceutical compositions thereof, and methods of use thereof.

30 Claims, No Drawings

DIMETHOXYPHENYL INHIBITORS OF VESICULAR MONOAMINE TRANSPORTER 2

CROSS-REFERENCE TO RELATED APPLICATIONS

This application is a National Stage Application filed under 35 U.S.C. 371 of International Application No. PCT/US2016/018222, filed Feb. 17, 2016, which claims the benefit of priority of U.S. provisional Application No. 62/117,654 filed Feb. 18, 2015, the disclosure of which is hereby incorporated by reference, as if written herein, in its entirety.

TECHNICAL FIELD

Disclosed herein are new dimethoxyphenyl compounds and compositions and their application as pharmaceuticals for the treatment of disorders. Methods of inhibiting vesicular monoamine transporter 2 (VMAT2) activity in a subject are also provided for the treatment of disorders such as chronic hyperkinetic movement disorders, Tourette's syndrome, Parkinson's disease, Huntington's disease, Huntington's chorea, Sydenham's chorea, tardive dyskinesia/dystonia, Parkinson's disease levodopa-induced dyskinesia, levodopa-induced dyskinesia, ataxia, corticobasal degeneration, dyskinesias (paroxysmal), dystonia (general, segmental, focal) including blepharospasm, spasmodic torticollis (cervical dystonia), writer's cramp (limb dystonia), laryngeal dystonia (spasmodic dysphonia), and oromandibular dystonia, essential tremor, hereditary spastic paraplegia, multiple system atrophy (Shy Drager Syndrome), myoclonus, progressive supranuclear palsy, restless legs syndrome, Rett Syndrome, spasticity due to stroke, cerebral palsy, multiple sclerosis, spinal cord or brain injury, tics, Wilson's Disease, oppositional defiant disorder, Huntington's disease like diseases (HDL1, HDL2 and HDL3), benign hereditary chorea, neuroacanthocytosis, neurodegeneration with brain iron accumulation (NBIA), athetosis, Friedreich ataxia, spinocerebellar ataxia, multiple system atrophy, dentatorubral-pallidoluysian atrophy, ataxia with oculomotor apraxia (types 1 and 2), ataxia telangiectasia, focal dystonias, idiopathic dystonias such as Oppenheim dystonia and torticollis, dystonia-plus syndromes, secondary dystonias, Duchenne muscular dystrophy, and Down syndrome. Methods of antagonism of beta-1 adrenoreceptor activity and calcium channel blocking in a subject are also provided for the treatment or prevention of disorders such as cardiac infarction, angina pectoris, atrial fibrillation, cardiac arrhythmia, congestive heart failure, hypertrophic obstructive cardiomyopathy, essential tremor, glaucoma, hypertension, migraine (prophylaxis), mitral valve prolapse, myocardial infarction, pheochromocytoma, postural orthostatic tachycardia syndrome, anxiety, hyperhidrosis, and hyperthyroidism.

BACKGROUND

Bevantolol ((±)-bevantolol; DL-bevantolol; NSC 132348; 1-[[2-(3,4-dimethoxyphenyl)ethyl]amino]-3-(3-methylphenoxy)-2-propanol; CAS #59170-23-9) is a vesicular monoamine transporter 2 (VMAT2) inhibitor. Bevantolol has shown promise in treating chronic hyperkinetic movement disorders, Tourette's syndrome, Parkinson's disease, Huntington's disease, Huntington's chorea, Sydenham's chorea, tardive dyskinesia/dystonia, Parkinson's disease levodopa-induced dyskinesia, levodopa-induced dyskinesia, ataxia, corticobasal degeneration, dyskinesias (paroxysmal), dystonia (general, segmental, focal) including blepharospasm, spasmodic torticollis (cervical dystonia), writer's cramp (limb dystonia), laryngeal dystonia (spasmodic dysphonia), and oromandibular dystonia, essential tremor, hereditary spastic paraplegia, multiple system atrophy (Shy Drager Syndrome), myoclonus, progressive supranuclear palsy, restless legs syndrome, Rett Syndrome, spasticity due to stroke, cerebral palsy, multiple sclerosis, spinal cord or brain injury, tics, Wilson's Disease, oppositional defiant disorder, Huntington's disease like diseases (HDL1, HDL2 and HDL3), benign hereditary chorea, neuroacanthocytosis, neurodegeneration with brain iron accumulation (NBIA), athetosis, Friedreich ataxia, spinocerebellar ataxia, multiple system atrophy, dentatorubral-pallidoluysian atrophy, ataxia with oculomotor apraxia (types 1 and 2), ataxia telangiectasia, focal dystonias, idiopathic dystonias such as Oppenheim dystonia and torticollis, dystonia-plus syndromes, secondary dystonias, Duchenne muscular dystrophy, and Down syndrome. WO 2014202646.

Bevantolol is also known as a beta-1 adrenoreceptor antagonist (Vaughan Williams, "Bevantolol: a beta-1 adrenoreceptor antagonist with unique additional actions", J. Clin. Pharmacol. 1987, 27, 450-460) and calcium channel blocker (T. Omura, T. Kobayashi, K. Nishioka, N. Miyake, N. Akaike, "Ca(2+)-antagonistic action of bevantolol on hypothalamic neurons in vitro: its comparison with those of other beta-adrenoreceptor antagonists, a local anesthetic and a Ca(2+)-antagonist", Brain Res. 1996, 706, 289-292). By virtue of these actions bevantolol is useful for the treatment of hypertension and angina pectoris. (W. H. Fishman, R. J. Goldberg, P. Benfield, "Bevantolol. A preliminary review of its pharmacodynamics and pharmacokinetic properties, and therapeutic efficacy in hypertension and angina pectoris", Drugs, 1988, 35, 1-21; H. Kaplan, "Pharmacology of bevantolol hydrochloride", Am. J. Cardiol. 1986, 58, E3-E7.) It is approved for example in the US, Great Britain, France and Japan for the treatment of hypertension and angina pectoris from coronary heart disease.

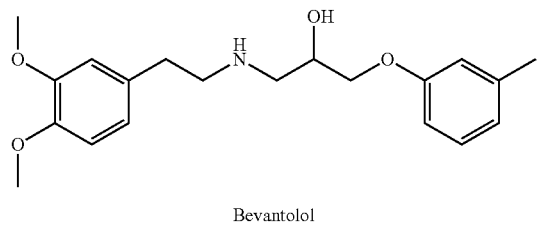 [SMILES: COc1ccc(CCNCC(O)COc2cccc(C)c2)cc1OC]

Bevantolol

Bevantolol is subject to extensive $CYP_{450}$-mediated oxidative metabolism, including hydroxylation of the methyl-bearing phenyl ring, hydroxylation of the aromatic methyl group, followed by further oxidation to the carboxylic acid, and oxidative demethylation of the methoxy groups. Kaplan et al., New Drugs Annual: Cardiovascular Drugs, 1985, Vol. 3. Latts, J. R., Clinical Pharmacokinetics and Metabolism of Bevantolol, *Angiology—Journal of Vascular Diseases*, March 1986, p. 221-225.

Deuterium Isotope Effect

In order to eliminate foreign substances such as therapeutic agents, the animal body expresses various enzymes, such as the cytochrome $P_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) □-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-Eact/RT}$. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1H$), a C-D bond is stronger than the corresponding C—$^1H$ bond. If a C—$^1H$ bond is broken during a rate-determining step in a chemical reaction (i.e. the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C—$^1H$ bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects.

Deuterium ($^2H$ or D) is a stable and non-radioactive isotope of hydrogen which has approximately twice the mass of protium ($^1H$), the most common isotope of hydrogen. Deuterium oxide ($D_2O$ or "heavy water") looks and tastes like $H_2O$, but has different physical properties.

When pure $D_2O$ is given to rodents, it is readily absorbed. The quantity of deuterium required to induce toxicity is extremely high. When about 0-15% of the body water has been replaced by $D_2O$, animals are healthy but are unable to gain weight as fast as the control (untreated) group. When about 15-20% of the body water has been replaced with $D_2O$, the animals become excitable. When about 20-25% of the body water has been replaced with $D_2O$, the animals become so excitable that they go into frequent convulsions when stimulated. Skin lesions, ulcers on the paws and muzzles, and necrosis of the tails appear. The animals also become very aggressive. When about 30% of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method may not be applicable to all drug classes. For example, deuterium incorporation can lead to metabolic switching. Metabolic switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

Bevantolol is a vesicular monoamine transporter 2 (VMAT2) inhibitor. The carbon-hydrogen bonds of bevantolol contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation may produce a detectable Deuterium Kinetic Isotope Effect (DKIE) that could affect the pharmacokinetic, pharmacologic and/or toxicologic profiles of such bevantolol in comparison with the compound having naturally occurring levels of deuterium.

Based on discoveries made in our laboratory, as well as considering the literature, bevantolol is likely metabolized in humans at the aromatic methyl and methoxy groups, the methyl-bearing phenyl ring, the benzylic methylene group, the N-methylene groups, the O-methylene group, and the O-methine group. The current approach has the potential to prevent metabolism at these sites. Other sites on the molecule may also undergo transformations leading to metabolites with as-yet-unknown pharmacology/toxicology. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the strong potential to slow the metabolism of bevantolol and attenuate interpatient variability.

Novel compounds and pharmaceutical compositions, certain of which have been found to block calcium channel or beta adrenoreceptor activity, and/or to inhibit VMAT2 have been discovered, together with methods of synthesizing and using the compounds, including methods for the treatment of disorders in a patient by administering the compounds.

DETAILED DESCRIPTION

In certain embodiments of the present invention, compounds have structural Formula I:

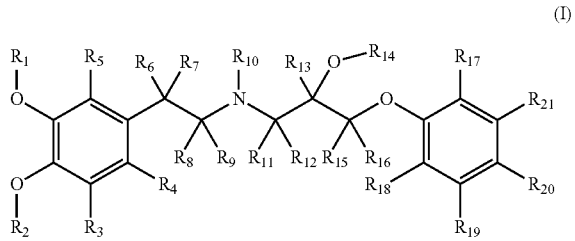

(I)

or a salt thereof, wherein:

$R_1$-$R_2$ and $R_{21}$ are independently selected from the group consisting of —$CH_3$, —$CH_2D$; —$CD_2H$, and —$CD_3$;

$R_3$-$R_{20}$ are independently selected from the group consisting of hydrogen and deuterium; and at least one of $R_1$-$R_{21}$ is deuterium or contains deuterium.

In certain embodiments, $R_{10}$ and $R_{14}$ are hydrogen.
In certain embodiments, $R_1$ is $CD_3$.
In certain embodiments, $R_2$ is $CD_3$.
In certain embodiments, $R_1$ is $CD_3$ and $R_2$ is $CD_3$.
In certain embodiments, $R_{21}$ is $CD_3$.
In certain embodiments, one of $R_1$ and $R_2$ is $CD_3$ and $R_{21}$ is $CD_3$.
In certain embodiments, $R_1$ is $CD_3$, $R_2$ is $CD_3$, and $R_{21}$ is $CD_3$.
In certain embodiments, $R_6$ and $R_7$ are deuterium.
In certain embodiments, $R_8$ and $R_9$ are deuterium.
In certain embodiments, $R_6$-$R_9$ are deuterium.
In certain embodiments, $R_{11}$ and $R_{12}$ are deuterium.
In certain embodiments, $R_{13}$ is deuterium.
In certain embodiments, $R_{15}$ and $R_{16}$ are deuterium.
In certain embodiments, $R_{11}$, $R_{12}$, $R_{15}$, and $R_{16}$ are deuterium.
In certain embodiments, $R_{11}$, $R_{12}$, $R_{13}$, $R_{15}$, and $R_{16}$ are deuterium.
In certain embodiments, $R_6$-$R_9$, $R_{11-13}$, and $R_{15}$, and $R_{16}$ are deuterium.
In certain embodiments, $R_{11}$, $R_{12}$, $R_{15}$, and $R_{16}$ are deuterium, $R_1$ is $CD_3$ and $R_2$ is $CD_3$.
In certain embodiments, $R_{11}$, $R_{12}$, $R_{13}$, $R_{15}$, and $R_{16}$ are deuterium, $R_1$ is $CD_3$, and $R_2$ is $CD_3$.
In certain embodiments, $R_{11}$, $R_{12}$, $R_{13}$, $R_{15}$, and $R_{16}$ are deuterium and $R_{21}$ is $CD_3$.
In certain embodiments, $R_{11}$, $R_{12}$, $R_{13}$, $R_{15}$, and $R_{16}$ are deuterium, $R_1$ is $CD_3$, $R_2$ is $CD_3$, and $R_{21}$ is $CD_3$.
In certain embodiments, $R_6$-$R_9$ are deuterium, $R_1$ is $CD_3$ and $R_2$ is $CD_3$.
In certain embodiments, $R_6$-$R_9$ are deuterium, $R_1$ is $CD_3$, $R_2$ is $CD_3$, and $R_{21}$ is $CD_3$.
In certain embodiments, $R_6$-$R_9$, $R_{11-13}$, and $R_{15}$, and $R_{16}$ are deuterium, $R_1$ is $CD_3$ and $R_2$ is $CD_3$.
In certain embodiments, $R_6$-$R_9$, $R_{11-13}$, and $R_{15}$, and $R_{16}$ are deuterium and $R_{21}$ is $CD_3$.
In certain embodiments, $R_6$-$R_9$, $R_{11-13}$, and $R_{15}$, and $R_{16}$ are deuterium, $R_1$ is $CD_3$, $R_2$ is $CD_3$, and $R_{21}$ is $CD_3$.

Also provided herein are embodiments according to each of the embodiments above, wherein:

every other substituent among $R_3$-$R_{20}$ not specified as deuterium is hydrogen; and if any one or more of $R_1$-$R_2$ and $R_{21}$ is not specified to be —$CD_3$, then it is (they are) —$CH_3$.

In certain embodiments, at least one of $R_1$-$R_{21}$ independently has deuterium enrichment of no less than about 1%.
In certain embodiments, at least one of $R_1$-$R_{21}$ independently has deuterium enrichment of no less than about 10%.
In certain embodiments, at least one of $R_1$-$R_{21}$ independently has deuterium enrichment of no less than about 50%.
In certain embodiments, at least one of $R_1$-$R_{21}$ independently has deuterium enrichment of no less than about 90%.
In certain embodiments, at least one of $R_1$-$R_{21}$ independently has deuterium enrichment of no less than about 98%.

Certain compounds disclosed herein may possess useful VMAT2 inhibiting activity, and may be used in the treatment or prophylaxis of a disorder in which VMAT2 plays an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for inhibiting VMAT2. Other embodiments provide methods for treating a VMAT2-mediated disorder in a patient in need of such treatment, comprising administering to the patient a therapeutically effective amount of a compound or composition according to the present invention. Also provided is the use of certain compounds disclosed herein for use in the manufacture of a medicament for the prevention or treatment of a disorder ameliorated by the inhibition of VMAT2.

Certain compounds disclosed herein may possess useful beta-1 adreneoreceptor antagonist activity, and may possess in addition calcium channel blocker activity, and may be used in the treatment of cardiovascular disorders in which beta-1 adreneoreceptor antagonist activity and/or calcium channel blocker activity is useful. Certain embodiments provide methods for antagonizing beta-1 adrenoreceptors, and/or calcium channel blocking. Other embodiments provide methods for treating cardiovascular disorders in a patient in need of such treatment, comprising administering to said patient a therapeutically effective amount of a compound according to the present invention. In some embodiments, the cardiovascular disorder is hypertension or angina pectoris. Also provided is the use of certain compounds disclosed herein for use in the manufacture of a medicament for the treatment of a cardiovascular disorder ameliorated by beta-1 adrenoreceptor antagonism or calcium channel blockade.

In certain embodiments of the present invention, compounds have structural Formula II:

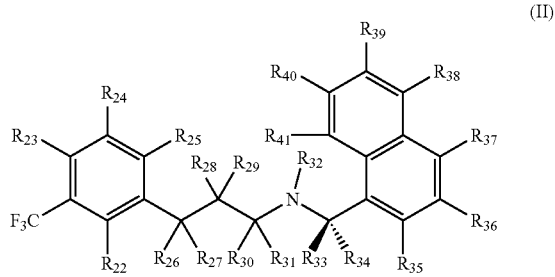

(II)

or a salt thereof, wherein:

$R_{22}$-$R_{32}$ and $R_{34}$-$R_{41}$ are independently selected from the group consisting of hydrogen and deuterium;

$R_{33}$ is selected from the group consisting of —CH$_3$, —CH$_2$D; —CD$_2$H, and —CD$_3$; and at least one of $R_{22}$-$R_{41}$ is deuterium or contains deuterium.

In certain embodiments of the present invention, compounds have structural Formula III:

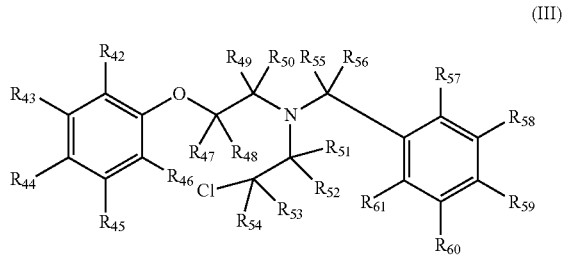

(III)

or a salt thereof, wherein:

$R_{42}$-$R_{49}$ and $R_{51}$-$R_{61}$ are independently selected from the group consisting of hydrogen and deuterium;

$R_{50}$ is selected from the group consisting of —CH$_3$, —CH$_2$D; —CD$_2$H, and —CD$_3$; and at least one of $R_{42}$-$R_{61}$ is deuterium or contains deuterium.

The compounds as disclosed herein may also contain less prevalent isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen.

In certain embodiments, the compound disclosed herein may expose a patient to a maximum of about 0.000005% D$_2$O or about 0.00001% DHO, assuming that all of the C-D bonds in the compound as disclosed herein are metabolized and released as D$_2$O or DHO. In certain embodiments, the levels of D$_2$O shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of D$_2$O or DHO upon drug metabolism.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Also provided is a compound chosen from the Examples and compounds disclosed herein.

In certain embodiments are provided compounds as disclosed herein wherein each position represented as D has deuterium enrichment of no less than about 1%. In certain embodiments are provided compounds as disclosed herein wherein each position represented as D has deuterium enrichment of no less than about 10%. In certain embodiments are provided compounds as disclosed herein wherein each position represented as D has deuterium enrichment of no less than about 50%. In certain embodiments are provided compounds as disclosed herein wherein each position represented as D has deuterium enrichment of no less than about 90%. In certain embodiments are provided compounds as disclosed herein wherein each position represented as D has deuterium enrichment of no less than about 95%. In certain embodiments are provided compounds as disclosed herein wherein each position represented as D has deuterium enrichment of no less than about 98%.

Also provided is a pharmaceutical composition comprising a compound as disclosed herein together with a pharmaceutically acceptable carrier.

Also provided is a method of treatment of a VMAT2-mediated disorder comprising the administration of a therapeutically effective amount of a compound as disclosed herein to a patient in need thereof. Also provided is the corresponding use of a compound as disclosed herein in treatment of disease. Also provided is the corresponding use of a compound as disclosed herein in the treatment of a VMAT2-mediated disorder. Also provided is the corresponding use of a compound as disclosed herein in the manufacture of a medicament for the treatment of a disease, for example a VMAT2-mediated disorder.

In certain embodiments, the disorder is selected from the group consisting of chronic hyperkinetic movement disorders, Tourette's syndrome, Parkinson's disease, Huntington's disease, Huntington's chorea, Sydenham's chorea, tardive dyskinesia/dystonia, Parkinson's disease levodopa-induced dyskinesia, levodopa-induced dyskinesia, ataxia, corticobasal degeneration, dyskinesias (paroxysmal), dystonia (general, segmental, focal) including blepharospasm, spasmodic torticollis (cervical dystonia), writer's cramp (limb dystonia), laryngeal dystonia (spasmodic dysphonia), and oromandibular dystonia, essential tremor, hereditary spastic paraplegia, multiple system atrophy (Shy Drager Syndrome), myoclonus, progressive supranuclear palsy, restless legs syndrome, Rett Syndrome, spasticity due to stroke, cerebral palsy, multiple sclerosis, spinal cord or brain injury, tics, Wilson's Disease, oppositional defiant disorder, Huntington's disease like diseases (HDL1, HDL2 and HDL3), benign hereditary chorea, neuroacanthocytosis, neurodegeneration with brain iron accumulation (NBIA), athetosis, Friedreich ataxia, spinocerebellar ataxia, multiple system atrophy, dentatorubral-pallidoluysian atrophy, ataxia with oculomotor apraxia (types 1 and 2), ataxia telangiectasia, focal dystonias, idiopathic dystonias such as Oppenheim dystonia and torticollis, dystonia-plus syndromes, secondary dystonias, Duchenne muscular dystrophy, and Down syndrome.

Also provided is a method of treatment of a beta-1 adrenoreceptor and/or calcium channel-mediated disorder comprising the administration of a therapeutically effective amount of a compound as disclosed herein to a patient in need thereof. Also provided is the corresponding use of a compound as disclosed herein in treatment of disease. Also provided is the corresponding use of a compound as disclosed herein in the treatment of a beta-1 adrenoreceptor and/or calcium channel mediated disorder. Also provided is the corresponding use of a compound as disclosed herein in the manufacture of a medicament for the treatment of a disease, for example a beta-1 adrenoreceptor and/or calcium channel-mediated disorder.

In certain embodiments, the disorder is selected from the group consisting of cardiac infarction, angina pectoris, atrial fibrillation, cardiac arrhythmia, congestive heart failure, hypertrophic obstructive cardiomyopathy, essential tremor, glaucoma, hypertension, migraine (prophylaxis), mitral valve prolapse, myocardial infarction, pheochromocytoma, postural orthostatic tachycardia syndrome, anxiety, hyperhidrosis, and hyperthyroidism.

In certain embodiments, the method further comprises the administration of an additional therapeutic agent.

In certain embodiments, the additional therapeutic agent is a compound of structural Formula II:

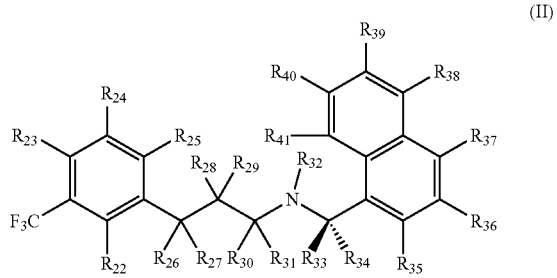

or a salt thereof, wherein:

$R_{22}$-$R_{32}$ and $R_{34}$-$R_{41}$ are independently selected from the group consisting of hydrogen and deuterium;

$R_{33}$ is selected from the group consisting of —$CH_3$, —$CH_2D$; —$CD_2H$, and —$CD_3$; and at least one of $R_{22}$-$R_{41}$ is deuterium or contains deuterium.

In certain embodiments, the additional therapeutic agent is a compound of structural Formula III:

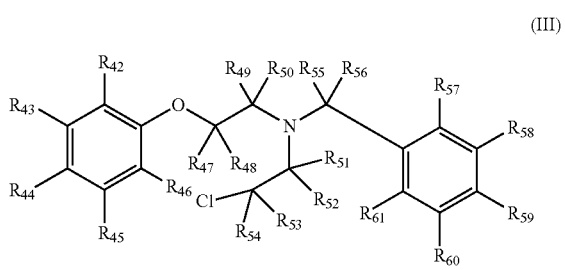

or a salt thereof, wherein:

$R_{42}$-$R_{49}$ and $R_{51}$-$R_{61}$ are independently selected from the group consisting of hydrogen and deuterium;

$R_{50}$ is selected from the group consisting of —$CH_3$, —$CH_2D$; —$CD_2H$, and —$CD_3$; and at least one of $R_{42}$-$R_{61}$ is deuterium or contains deuterium.

In certain embodiments, the additional therapeutic agent is selected from the group consisting of tetrabenazine, dihydrotetrabenazine, a deuterated analog of tetrabenazine, and a deuterated analog of dihydrotetrabenazine.

In certain embodiments, the method of treatment further results in at least one effect selected from the group consisting of:

a. decreased inter-individual variation in plasma levels of the compound or a metabolite thereof as compared to the non-isotopically enriched compound;
b. increased average plasma levels of the compound per dosage unit thereof as compared to the non-isotopically enriched compound;
c. decreased average plasma levels of at least one metabolite of the compound per dosage unit thereof as compared to the non-isotopically enriched compound;
d. increased average plasma levels of at least one metabolite of the compound per dosage unit thereof as compared to the non-isotopically enriched compound; and
e. an improved clinical effect during the treatment in the subject per dosage unit thereof as compared to the non-isotopically enriched compound.

In certain embodiments, the method further results in at least two effects selected from the group consisting of:

a. decreased inter-individual variation in plasma levels of the compound or a metabolite thereof as compared to the non-isotopically enriched compound;
b. increased average plasma levels of the compound per dosage unit thereof as compared to the non-isotopically enriched compound;
c. decreased average plasma levels of at least one metabolite of the compound per dosage unit thereof as compared to the non-isotopically enriched compound;
d. increased average plasma levels of at least one metabolite of the compound per dosage unit thereof as compared to the non-isotopically enriched compound; and
e. an improved clinical effect during the treatment in the subject per dosage unit thereof as compared to the non-isotopically enriched compound.

In certain embodiments, the method effects a decreased metabolism of the compound per dosage unit thereof by at least one polymorphically-expressed cytochrome P450 isoform in the subject, as compared to the corresponding non-isotopically enriched compound.

In certain embodiments, the cytochrome P450 isoform is selected from the group consisting of CYP2C8, CYP2C9, CYP2C19, CYP3A4, and CYP2D6.

In certain embodiments, the compound is characterized by decreased inhibition of at least one cytochrome P450 or monoamine oxidase isoform in the subject per dosage unit thereof as compared to the non-isotopically enriched compound.

In certain embodiments, the cytochrome P450 or monoamine oxidase isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, MAOA, and MAOB.

In certain embodiments, the method reduces a deleterious change in a diagnostic hepatobiliary function endpoint, as compared to the corresponding non-isotopically enriched compound.

In certain embodiments, the diagnostic hepatobiliary function endpoint is selected from the group consisting of alanine aminotransferase ("ALT"), serum glutamic-pyruvic transaminase ("SGPT"), aspartate aminotransferase ("AST," "SGOT"), ALT/AST ratios, serum aldolase, alkaline phosphatase ("ALP"), ammonia levels, bilirubin, gamma-glutamyl transpeptidase ("GGTP," "γ-GTP," "GGT"), leucine aminopeptidase ("LAP"), liver biopsy, liver ultrasonography, liver nuclear scan, 5'-nucleotidase, and blood protein.

Also provided is a compound as disclosed herein for use as a medicament.

Also provided is a compound as disclosed herein for use in the manufacture of a medicament for the prevention or treatment of a disorder ameliorated by the inhibition of VMAT2.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

As used herein, the terms below have the meanings indicated.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ ... to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%; deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium," when used to describe a given position in a molecule such as $R_1$-$R_{61}$ or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease" and "condition" (as in medical condition), in that all reflect an abnormal condition of the human or animal body or of one of its parts that impairs normal functioning, is typically manifested by distinguishing signs and symptoms.

The terms "treat," "treating," and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent," "preventing," and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "VMAT2" refers to vesicular monoamine transporter 2, an integral membrane protein that acts to transport monoamines—particularly neurotransmitters such as dopamine, norepinephrine, serotonin, and histamine—from cellular cytosol into synaptic vesicles.

The term "VMAT2-mediated disorder," refers to a disorder that is characterized by abnormal VMAT2 activity. A VMAT2-mediated disorder may be completely or partially mediated by modulating VMAT2. In particular, a VMAT2-mediated disorder is one in which inhibition of VMAT2 results in some effect on the underlying disorder e.g., administration of a VMAT2 inhibitor results in some improvement in at least some of the patients being treated.

The term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate.

The term "beta-1 adreneoreceptor antagonist activity", "antagonism of beta-1 adrenoreceptors" or "antagonizing beta-1 adrenoreceptors" refers to the ability of a compound herein to inhibit signaling pathways mediated by beta-1 adrenoreceptors by binding to the receptors. The antagonistic activity may be competitive antagonism, non-competitive antagonism, or partial antagonism. Such compounds are sometimes called "beta blockers."

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenicity, are commensurate with a reasonable benefit/risk ratio, and are effective for their intended use.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio.

The terms "active ingredient," "active compound," and "active substance" refer to a compound, which is administered, alone or in combination with one or more pharmaceutically acceptable excipients or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

The compounds disclosed herein can exist as therapeutically acceptable salts. The term "therapeutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (+)-DL-lactic acid, lactobionic acid, lauric acid, maleic acid, (−)-L-malic acid, malonic acid, (+)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art.

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods of treating a VMAT2-mediated disorder comprising administering to a subject having or suspected to have such a disorder, a therapeutically effective amount of a compound as disclosed herein or a pharmaceutically acceptable salt, solvate, or prodrug thereof.

VMAT2-mediated disorders, include, but are not limited to, chronic hyperkinetic movement disorders, Tourette's syndrome, Parkinson's disease, Huntington's disease, Huntington's chorea, Sydenham's chorea, tardive dyskinesia/dystonia, Parkinson's disease levodopa-induced dyskinesia, levodopa-induced dyskinesia, ataxia, corticobasal degeneration, dyskinesias (paroxysmal), dystonia (general, segmental, focal) including blepharospasm, spasmodic torticollis (cervical dystonia), writer's cramp (limb dystonia), laryngeal dystonia (spasmodic dysphonia), and oromandibular dystonia, essential tremor, hereditary spastic paraplegia, multiple system atrophy (Shy Drager Syndrome), myoclonus, progressive supranuclear palsy, restless legs syndrome, Rett Syndrome, spasticity due to stroke, cerebral palsy, multiple sclerosis, spinal cord or brain injury, tics, Wilson's Disease, oppositional defiant disorder, Huntington's disease like diseases (HDL1, HDL2 and HDL3), benign hereditary chorea, neuroacanthocytosis, neurodegeneration with brain iron accumulation (NBIA), athetosis, Friedreich ataxia, spinocerebellar ataxia, multiple system atrophy, dentatorubralpallidoluysian atrophy, ataxia with oculomotor apraxia (types 1 and 2), ataxia telangiectasia, focal dystonias, idiopathic dystonias such as Oppenheim dystonia and torticollis, dystonia-plus syndromes, secondary dystonias, Duchenne muscular dystrophy, and Down syndrome, and/or any disorder which can lessened, alleviated, or prevented by administering a VMAT2 inhibitor.

Disclosed herein are methods of treating cardiovascular disorders ameliorated by antagonizing beta-1 adrenoreceptors, and/or calcium channel blocking, comprising administering to a subject having or suspected to have such a disorder, a therapeutically effective amount of a compound disclosed herein or a pharmaceutically acceptable salt, solvate, or prodrug thereof.

Disorders ameliorated by antagonizing beta-1 adrenoreceptors, and/or calcium channel blocking, include, but are not limited to, cardiac infarction, angina pectoris, atrial fibrillation, cardiac arrhythmia, congestive heart failure, hypertrophic obstructive cardiomyopathy, essential tremor, glaucoma, hypertension, migraine (prophylaxis), mitral valve prolapse, myocardial infarction, pheochromocytoma, postural orthostatic tachycardia syndrome, anxiety, hyperhidrosis, and hyperthyroidism.

In certain embodiments, a method of treating a VMAT2, beta-1 adrenoreceptors, and/or calcium channel-mediated disorder comprises administering to the subject a therapeutically effective amount of a compound of as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome $P_{450}$ or monoamine oxidase isoform in the subject; (4) decreased metabolism via at least one polymorphically-expressed cytochrome $P_{450}$ isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome $P_{450}$ or monoamine oxidase isoform by a compound as disclosed herein is decreased; or metabolism of the compound as disclosed herein by at least one polymorphically-expressed cytochrome $P_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described in Kaplan et al., New Drugs Annual: Cardiovascular Drugs, 1985, Vol. 3, which are hereby incorporated by reference.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome $P_{450}$ isoform is measured by the method of Ko et al. (*British Journal of Clinical Pharmacology*, 2000, 49, 343-351). The inhibition of the $MAO_A$ isoform is measured by the method of Weyler et al. (*J. Biol Chem.* 1985, 260, 13199-13207). The inhibition of the $MAO_B$ isoform is measured by the method of Uebelhack et al. (*Pharmacopsychiatry*, 1998, 31, 187-192).

Examples of polymorphically-expressed cytochrome $P_{450}$ isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of improved disorder-control and/or disorder-eradication endpoints, or improved clinical effects include, but are not limited to, change from baseline in the chorea score of the Unified Huntington's Disease Rating Scale (UHDRS).

Further examples of improved disorder-control and/or disorder-eradication endpoints, or improved clinical effects include, but are not limited to:
a. reduced aggressiveness;
b. reduction of the rate or severity of incidents of temper loss;
c. reduction of the rate or severity of incidents of arguing with adults;
d. reduction of the rate or severity of incidents of defiance or refusal to comply with adults' requests or rules;
e. reduction of the rate or severity of incidents of blaming others for his or her misbehavior or mistakes;
f. reduced touchiness or ease of annoyance by others;
g. reduced anger and/or resentfulness;
h. reduced spitefulness and/or vindictiveness;
i. reduction of the rate or severity of incidents of arguing;
j. reduction of the rate or severity of incidents of claiming not to care about losing privileges as a consequence to negative behavior;
k. reduction of the rate or severity of incidents of placing blame on others;
l. reduction of the rate or severity of incidents of not accepting responsibility for actions;
m. reduction of the rate or severity of incidents of ignoring directives;
n. reduction of the rate or severity of incidents of playing adults against each other;
o. reduction of the rate or severity of incidents of refusing to go to "time out";
p. reduction of the rate or severity of incidents of resisting directions;
q. reduced stubbornness;
r. reduction of the rate or severity of incidents of testing limits; and
s. reduction of the rate or severity of incidents of unwillingness to compromise, give in, or negotiate with adults or peers.

Further examples of improved disorder-control and/or disorder-eradication endpoints, or improved clinical effects include, but are not limited to:
a. improved Unified Parkinson's Disease Rating Scale scores;
b. improved Abnormal Involuntary Movement Scale scores;
c. improved Goetz Dyskinesia Rating Scale scores;
d. improved Unified Dyskinesia Rating Scale scores;
e. improved PDQ-39 Parkinson's Disease Questionnaire scores; and
f. improved Global Primate Dyskinesia Rating Scale scores.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "□-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", $4^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of VMAT2-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more anti-psychotics, including, but not limited to, chlorpromazine, levomepromazine, promazine, acepromazine, triflupromazine, cyamemazine, chlorproethazine, dixyrazine, fluphenazine, perphenazine, prochlorperazine, thiopropazate, trifluoperazine, acetophenazine, thioproperazine, butaperazine, perazine, periciazine, thioridazine, mesoridazine, pipotiazine, haloperidol, trifluperidol, melperone, moperone, pipamperone, bromperidol, benperidol, droperidol, fluanisone, oxypertine, molindone, sertindole, ziprasidone, flupentixol, clopenthixol, chlorprothixene, thiothixene, zuclopenthixol, fluspirilene, pimozide, penfluridol, loxapine, clozapine, olanzapine, quetiapine, tetrabenazine, sulpiride, sultopride, tiapride, remoxipride, amisulpride, veralipride, levosulpiride, lithium, prothipendyl, risperidone, clotiapine, mosapramine, zotepine, pripiprazole, and paliperidone.

In certain embodiments, the compounds disclosed herein can be combined with one or more benzodiazepines ("minor tranquilizers"), including, but not limited to alprazolam, adinazolam, bromazepam, camazepam, clobazam, clonazepam, clotiazepam, cloxazolam, diazepam, ethyl loflazepate, estizolam, fludiazepam, flunitrazepam, halazepam, ketazolam, lorazepam, medazepam, dazolam, nitrazepam, nordazepam, oxazepam, potassium clorazepate, pinazepam, prazepam, tofisopam, triazolam, temazepam, and chlordiazepoxide.

In certain embodiments, the compounds disclosed herein can be combined with olanzapine or pimozide.

In certain embodiments, the compounds disclosed herein can be combined with one or more dopamine precursors, including, but not limited to, levodopa.

In certain embodiments, the compounds disclosed herein can be combined with one or more DOPA decarboxylase inhibitors, including, but not limited to, carbidopa.

In certain embodiments, the compounds disclosed herein can be combined with one or more catechol-O-methyl transferase (COMT) inhibitors, including, but not limited to, opicapone, entacapone and tolcapone.

In certain embodiments, the compounds disclosed herein can be combined with one or more dopamine receptor agonists, including, but not limited to, apomorphine, bromocriptine, ropinirole, and pramipexole.

In certain embodiments, the compounds disclosed herein can be combined with one or more neuroprotective agents, including, but not limited to, selegeline and riluzole.

In certain embodiments, the compounds disclosed herein can be combined with one or more NMDA antagonists, including, but not limited to, amantidine.

In certain embodiments, the compounds disclosed herein can be combined with one or more benzodiazepines ("minor tranquilizers"), including, but not limited to alprazolam, adinazolam, bromazepam, camazepam, clobazam, clonazepam, clotiazepam, cloxazolam, diazepam, ethyl loflazepate, estizolam, fludiazepam, flunitrazepam, halazepam, ketazolam, lorazepam, medazepam, dazolam, nitrazepam, nordazepam, oxazepam, potassium clorazepate, pinazepam, prazepam, tofisopam, triazolam, temazepam, and chlordiazepoxide.

In certain embodiments, the compounds disclosed herein can be combined with olanzapine or pimozide.

In certain embodiments, the DOPA decarboxylase inhibitor is carbidopa.

In certain embodiments, the catechol-O-methyl transferase (COMT) inhibitor is selected from the group consisting of opicapone, entacapone and tolcapone.

In certain embodiments, the dopamine receptor agonist is selected from the group consisting of apomorphine, bromocriptine, ropinirole, and pramipexole.

In certain embodiments, the neuroprotective agent is selected from the group consisting of selegeline and riluzole.

In certain embodiments, the NMDA antagonist is amantadine.

In certain embodiments, the anti-psychotic is clozapine.

In certain embodiments, the compounds disclosed herein can be combined with one or more compounds of structural Formula II:

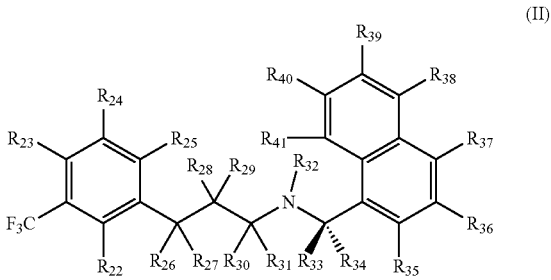

(II)

or a salt thereof, wherein:

$R_{22}$-$R_{32}$ and $R_{34}$-$R_{41}$ are independently selected from the group consisting of hydrogen and deuterium;

$R_{33}$ is selected from the group consisting of —$CH_3$, —$CH_2D$; —$CD_2H$, and —$CD_3$; and at least one of $R_{22}$-$R_{41}$ is deuterium or contains deuterium.

In certain embodiments, the compounds disclosed herein can be combined with one or more compounds of structural Formula III:

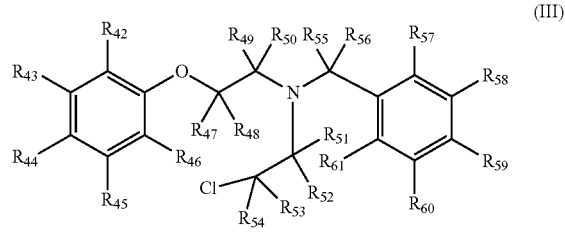

(III)

or a salt thereof, wherein:

$R_{42}$-$R_{49}$ and $R_{51}$-$R_{61}$ are independently selected from the group consisting of hydrogen and deuterium;

$R_{50}$ is selected from the group consisting of —$CH_3$, —$CH_2D$; —$CD_2H$, and —$CD_3$; and at least one of $R_{42}$-$R_{61}$ is deuterium or contains deuterium.

In certain embodiments, the compounds disclosed herein can be combined with tetrabenazine or a deuterated analog of tetrabenazine.

In certain embodiments, the compounds disclosed herein can be combined with one or more compounds or compositions as disclosed in US20150004231, which is hereby incorporated by reference in its entirety.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepam; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; famesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating VMAT2-mediated disorders in a human or animal subject in need of such treatment comprising administering to the subject an amount of a compound disclosed herein effective to reduce or prevent the disorder in the subject, in combination with at least one additional agent for the treatment of the disorder that is known in the art. In a related aspect, certain embodiments provide therapeutic compositions comprising at least one compound disclosed herein in combination with one or more additional agents for the treatment of VMAT2-mediated disorders.

General Synthetic Methods for Preparing Compounds

Isotopic hydrogen can be introduced into a compound as disclosed herein by synthetic techniques that employ deuterated reagents, whereby incorporation rates are predetermined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described in the Example section herein and routine modifications thereof, and/or procedures found in EP 165682, which are hereby incorporated in their entirety, and references cited therein and routine modifications thereof. Compounds as disclosed herein can also be prepared as shown in any of the following schemes and routine modifications thereof.

The following schemes can be used to practice the present invention. Any position shown as hydrogen may optionally be replaced with deuterium.

such as water, to afford compound 7. Compound 4 is reacted with compound 7 to give a compound of formula I.

Deuterium can be incorporated to different positions synthetically, according to the synthetic procedures as shown in Scheme I, by using appropriate deuterated intermediates. For example, to introduce deuterium at $R_1$-$R_2$, compound 2 with the corresponding deuterium substitutions can be used. To introduce deuterium at one or more positions of $R_3$-$R_9$, compound 1 with the corresponding deuterium substitutions can be used. To introduce deuterium at one or more positions of $R_{17}$-$R_{21}$, compound 5 with the corre-

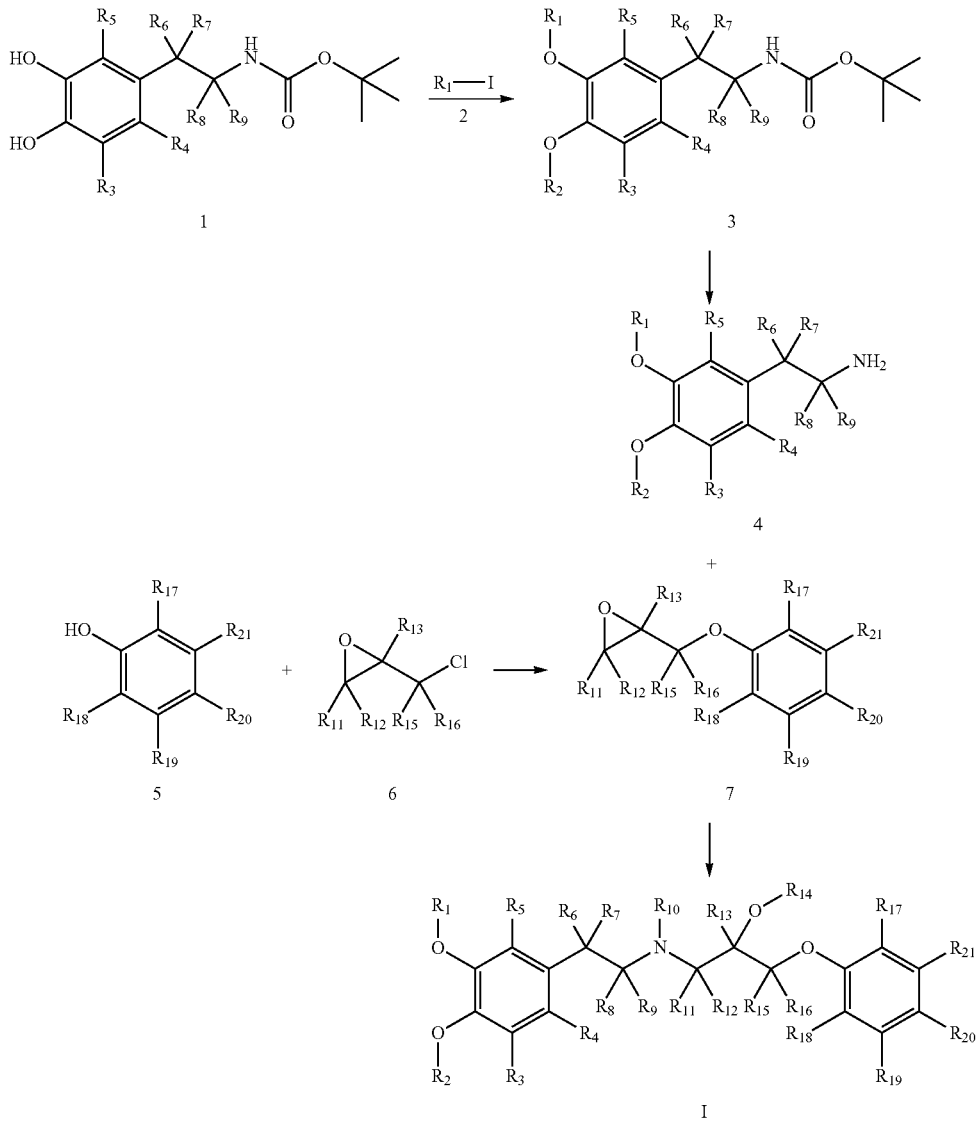

Scheme I

Compound 1 is reacted with compound 2 in the presence of an appropriate base, such as potassium carbonate, in an appropriate solvent, such as acetone, to afford compound 3. Compound 3 is treated with an appropriate deprotecting agent, such as trifluoroacetic acid, in an appropriate solvent, such as dichloromethane, to give compound 4. Compound 5 is reacted with compound 6 in the presence of an appropriate base, such as sodium hydroxide, in an appropriate solvent, sponding deuterium substitutions can be used. To introduce deuterium at one or more positions of $R_{11}$-$R_{13}$ and $R_{15}$-$R_{16}$, compound 12 with the corresponding deuterium substitutions can be used.

Deuterium can be incorporated to various positions having an exchangeable proton, such as the amine N—H and hydroxyl O—H, via proton-deuterium equilibrium exchange. For example, to introduce deuterium at $R_{10}$ and $R_{14}$, these protons may be replaced with deuterium selectively or non-selectively through a proton-deuterium exchange method known in the art.

The invention is further illustrated by the following examples. All IUPAC names were generated using CambridgeSoft's ChemDraw 10.0.

EXAMPLES

Example 1

[2-(3,4-dimethoxyphenyl)ethyl][2-hydroxy-3-(3-methylphenoxy)propyl]amine (Bevantolol)

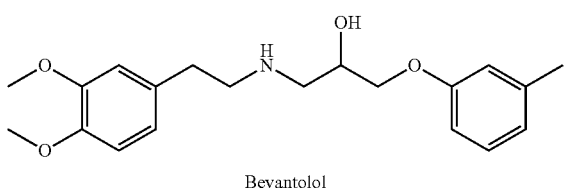

Bevantolol

Step 1

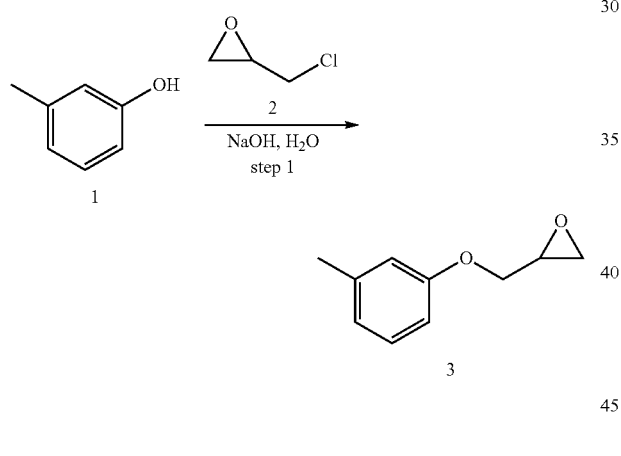

2-(3-methylphenoxymethyl)oxirane

To a solution of sodium hydroxide (10 g, 250 mmol, 1.25 equiv) in water (240 mL) was added 3-methylphenol (21.6 g, 200 mmol, 1.0 equiv). The resulting solution was stirred for 1.5 h at 20° C. To this was added 2-(chloromethyl)oxirane (27.6 g, 298 mmol, 1.50 equiv). The resulting solution was stirred at 20° C. overnight. The pH value of the solution was adjusted to 8-9 with hydrogen chloride (1 M). The resulting solution was extracted with dichloromethane (3×200 mL). The combined organic layers were washed with water (2×200 mL), brine (2×100 mL), then dried over anhydrous sodium sulfate and concentrated under vacuum. The residue was purified by a silica gel column, eluted with dichloromethane/petroleum ether (1:15-1:1) to afford 20 g (61%) of 2-(3-methylphenoxymethyl)oxirane as light yellow oil. $^1$H NMR (400 MHz, CDCl$_3$) δ: 2.36 (s, 3H), 2.78-2.80 (m, 1H), 2.92-2.94 (m, 1H), 3.36-3.39 (m, 1H), 3.96-4.00 (m, 1H), 4.20-4.24 (m, 1H), 6.74-6.83 (m, 3H), 7.18-7.22 (m, 1H).

Step 2

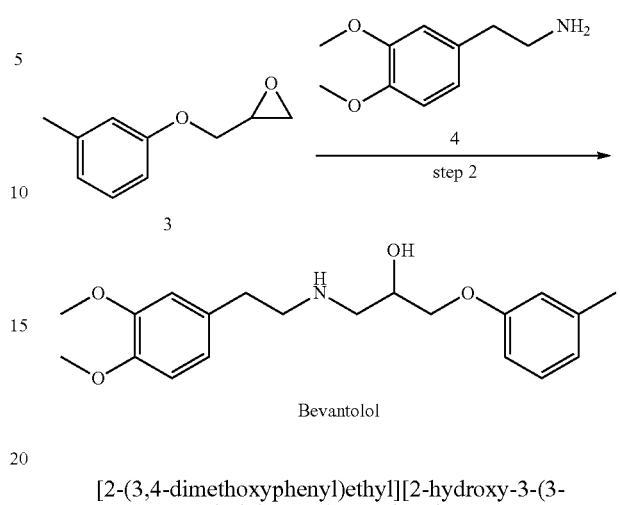

[2-(3,4-dimethoxyphenyl)ethyl][2-hydroxy-3-(3-ethylphenoxy)propyl]amine

To a solution of 2-(3,4-dimethoxyphenyl)ethan-1-amine (1 g, 5.52 mmol, 1.00 equiv) in ethanol (10 mL) was added 2-(3-methylphenoxymethyl)oxirane (900 mg, 5.48 mmol, 1.00 equiv). The resulting solution was stirred overnight at 20° C. The solids were filtered out and washed with methanol (100 mL). The filtrate was concentrated under vacuum. The residue was purified by a C18 silica gel column, eluted with CH$_3$CN/H$_2$O (1:1) to afford 460 mg (24%) of [2-(3,4-dimethoxyphenyl)ethyl][2-hydroxy-3-(3-methylphenoxy)propyl]amine as a white solid. $^1$H NMR (400 MHz, CDCl$_3$) δ: 2.34 (s, 3H), 2.77-2.84 (m, 3H), 2.88-2.97 (m, 3H), 3.88 (s, 3H), 3.89 (s, 3H), 3.97-3.98 (m, 2H), 4.03-4.08 (m, 1H), 6.71-6.83 (m, 6H), 7.16-7.20 (m, 1H). LC-MS: m/z=346 [M+H]$^+$.

Example 2

[2-[3,4-bis($^2$H$_6$)methoxyphenyl]ethyl][2-hydroxy-3-(3-methylphenoxy)propyl]amine Step 1

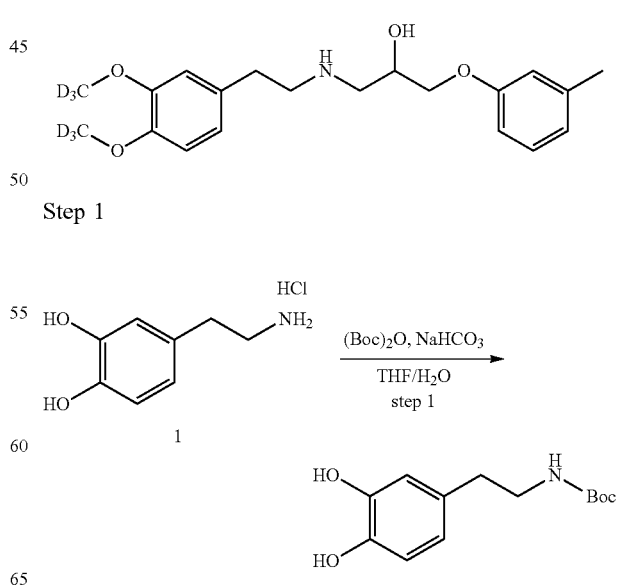

tert-butyl N-[2-(3,4-dihydroxyphenyl)ethyl]carbamate

To a solution of 4-(2-aminoethyl)benzene-1,2-diol (6 g, 31.75 mmol, 1.00 equiv) in tetrahydrofuran (60 mL) and water (12 mL) were added sodium bicarbonate (5.8 g, 69.04 mmol, 2.50 equiv) and (Boc)$_2$O (6.6 g, 30.24 mmol, 1.10 equiv). The resulting solution was stirred for 3 h at 20° C. The reaction was then quenched by the addition of water (50 mL). The resulting solution was extracted with ethyl acetate (2×50 mL). The organic layers were combined, washed with water (1×100 mL), brine (1×200 mL), dried over anhydrous sodium sulfate, filtered and concentrated under vacuum to afford 8 g (99%) of tert-butyl N-[2-(3,4-dihydroxyphenyl)ethyl]carbamate as a wine solid.

Step 2

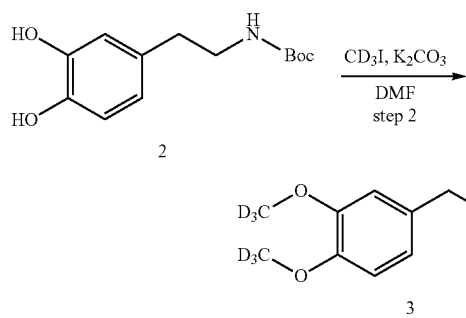

tert-butyl N-[2-[3,4-bis($^2$H$_6$)methoxyphenyl]ethyl]carbamate

To a solution of tert-butyl N-[2-(3,4-dihydroxyphenyl)ethyl]carbamate (6 g, 23.69 mmol, 1.00 equiv) and potassium carbonate (9.82 g, 71.05 mmol, 3.00 equiv) in N,N-dimethylformamide (60 mL) was added CD$_3$I (10.32 g, 71.22 mmol, 3.00 equiv) in several portions. The resulting solution was stirred overnight at 20° C. The reaction was then quenched by the addition of water (120 mL). The resulting solution was extracted with ethyl acetate (3×100 mL). The organic layers were combined, washed with water (2×100 mL), brine (2×200 mL), dried over anhydrous sodium sulfate, filtered and concentrated under vacuum to afford 6.7 g (98%) of tert-butyl N-[2-[3,4-bis($^2$H$_6$)methoxyphenyl]ethyl]carbamate as a brown solid.

Step 3

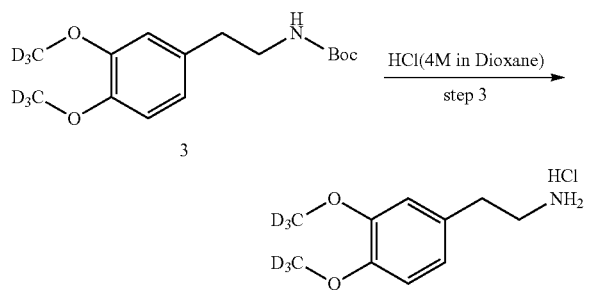

2-[3,4-bis($^2$H$_6$)methoxyphenyl]ethan-1-amine

To a solution of hydrogen chloride (4 M in dioxane) (32.5 mL) was added tert-butyl N-[2-[3,4-bis($^2$H$_6$)methoxyphenyl]ethyl]carbamate (6.5 g, 22.62 mmol, 1.00 equiv). The resulting solution was stirred for 0.5 h at 20° C. The solids were collected by filtration, washed with diethyl ether (2×100 mL) and concentrated under vacuum to afford 3.7 g (73%) of 2-[3,4-bis($^2$H$_6$)methoxyphenyl]ethan-1-amine as a white solid. $^1$H NMR (400 MHz, DMSO-d$_6$) δ: 2.80-2.84 (m, 2H), 2.96-3.03 (m, 2H), 6.75-6.90 (m, 3H), 8.09 (brs, 3H).

Step 4

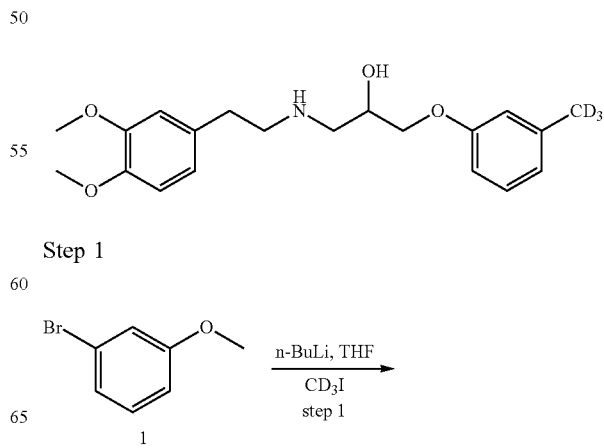

[2-[3,4-bis($^2$H$_6$)methoxyphenyl]ethyl][2-hydroxy-3-(3-methylphenoxy)propyl]amine To a solution of 2-[3,4-bis($^2$H$_6$)methoxyphenyl]ethan-1-amine (1 g, 4.47 mmol, 1.00 equiv) and potassium carbonate (926 mg, 6.71 mmol, 1.50 equiv) in ethanol (15 mL) was added 2-(3-methylphenoxymethyl)oxirane (734 mg, 4.48 mmol, 1.00 equiv). The resulting solution was stirred overnight at 20° C. The solids were filtered out and washed with methanol (100 mL). The filtrate was concentrated under vacuum. The residue was purified by a C18 silica gel column, eluted with CH$_3$CN/H$_2$O (1:1) to afford 200 mg (12.7%) of [2-[3,4-bis($^2$H$_6$)methoxyphenyl]ethyl][2-hydroxy-3-(3-methylphenoxy)propyl]amine as a white solid. $^1$H NMR (400 MHz, CDCl$_3$) δ: 2.34 (s, 3H), 2.75-2.83 (m, 3H), 2.88-2.99 (m, 3H), 3.97-3.98 (m, 2H), 4.03-4.08 (m, 1H), 6.71-6.83 (m, 6H), 7.16-7.20 (m, 1H). LC-MS: m/z=352 [M+H]$^+$.

Example 3

[2-(3,4-dimethoxyphenyl)ethyl]([2-hydroxy-3-[3-($^2$H$_3$)methylphenoxy]propyl])amine Step 1

-continued

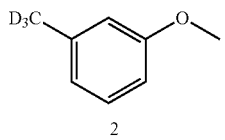

2

1-methoxy-3-(²H₃)methylbenzene as Light Yellow Oil

To a solution of 1-bromo-3-methoxybenzene (20 g, 106.94 mmol, 1.00 equiv) in THF (200 mL) was added n-BuLi (47.4 mL, 1.10 equiv) at −78° C. under an atmosphere of N₂. The resulting solution was stirred for 30 min at −78° C. Then CD₃I (18.8 g, 1.20 equiv) was added at −78° C. The resulting solution was stirred for 30 min at −10° C. The reaction was then quenched by the addition of NH₄Cl. The resulting solution was extracted with of ethyl acetate (3×80 mL). The organic layers were combined, dried over anhydrous sodium sulfate and concentrated under vacuum to afford 9 g (67.5%) of 1-methoxy-3-(²H₃)methylbenzene as light yellow oil.
Step 2

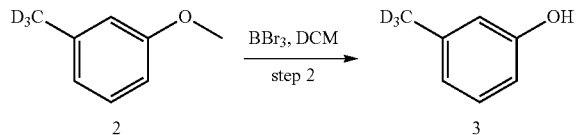

3-(²H₃)methylphenol as Brown Oil

To a solution of 1-methoxy-3-(²H₃)methylbenzene (9 g, 71.89 mmol, 1.00 equiv) in dichloromethane (10 mL) was added BBr₃ (144 mL, 2.00 equiv) at −60° C. The resulting solution was stirred for 2 h at 0° C. The reaction was then quenched by the addition of water/ice. The resulting solution was extracted with dichloromethane (3×50 mL). The organic layers were treated with sodium hydroxide solution (10%). Then the aqueous layers were acidified with hydrogen chloride (1 M), extracted with dichloromethane (3×50 mL), dried over anhydrous sodium sulfate and concentrated under vacuum to afford 6 g (75%) of 3-(²H₃)methylphenol as brown oil.
Step 3

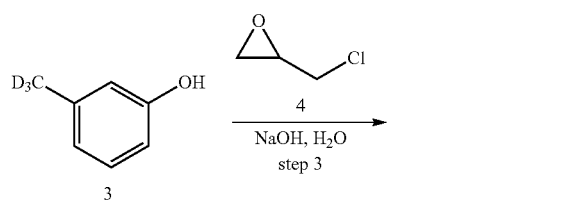

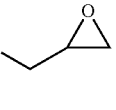

2-[3-(²H₃)methylphenoxymethyl]oxirane

To a solution of sodium hydroxide (2.25 g, 56.25 mmol, 1.25 equiv) in water (53.5 mL) was added 3-(²H₃)methylphenol (5 g, 44.98 mmol, 1.00 equiv). The resulting solution was stirred for 1.5 h at 20° C. To this was added 2-(chloromethyl)oxirane (6.22 g, 67.23 mmol, 1.50 equiv). The resulting solution was stirred at 20° C. overnight. The pH value of the solution was adjusted to 8-9 with hydrogen chloride (1 M). The resulting solution was extracted with dichloromethane (3×50 mL). The combined organic layers was washed with water (2×50 mL) and brine (2×50 mL), dried over anhydrous sodium sulfate and concentrated under vacuum. The residue was purified by a silica gel column, eluted with dichloromethane/petroleum ether (1:15-1:1) to afford 5.3 g (70%) of 2-[3-(²H₃)methylphenoxymethyl]oxirane as colorless oil. ¹H NMR (400 MHz, CDCl₃) δ: 2.77-2.79 (m, 1H), 2.92-2.94 (m, 1H), 3.36-3.40 (m, 1H), 3.96-4.01 (m, 1H), 4.21-4.24 (m, 1H), 6.76-6.84 (m, 3H), 7.19-7.23 (m, 1H).
Step 4

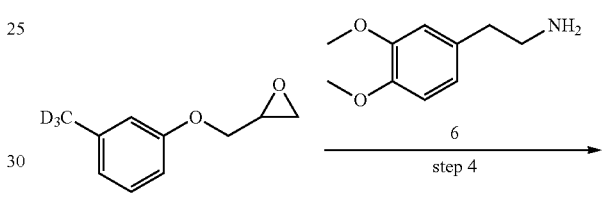

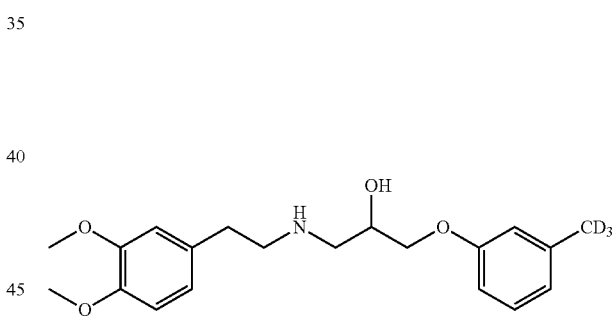

[2-(3,4-dimethoxyphenyl)ethyl]([2-hydroxy-3-[3-(²H₃)methylphenoxy]propyl])amine To a solution of 2-(3,4-dimethoxyphenyl)ethan-1-amine (2.17 g, 11.97 mmol, 1.00 equiv) and potassium carbonate (2.48 g, 17.94 mmol, 1.50 equiv) in ethanol (4.5 mL) was added 2-[3-(²H₃)methylphenoxymethyl]oxirane (2 g, 11.96 mmol, 1.00 equiv). The resulting solution was stirred overnight at 20° C. The solids were filtered out and washed with methanol (50 mL). The filtrate was concentrated under vacuum. The residue was purified by a C18 silica gel column, eluted with CH₃CN/H₂O (1:1) to afford 400 mg (10%) of [2-(3,4-dimethoxyphenyl)ethyl]([2-hydroxy-3-[3-(²H₃)methylphenoxy]propyl])amine as a white solid. ¹H NMR (400 MHz, CDCl₃) δ: 2.74-2.84 (m, 3H), 2.89-2.98 (m, 3H), 3.88 (s, 3H), 3.90 (s, 3H), 3.94-3.98 (m, 2H), 4.03-4.09 (m, 1H), 6.71-6.83 (m, 6H), 7.16-7.20 (m, 1H). LC-MS: m/z=349 [M+H]⁺.

Example 4

[2-[3,4-bis($^2$H$_6$)methoxyphenyl]ethyl]([2-hydroxy-3-[3-($^2$H$_3$)methylphenoxy]propyl])amine

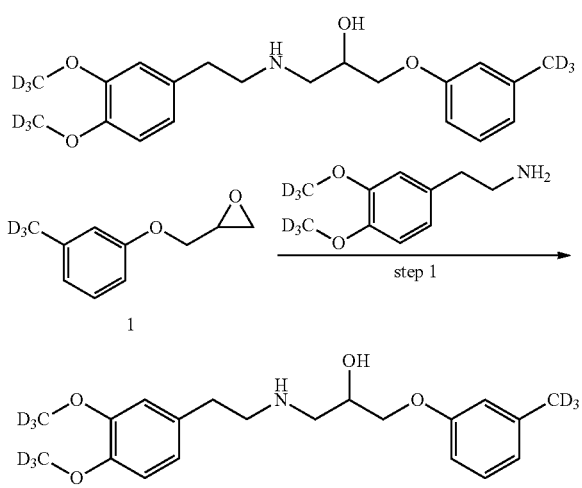

[2-[3,4-bis($^2$H$_6$)methoxyphenyl]ethyl]([2-hydroxy-3-[3-($^2$H$_3$)methylphenoxy]propyl])amine To a solution of 2-[3,4-bis($^2$H$_6$)methoxyphenyl]ethan-1-amine (1.2 g, 5.37 mmol, 1.00 equiv) and potassium carbonate (1.11 g, 8.03 mmol, 1.50 equiv) in ethanol (2.5 mL) was added 2-[3-($^2$H$_3$)methylphenoxymethyl]oxirane (900 mg, 5.38 mmol, 1.00 equiv). The resulting solution was stirred overnight at 20° C. The solids were filtered out and washed with methanol (50 mL). The filtrate was concentrated under vacuum. The residue was purified by a C18 silica gel column, eluted with CH$_3$CN/H$_2$O (1:1) to afford 300 mg (16%) of [2-[3,4-bis($^2$H$_6$)methoxyphenyl]ethyl]([2-hydroxy-3-[3-($^2$H$_3$)methylphenoxy]propyl])amine as a white solid. $^1$H NMR (400 MHz, CDCl$_3$) δ: 2.76-2.84 (m, 3H), 2.89-3.00 (m, 3H), 3.97-3.99 (m, 2H), 4.04-4.09 (m, 1H), 6.71-6.85 (m, 6H), 7.16-7.20 (m, 1H). LC-MS: m/z=355 [M+H]$^+$.

Example 5

1-([2-[3,4-bis($^2$H$_6$)methoxyphenyl]ethyl]amino)-3-(3-methylphenoxy)($^2$H$_5$) propan-2-ol

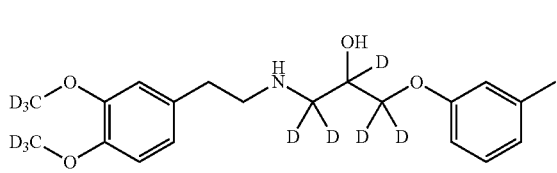 [SMILES: [2H]C([2H])([2H])Oc1ccc(CCNC([2H])([2H])C([2H])(O)C([2H])([2H])Oc2cccc(C)c2)cc1OC([2H])([2H])[2H]]

Step 1

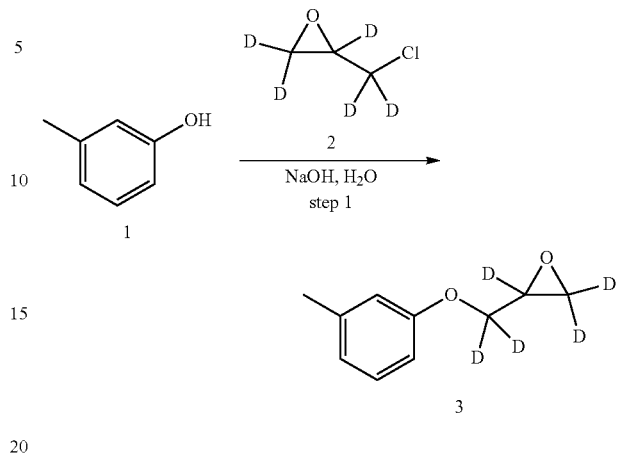

2-[3-methylphenoxy($^2$H$_2$)methyl]($^2$H$_3$)oxirane

To a solution of sodium hydroxide (10.0 g, 250 mmol, 1.25 equiv) in water (240 mL) was added 3-methylphenol (2.0 g, 18.49 mmol, 1.00 equiv). The resulting solution was stirred for 1.5 h at 20° C. To this was added 2-[chloro($^2$H$_2$)methyl]($^2$H$_3$)oxirane (2.7 g, 27.60 mmol, 1.50 equiv). The resulting solution was stirred at 20° C. overnight. The pH value of the solution was adjusted to 8-9 with hydrogen chloride (1 M). The resulting solution was extracted with dichloromethane (3×30 mL). The combined organic layers was washed with water (2×30 mL) and brine (2×30 mL), dried over anhydrous sodium sulfate and concentrated under vacuum. The residue was purified by a silica gel column, eluted with dichloromethane/petroleum ether (1:15-1:1) to afford 2.3 g (73%) of 2-[3-methylphenoxy($^2$H$_2$)methyl]($^2$H$_3$)oxirane as colorless oil. $^1$H NMR (400 MHz, CDCl$_3$) δ: 2.36 (s, 3H), 6.74-6.83 (m, 3H), 7.18-7.22 (m, 1H).

Step 2

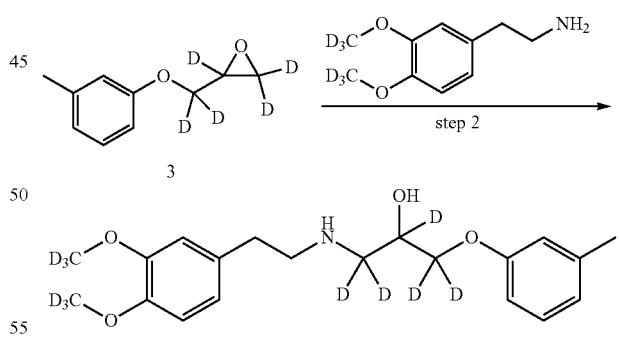

1-([2-[3,4-bis($^2$H$_6$)methoxyphenyl]ethyl]amino)-3-(3-methylphenoxy)($^2$H$_5$) propan-2-ol To a solution of 2-[3,4-bis($^2$H$_6$)methoxyphenyl]ethan-1-amine (1.2 g, 5.37 mmol, 1.00 equiv) and potassium carbonate (1.11 g, 8.03 mmol, 1.50 equiv) in ethanol (3 mL) was added 2-[3-methylphenoxy($^2$H$_2$)methyl]($^2$H$_3$)oxirane (910 mg, 5.38 mmol, 1.00 equiv). The resulting solution was stirred overnight at 20° C. The solids were filtered out and washed with methanol (100 mL). The filtrate was concentrated under vacuum. The residue was purified by a C18 silica gel column, eluted with $CH_3CN/H_2O$ (1:1) to afford 290 mg (15%) of 1-([2-[3,4-bis($^2H_6$)methoxyphenyl]ethyl]amino)-3-(3-methylphenoxy)($^2H_5$)propan-2-ol as a light yellow solid. $^1H$ NMR (400 MHz, $CDCl_3$) δ: 2.34 (s, 3H), 2.75-2.84 (m, 2H), 2.88-2.99 (m, 2H), 6.70-6.82 (m, 6H), 7.16-7.20 (m, 1H). LC-MS: m/z=357 $[M+H]^+$.

The following compounds can generally be made using the methods described above. It is expected that these compounds when made will have activity similar to those described in the examples above.

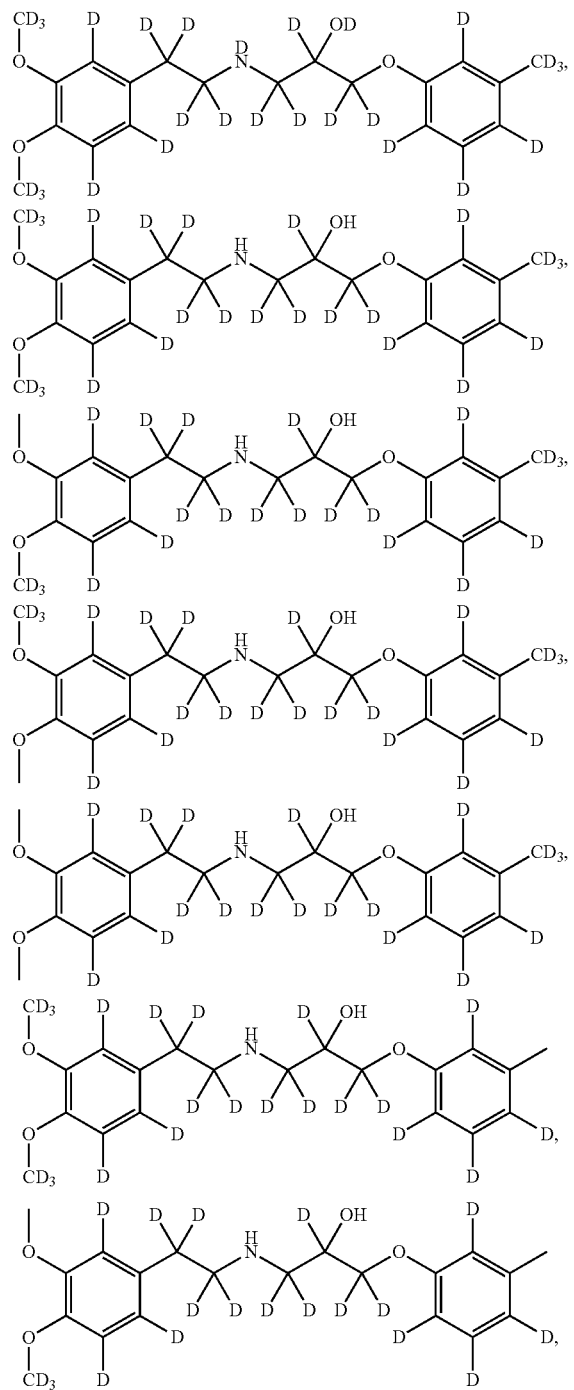

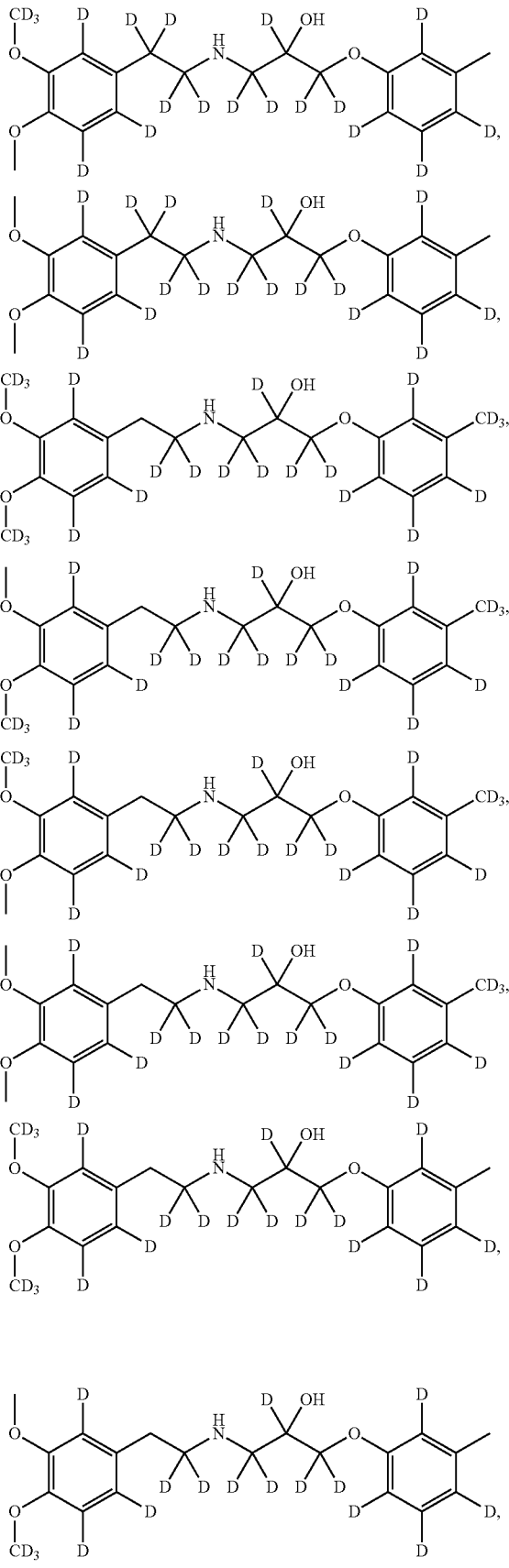

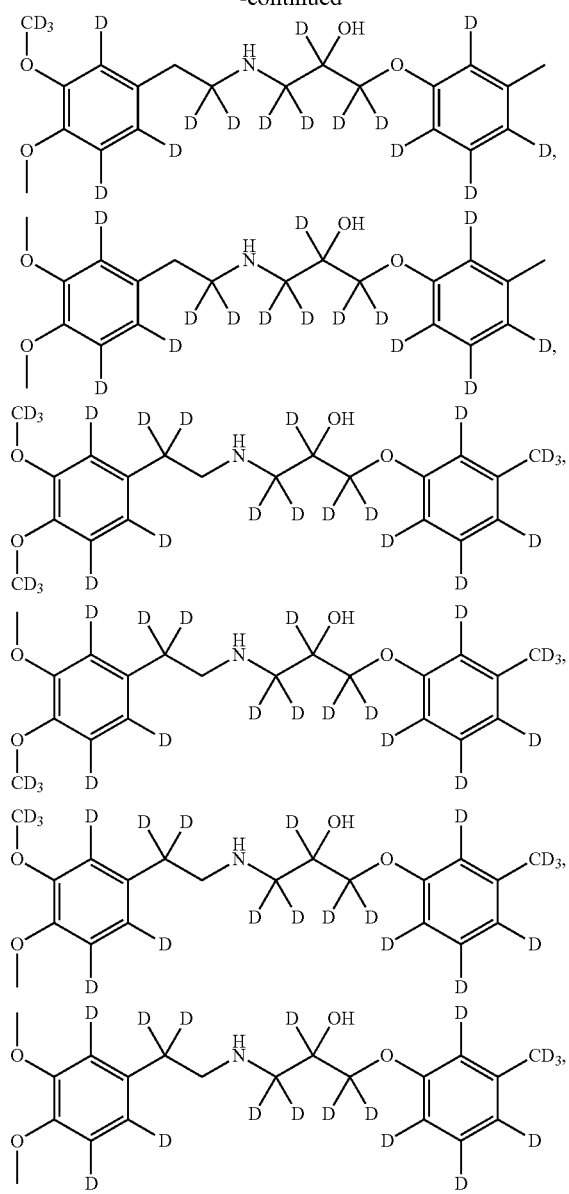
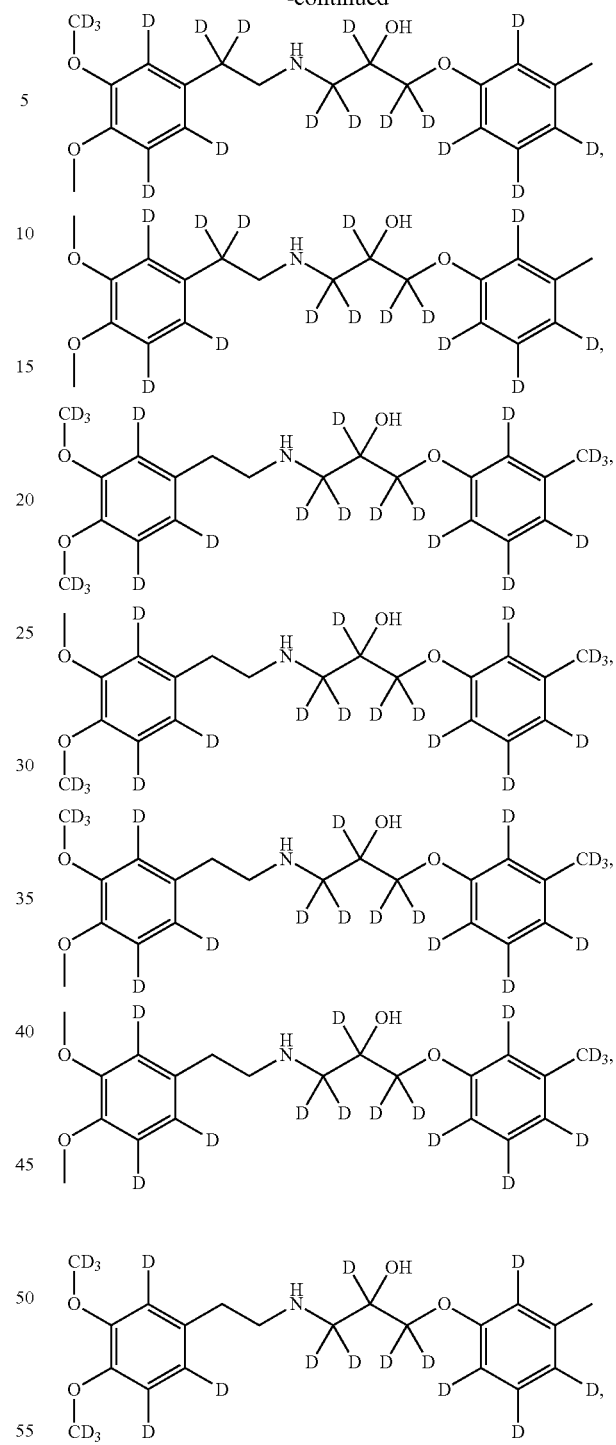
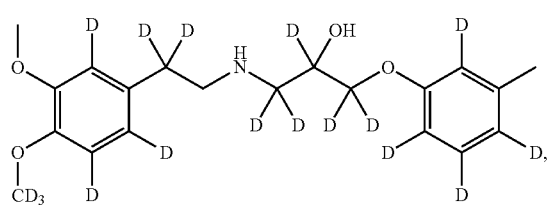

39
-continued
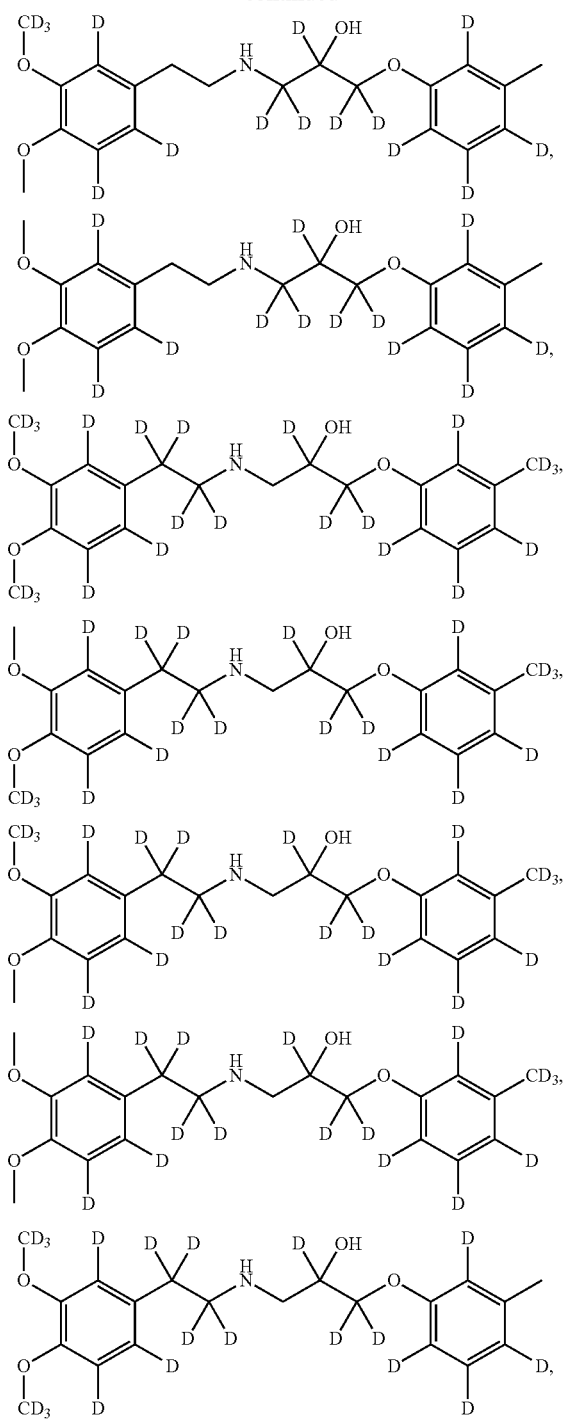
40
-continued
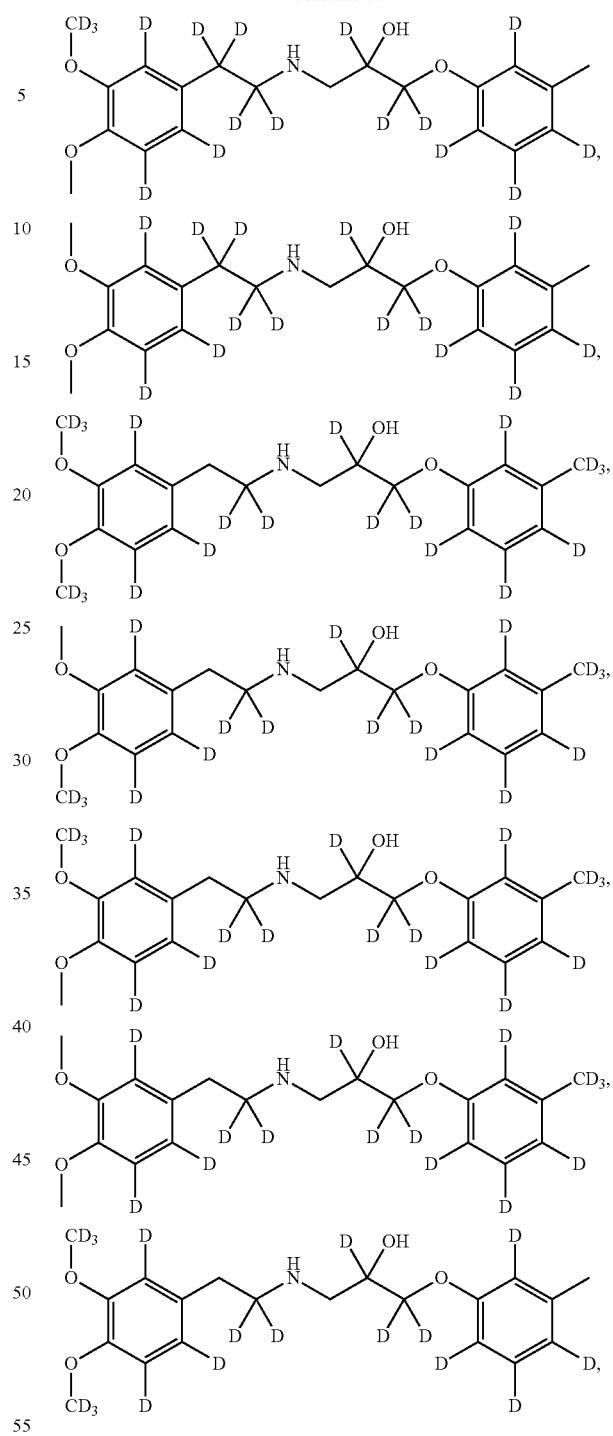
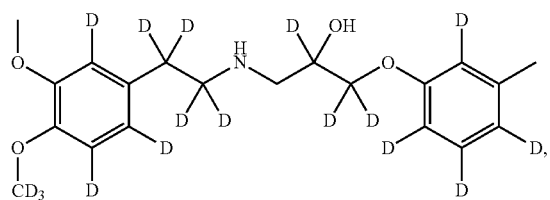

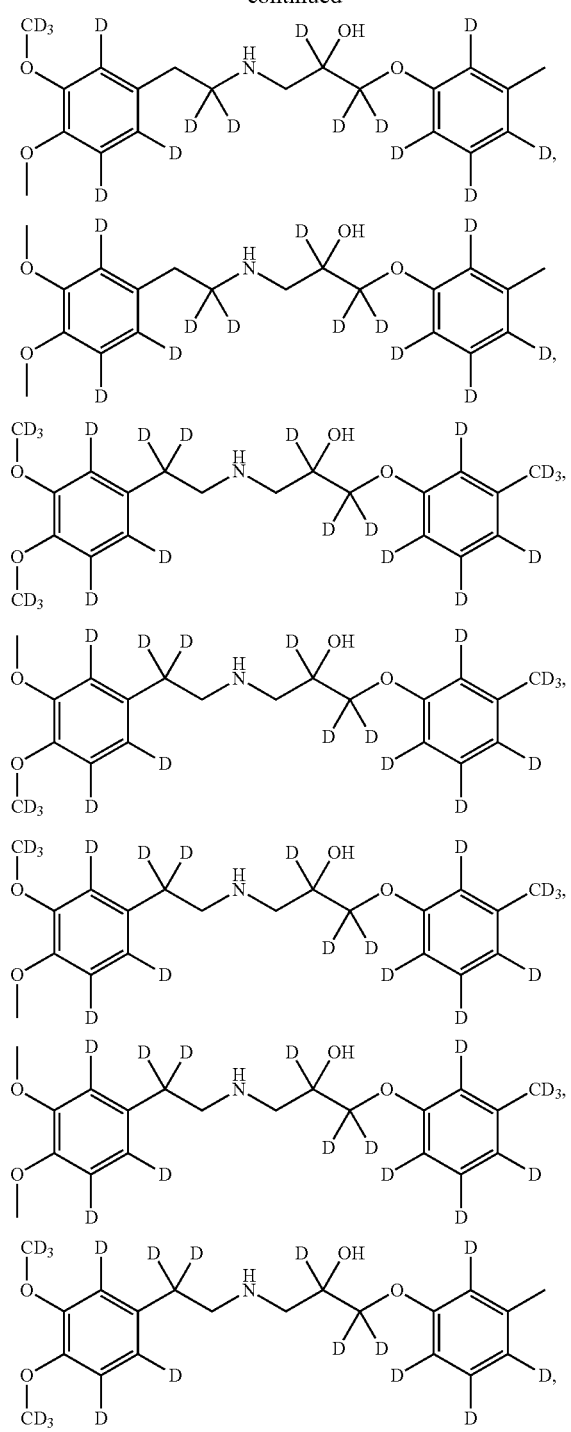
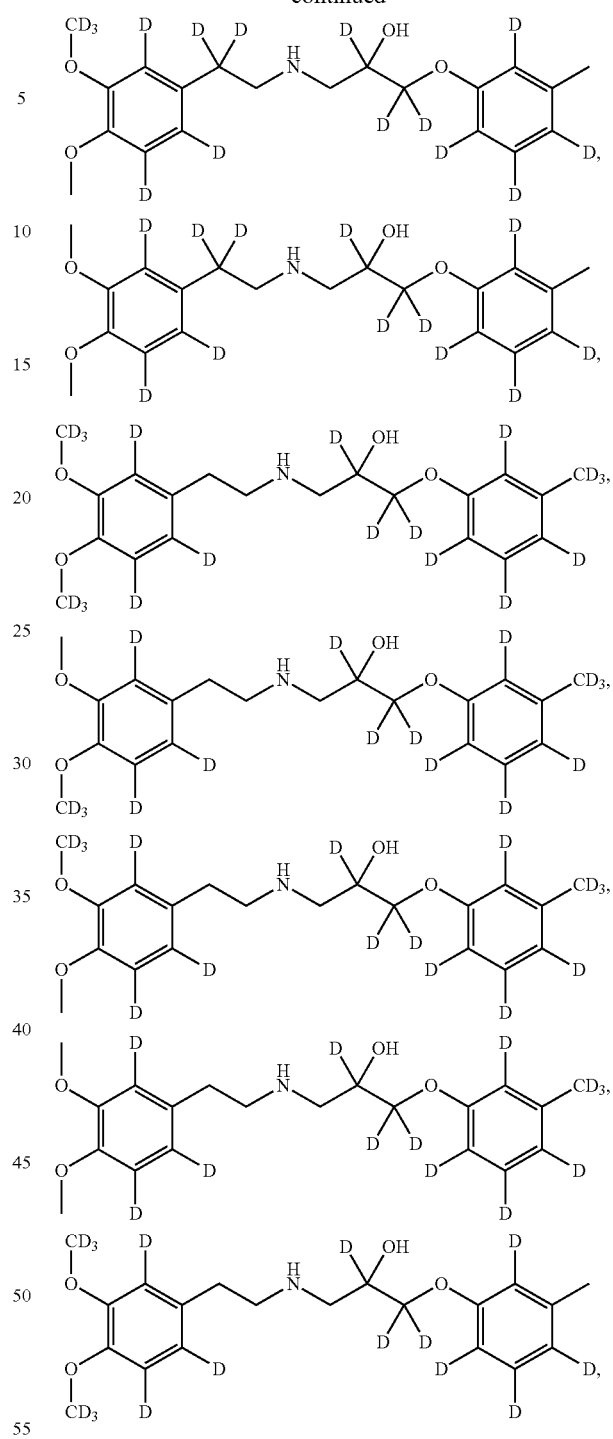
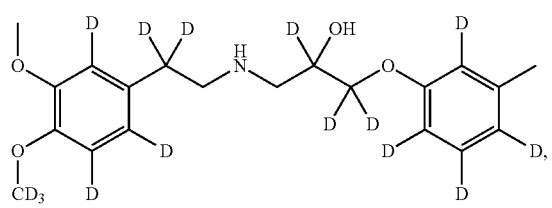
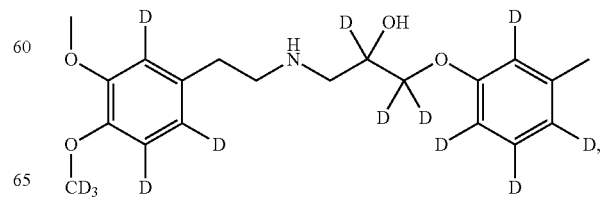

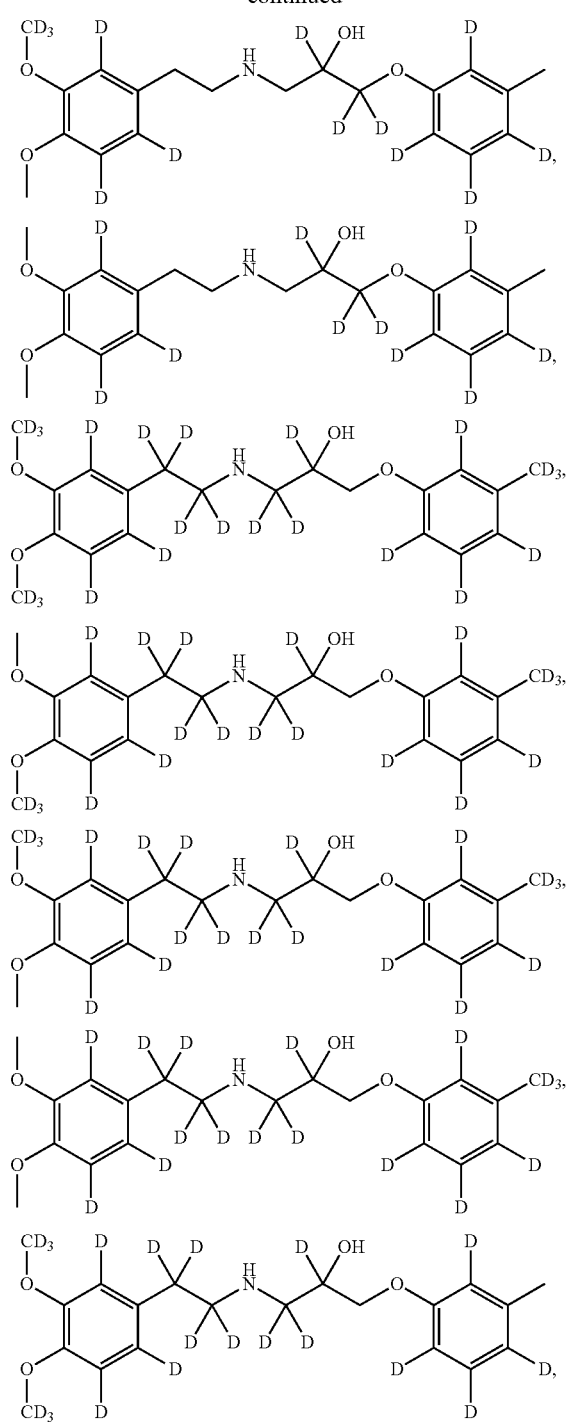
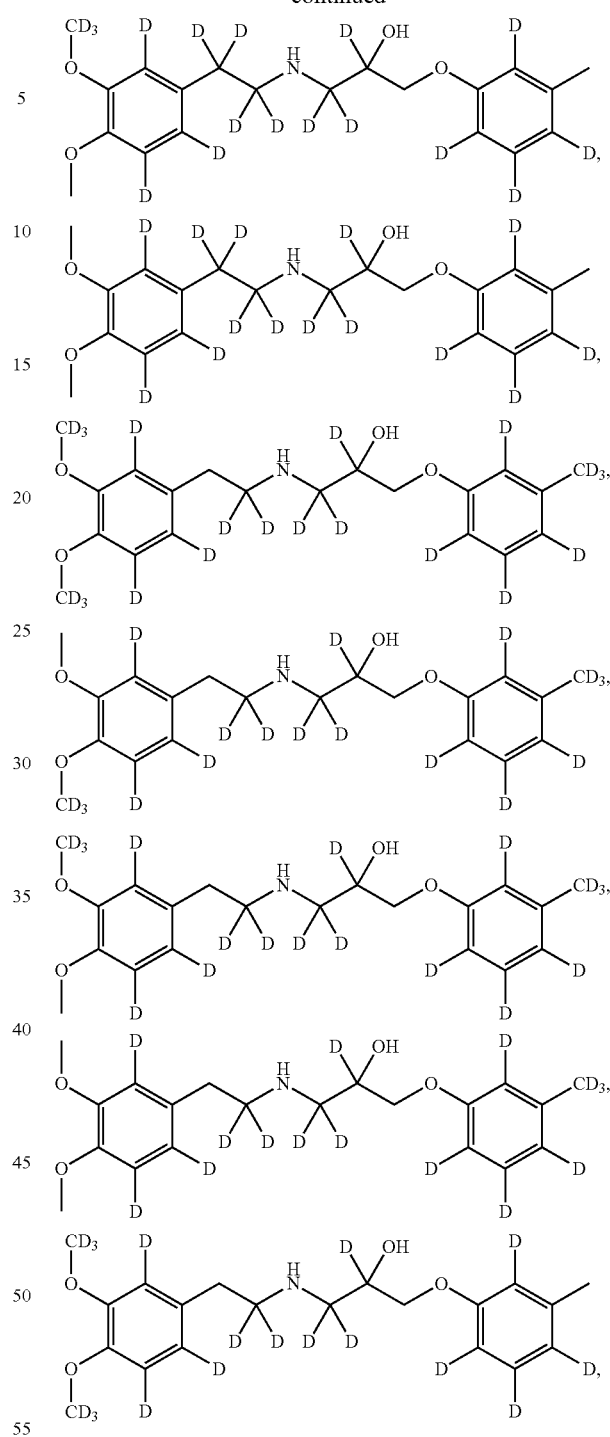
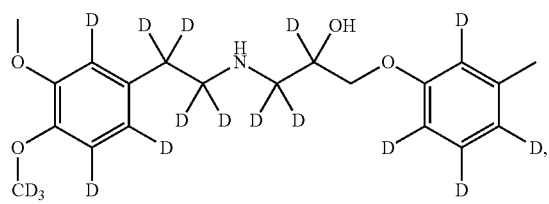

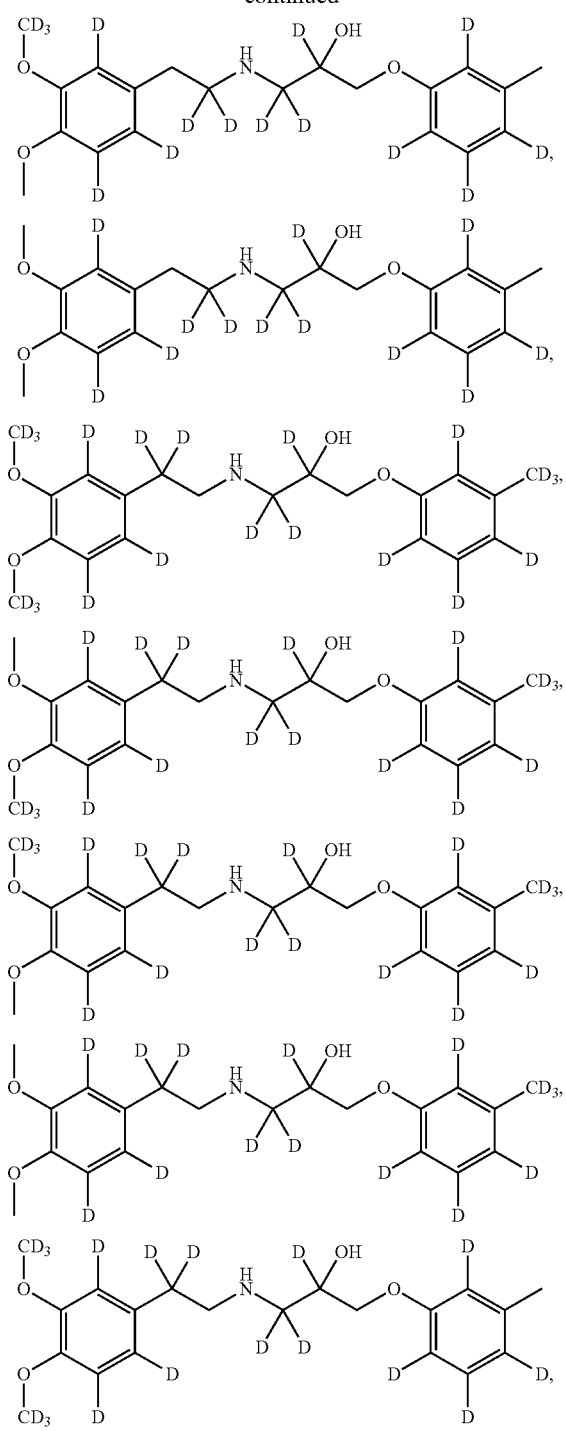
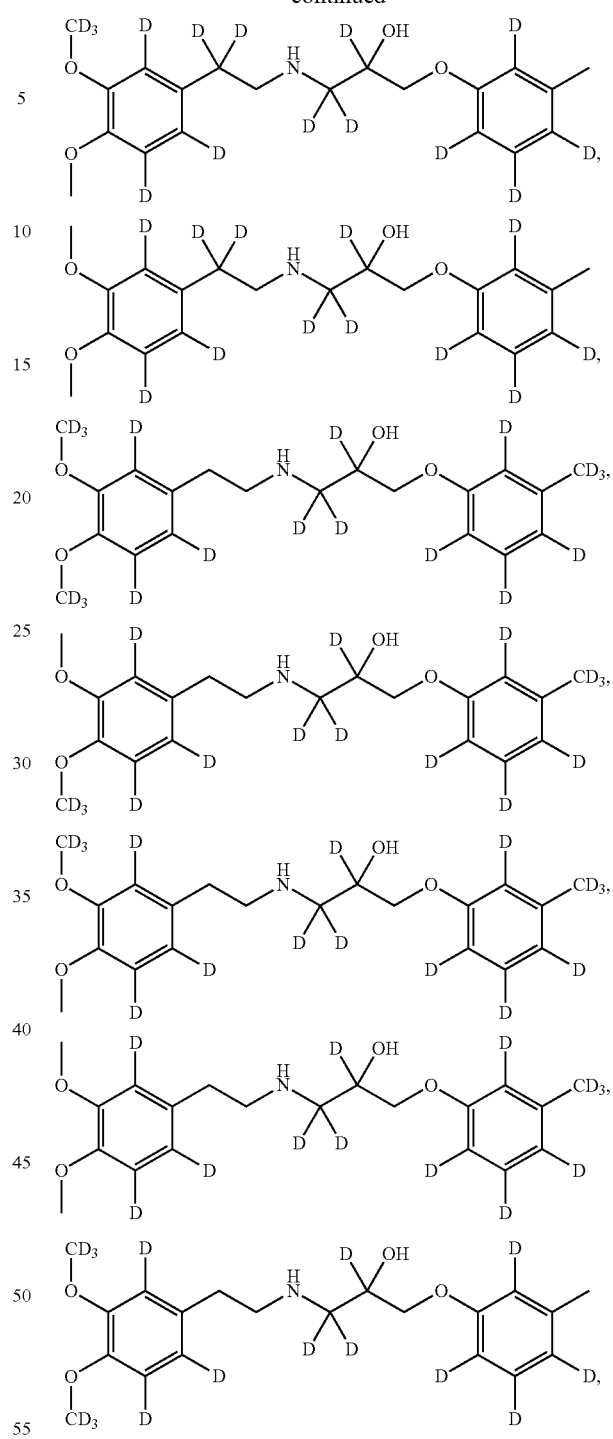
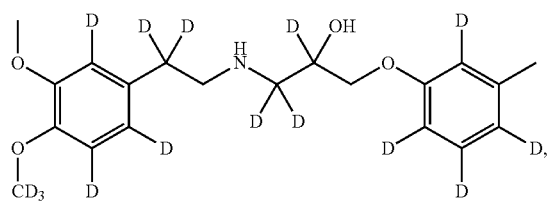
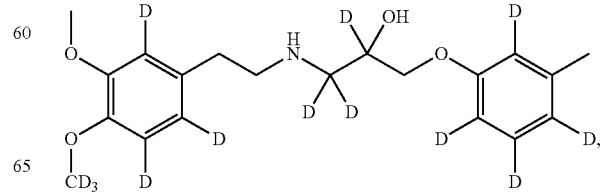

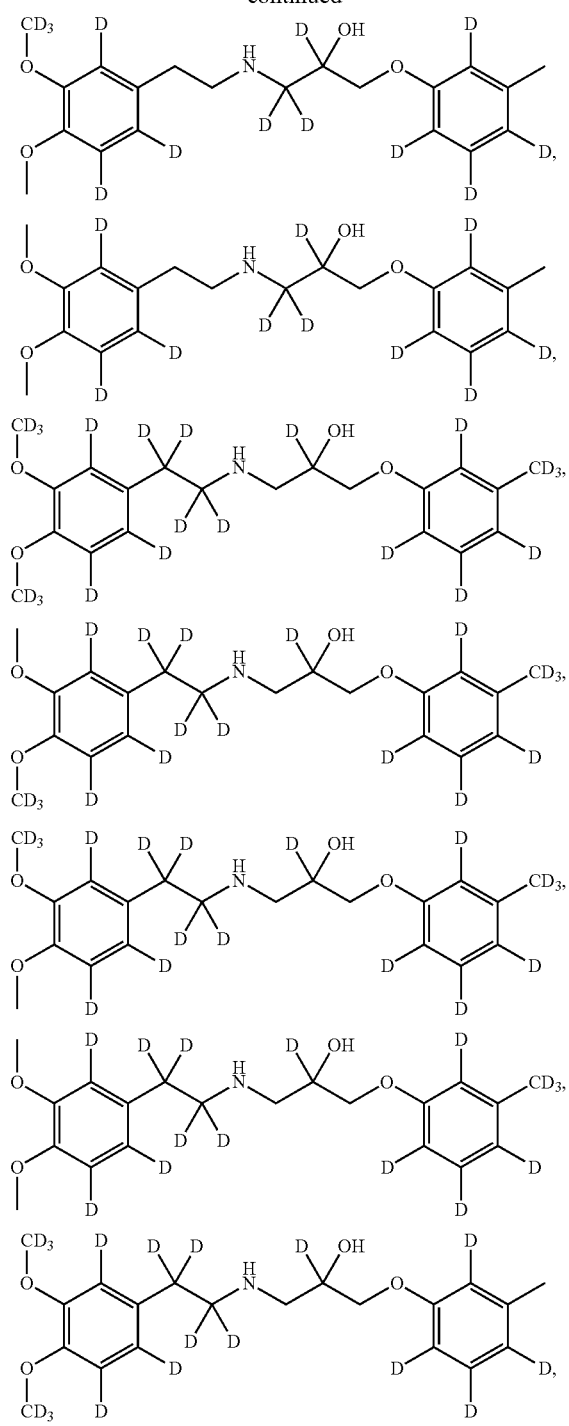
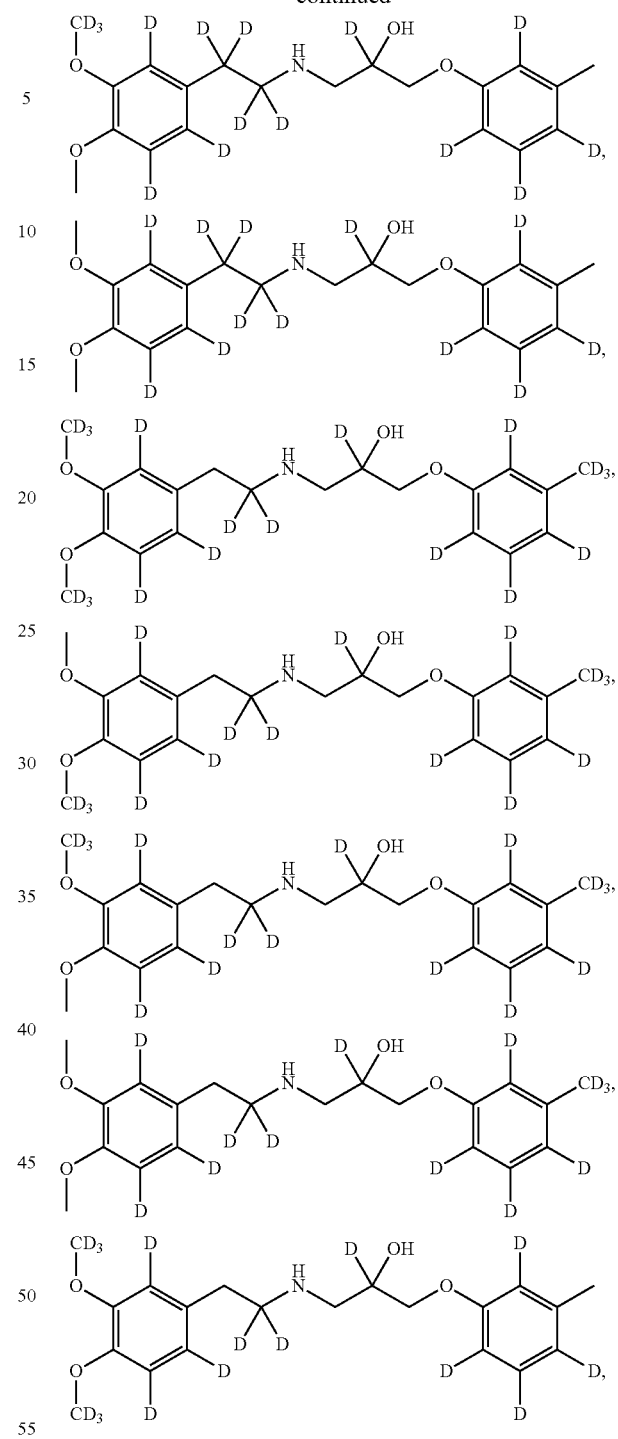
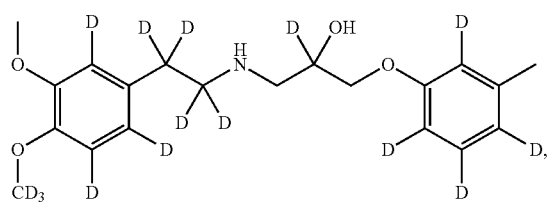
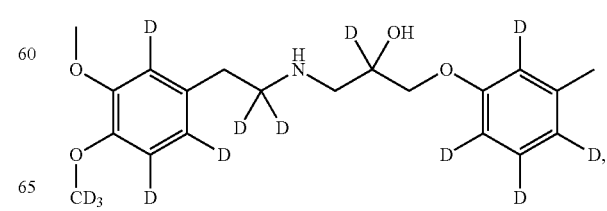

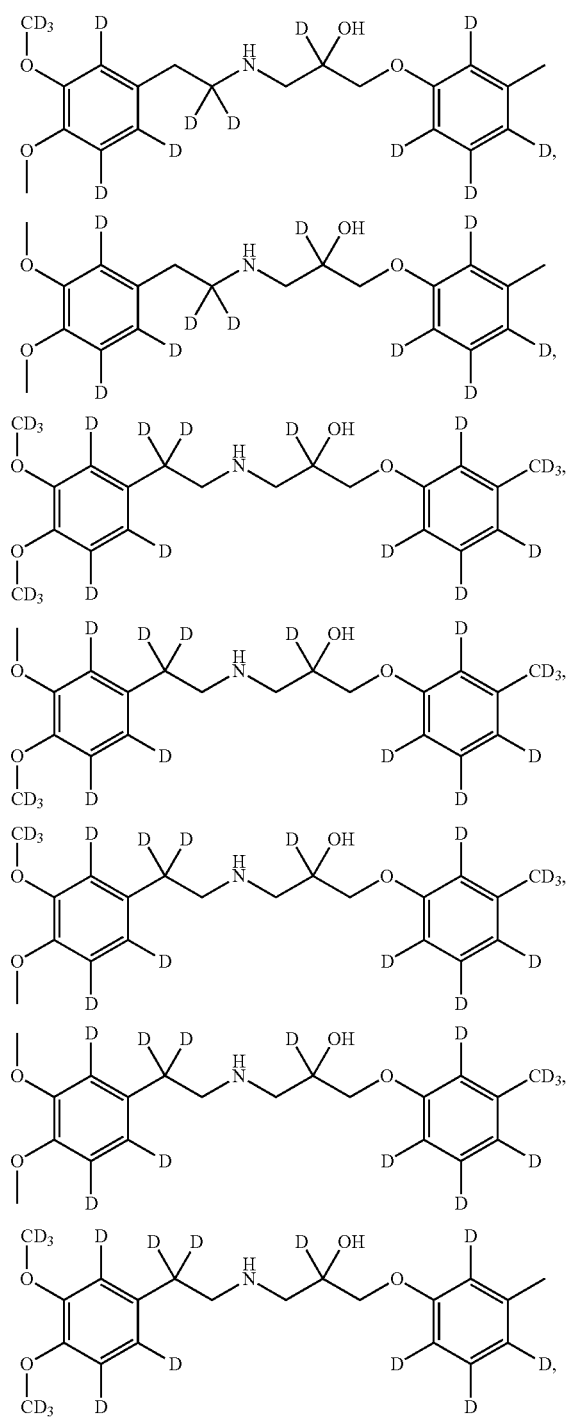
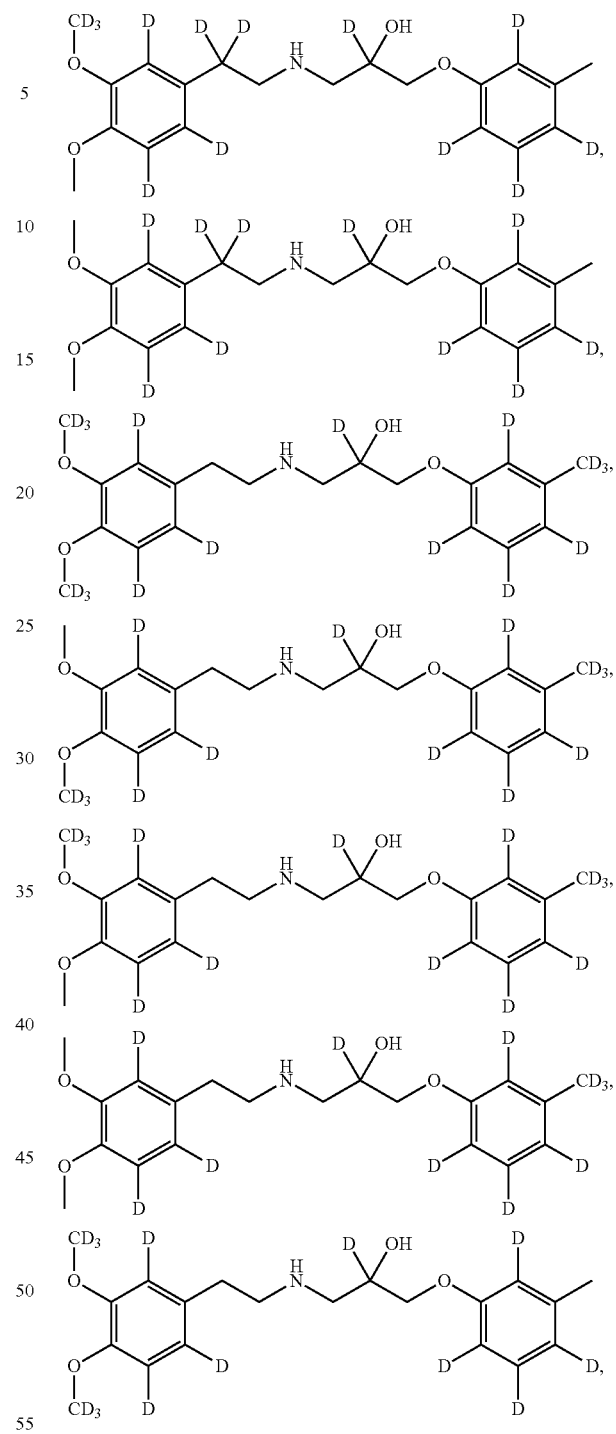

51
-continued
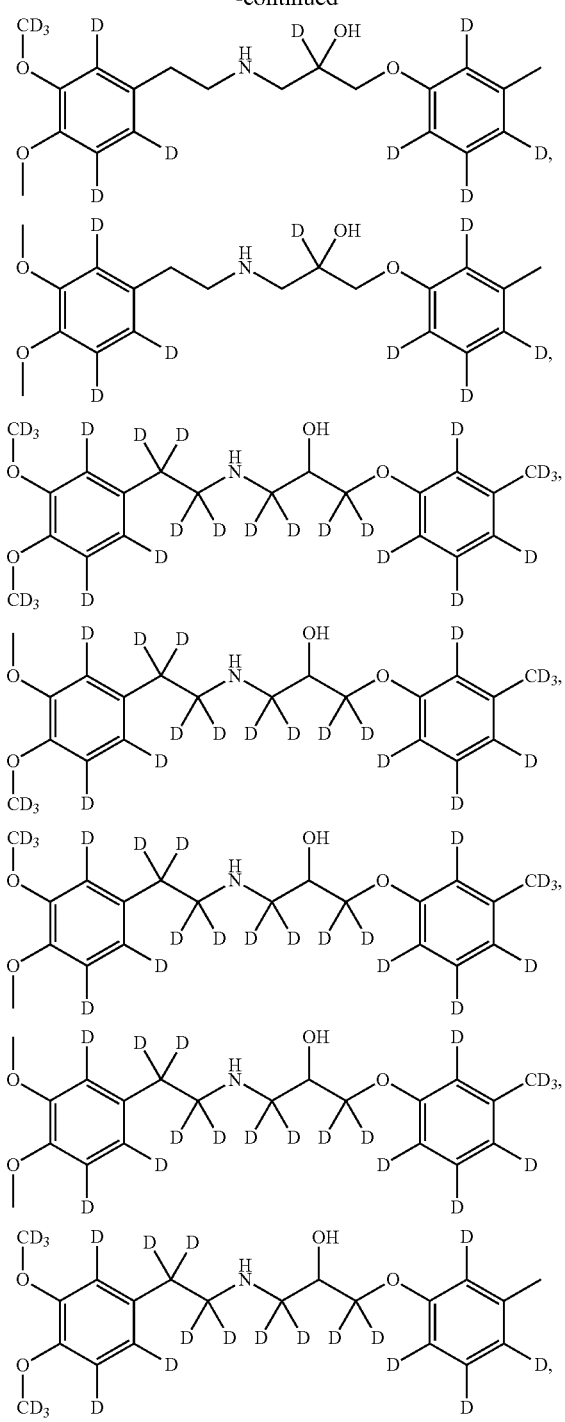
52
-continued
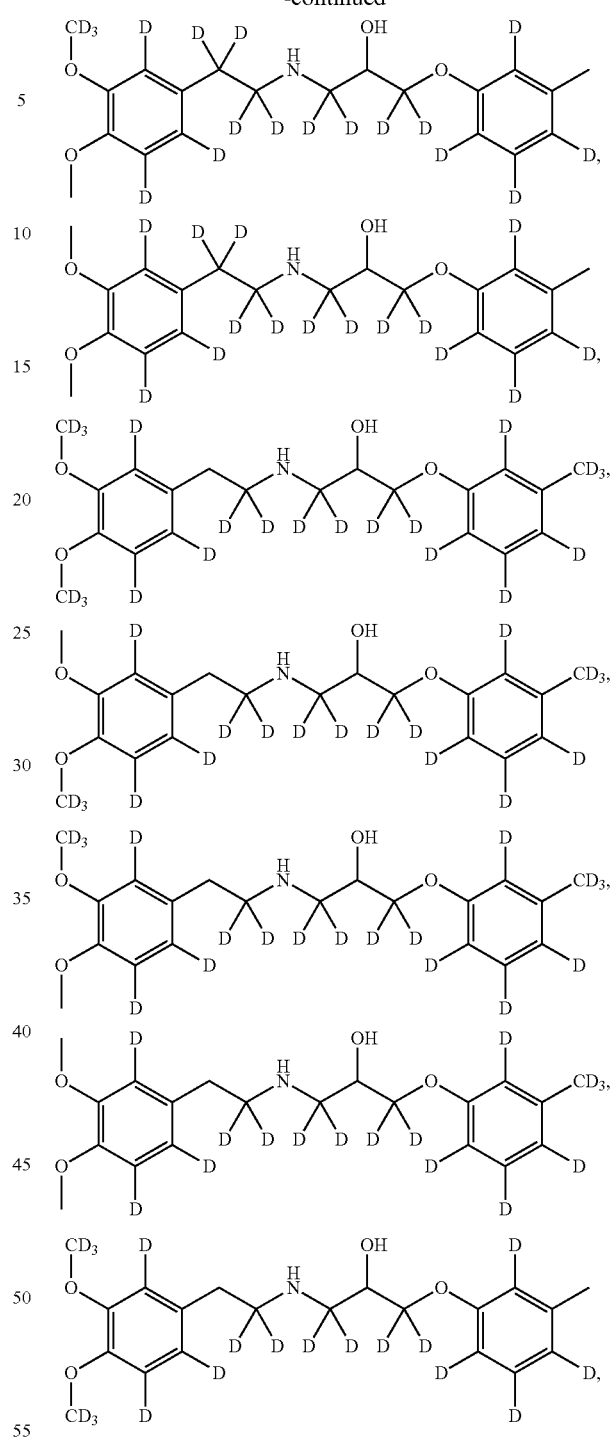
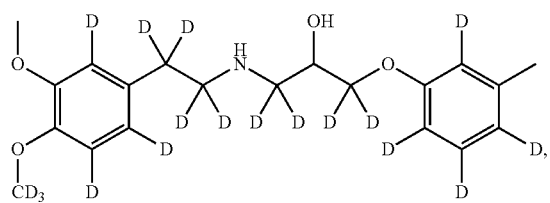
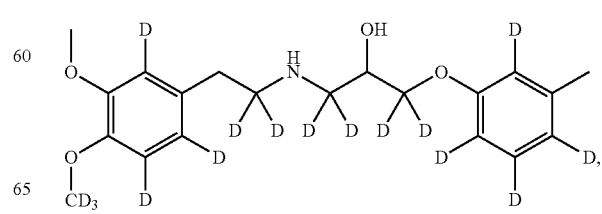

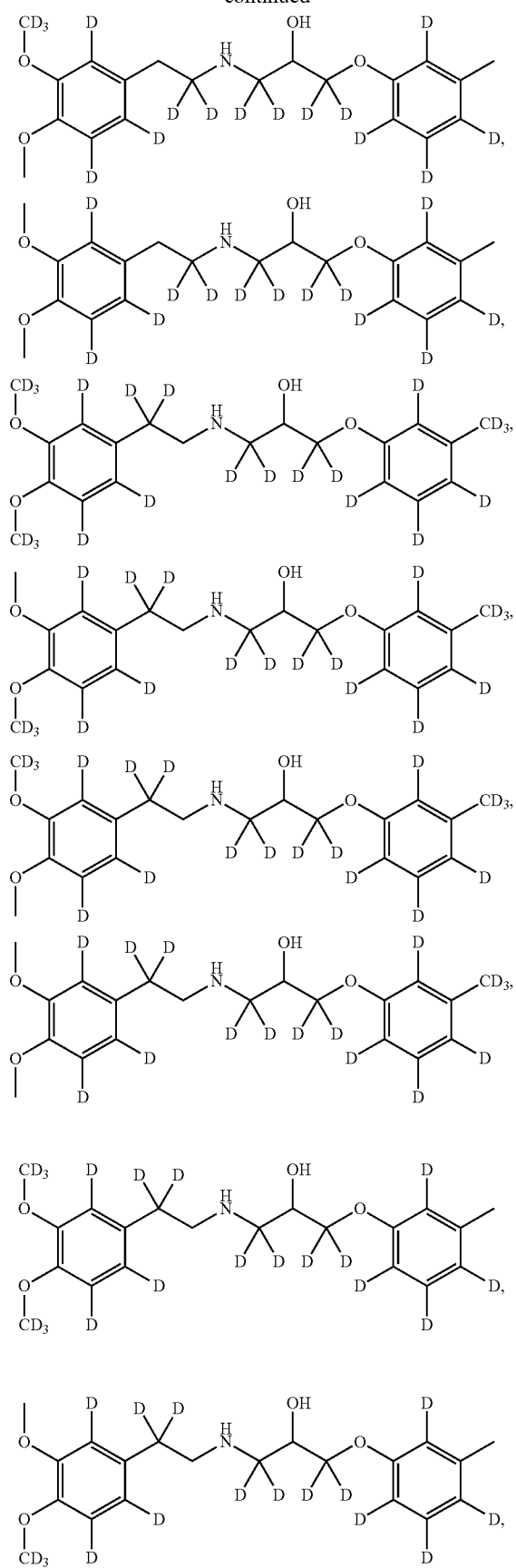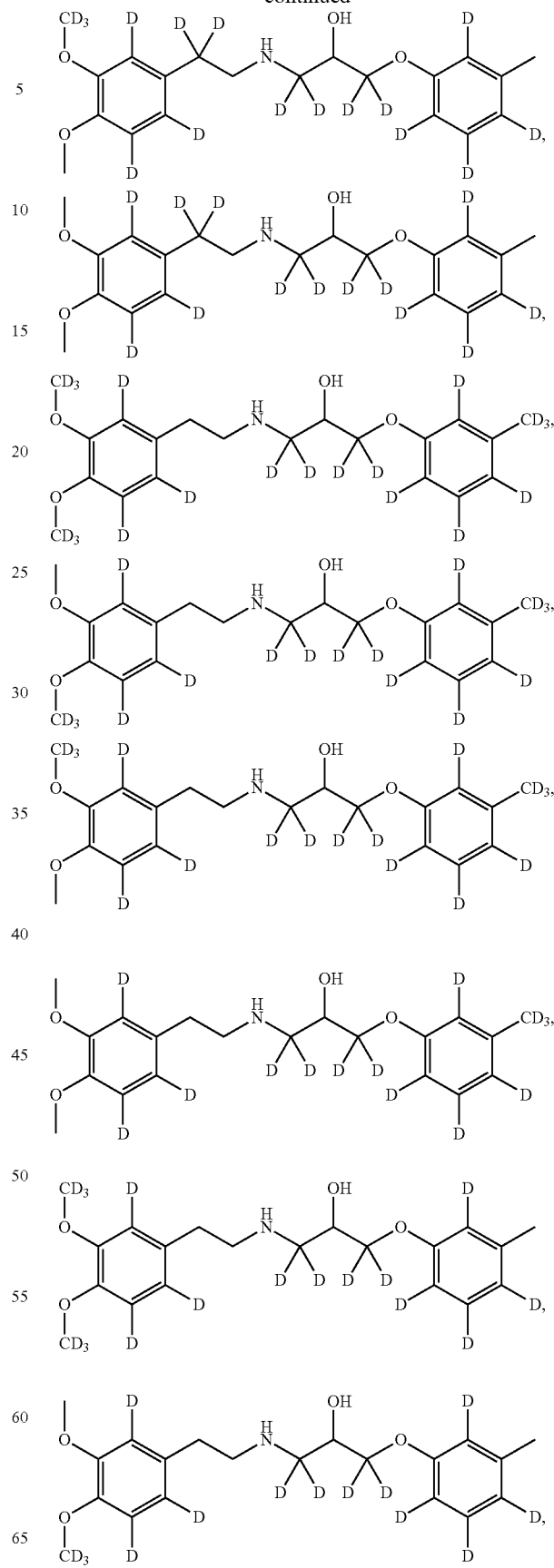

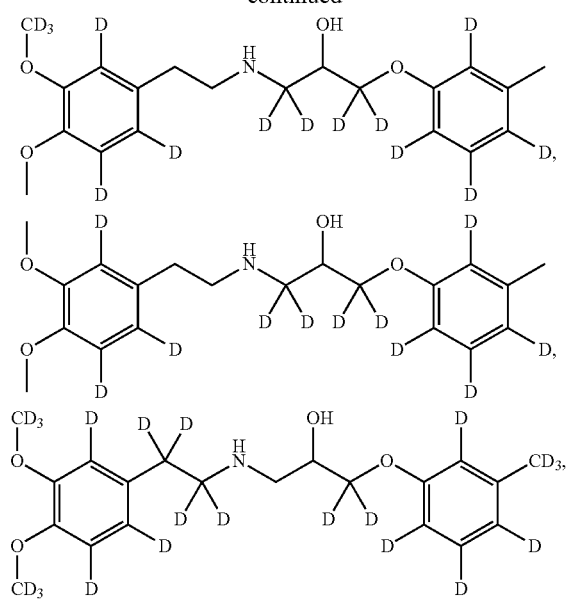
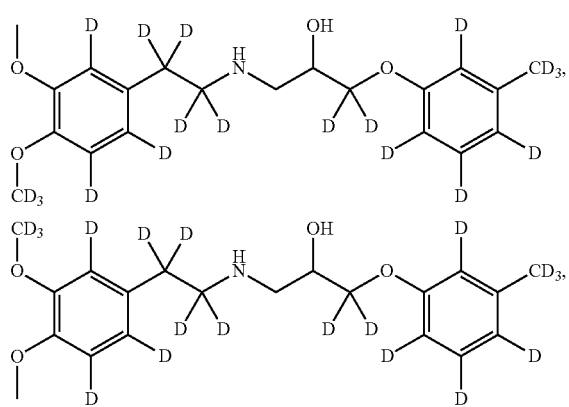
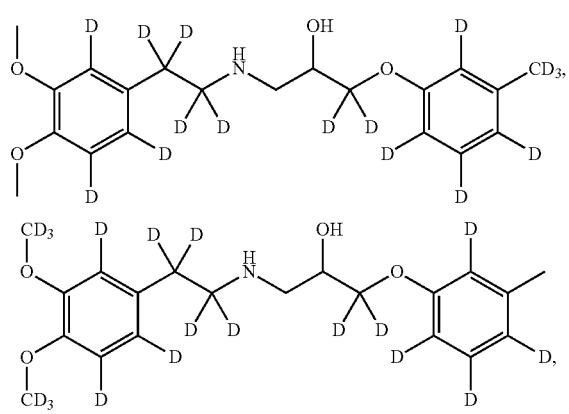
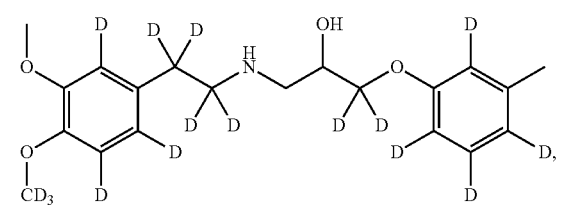
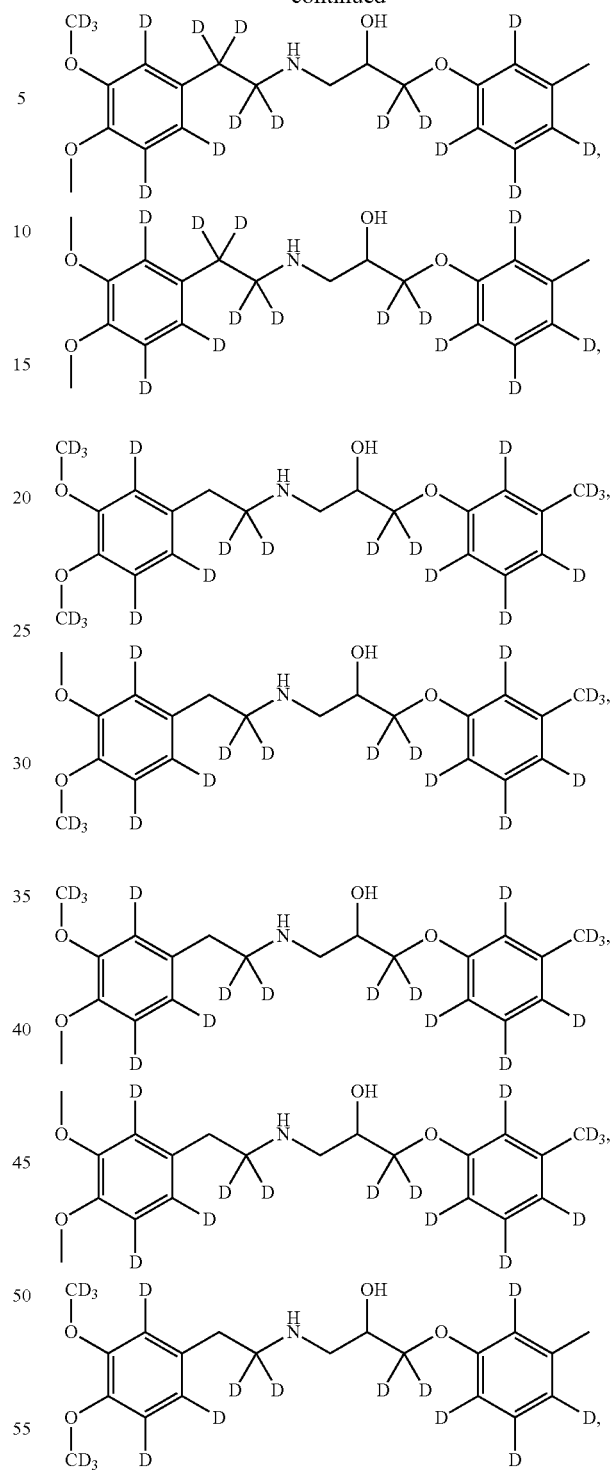
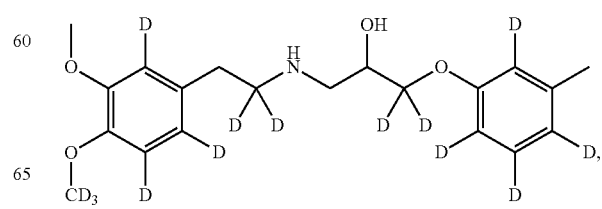

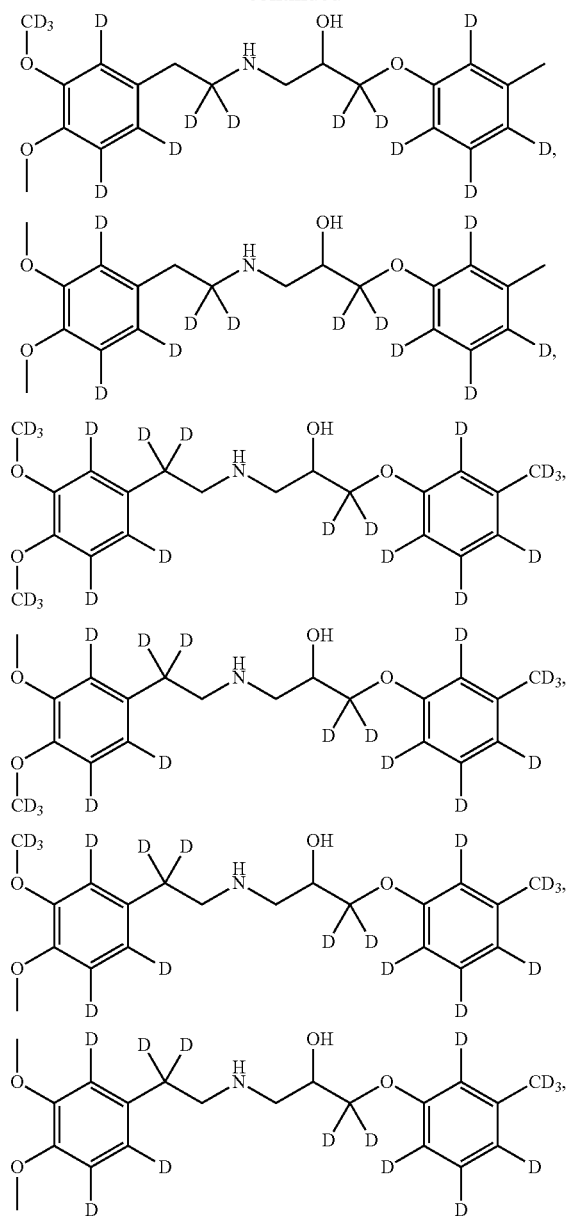
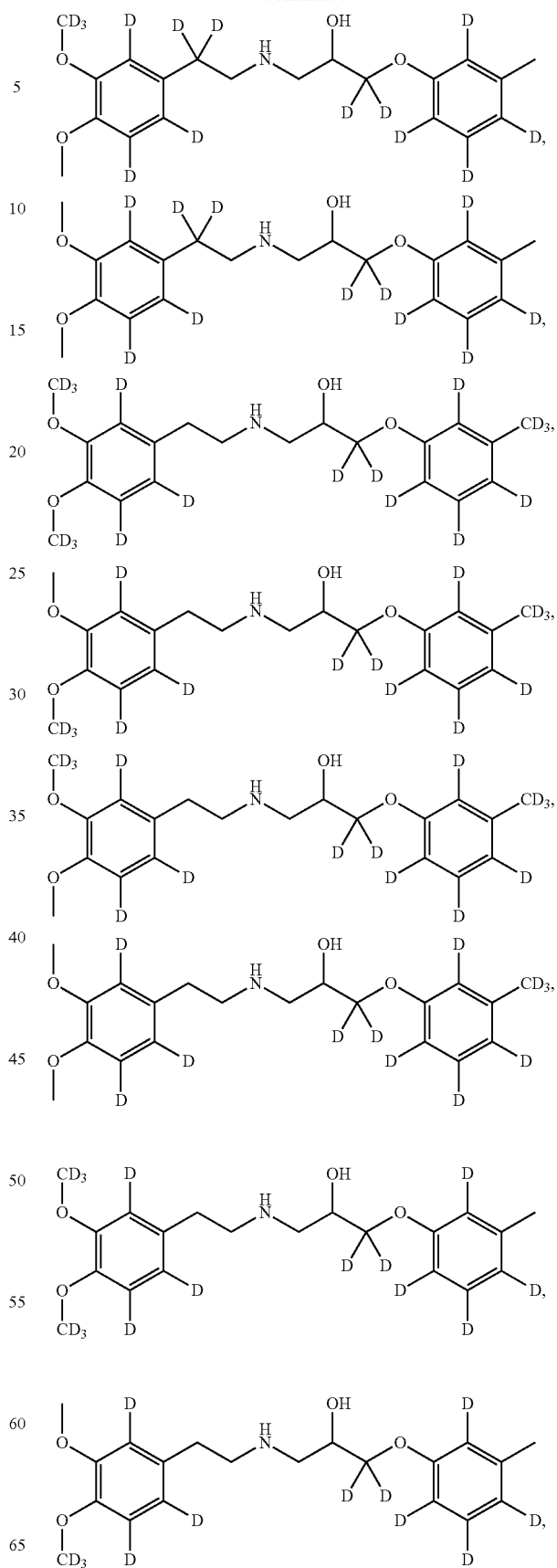

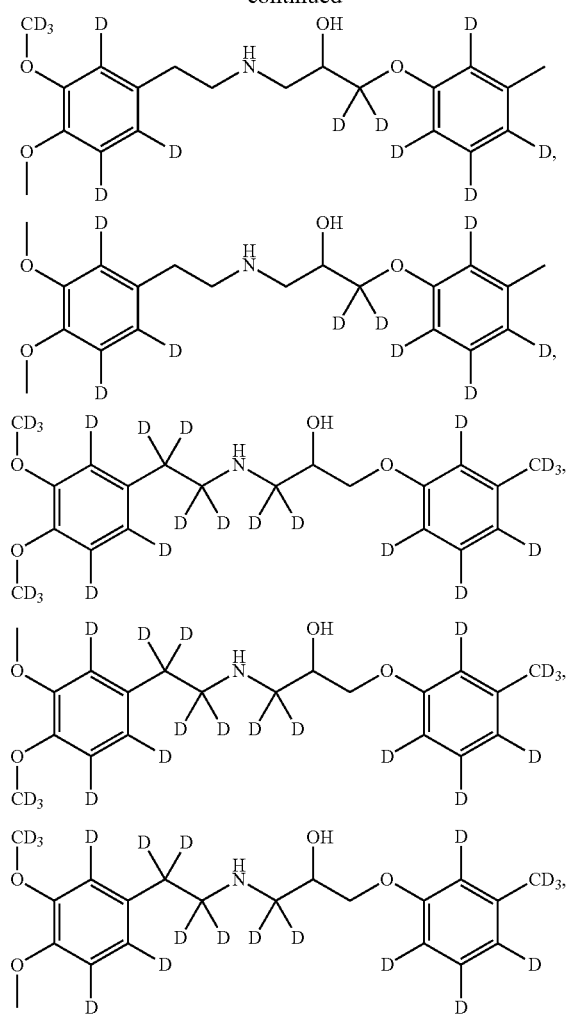
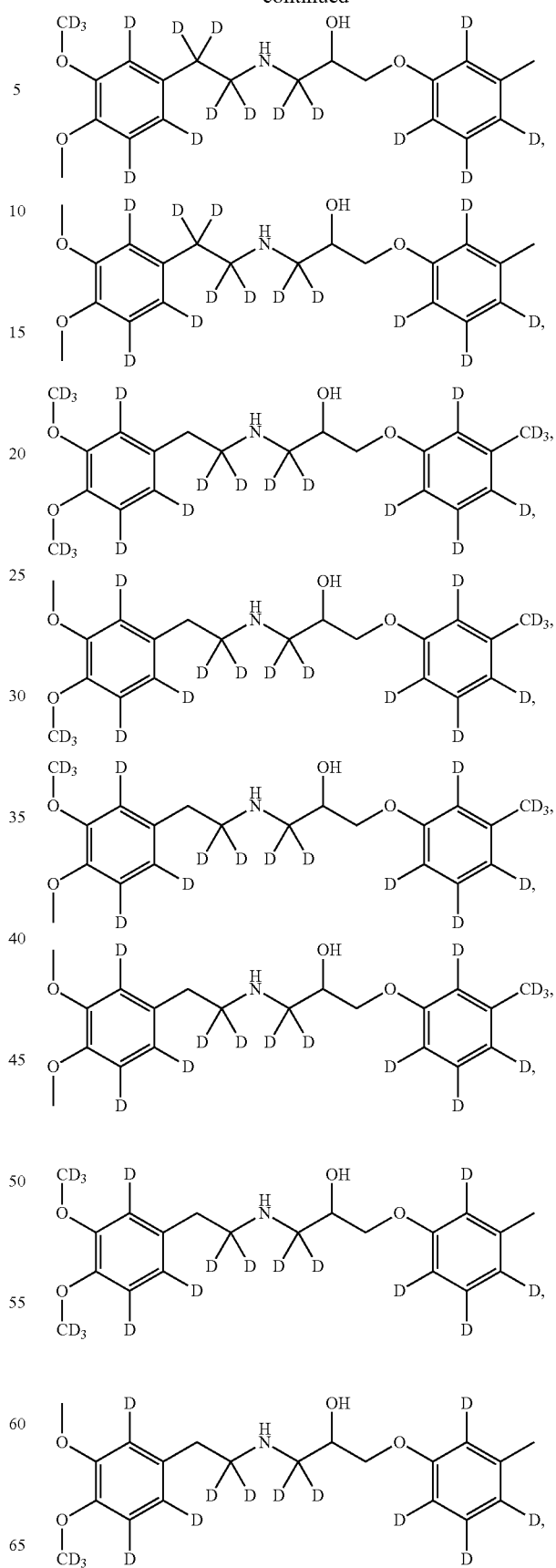

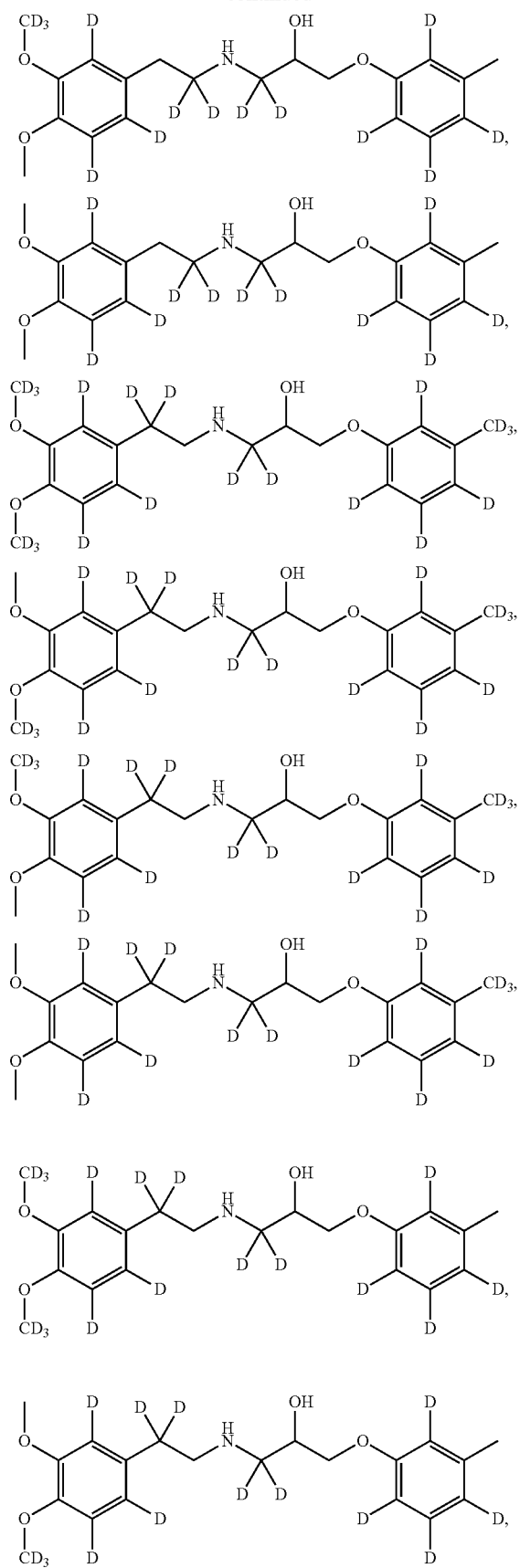
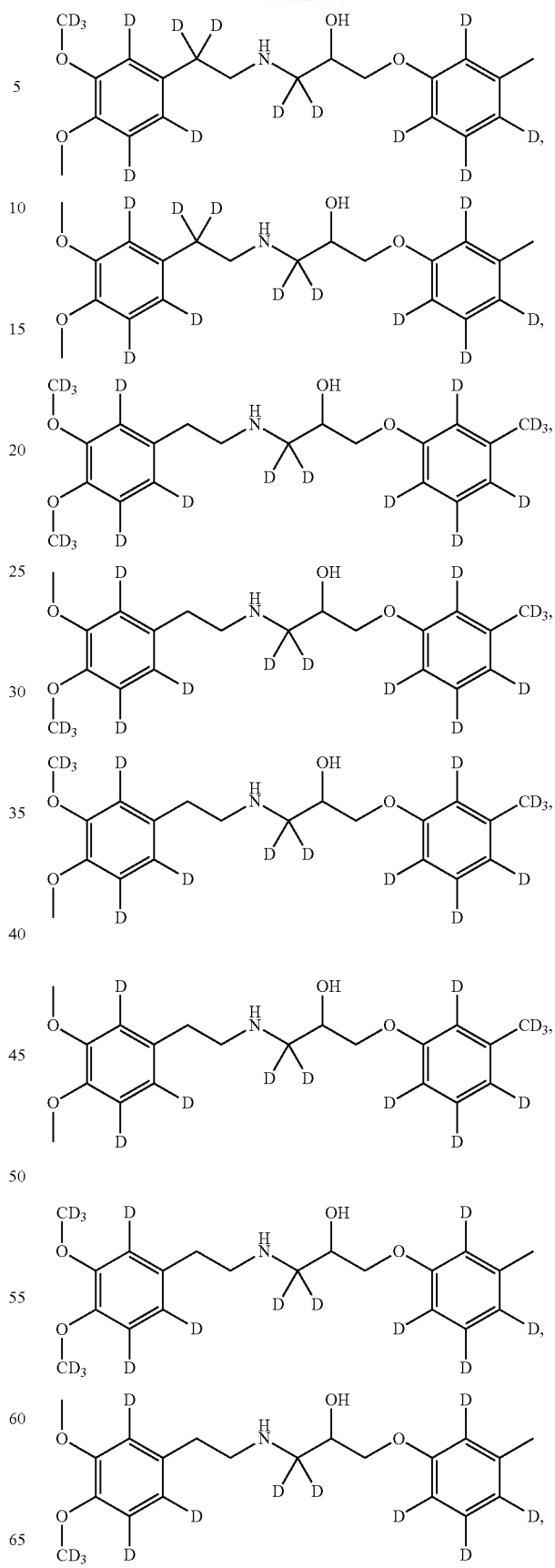

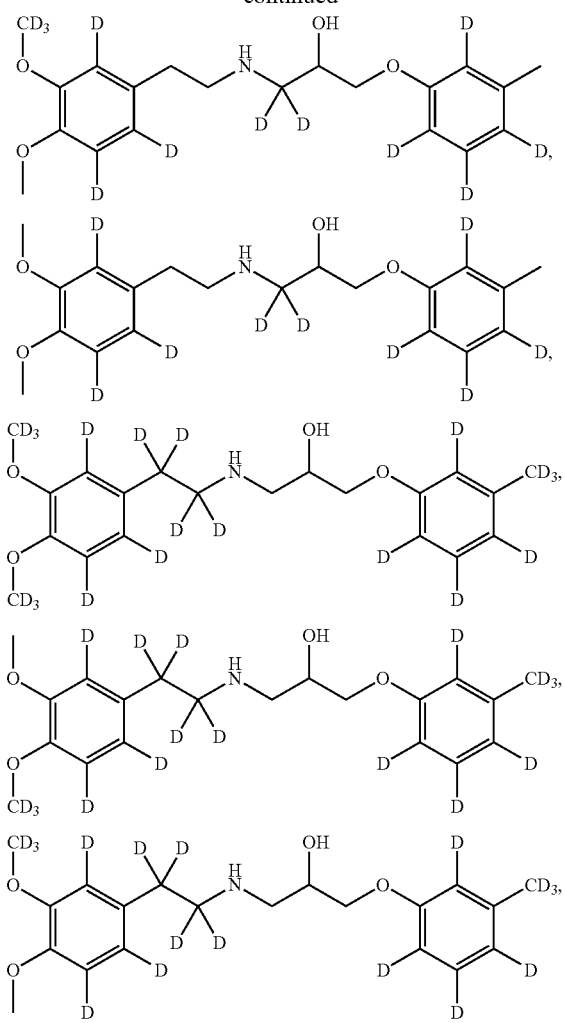
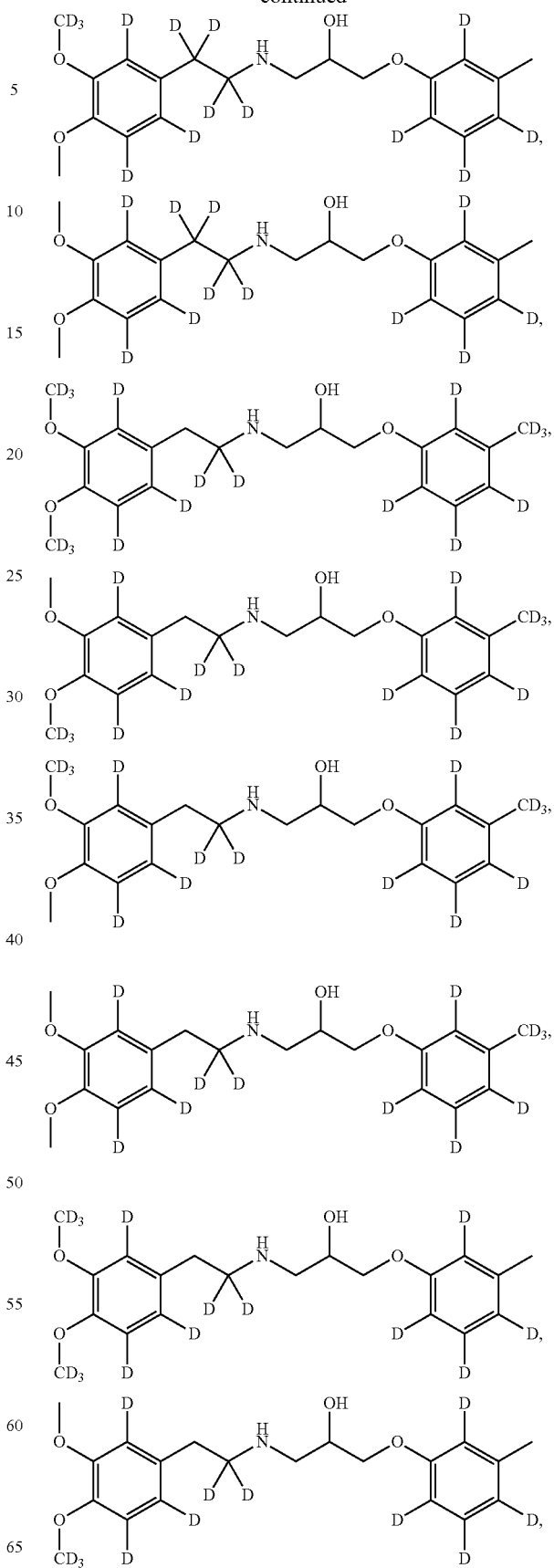

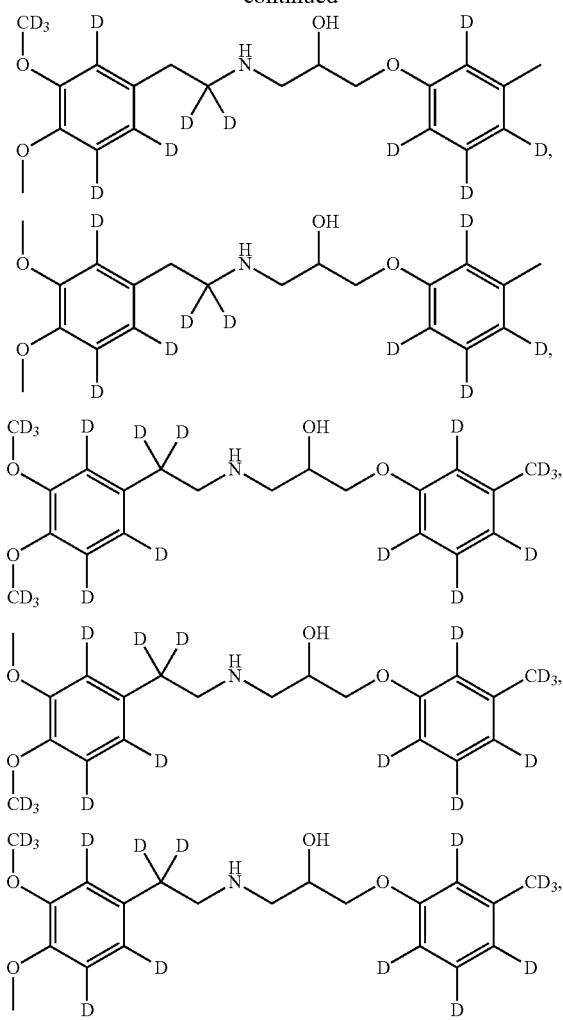
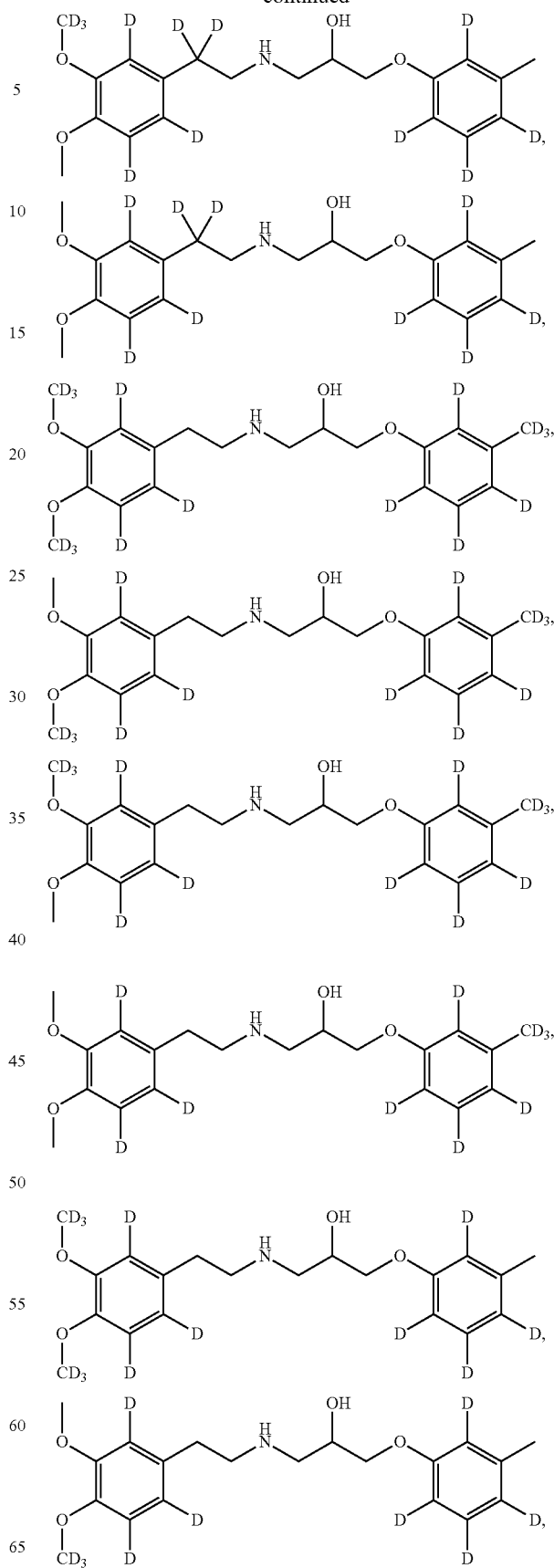

67
-continued
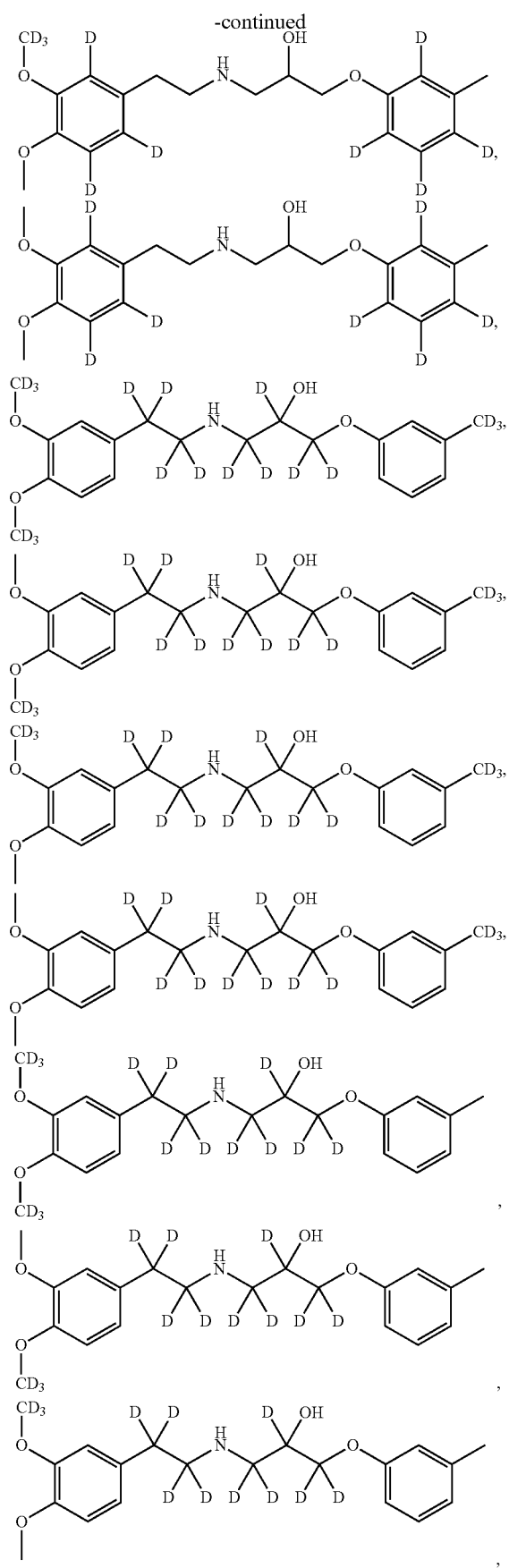
68
-continued
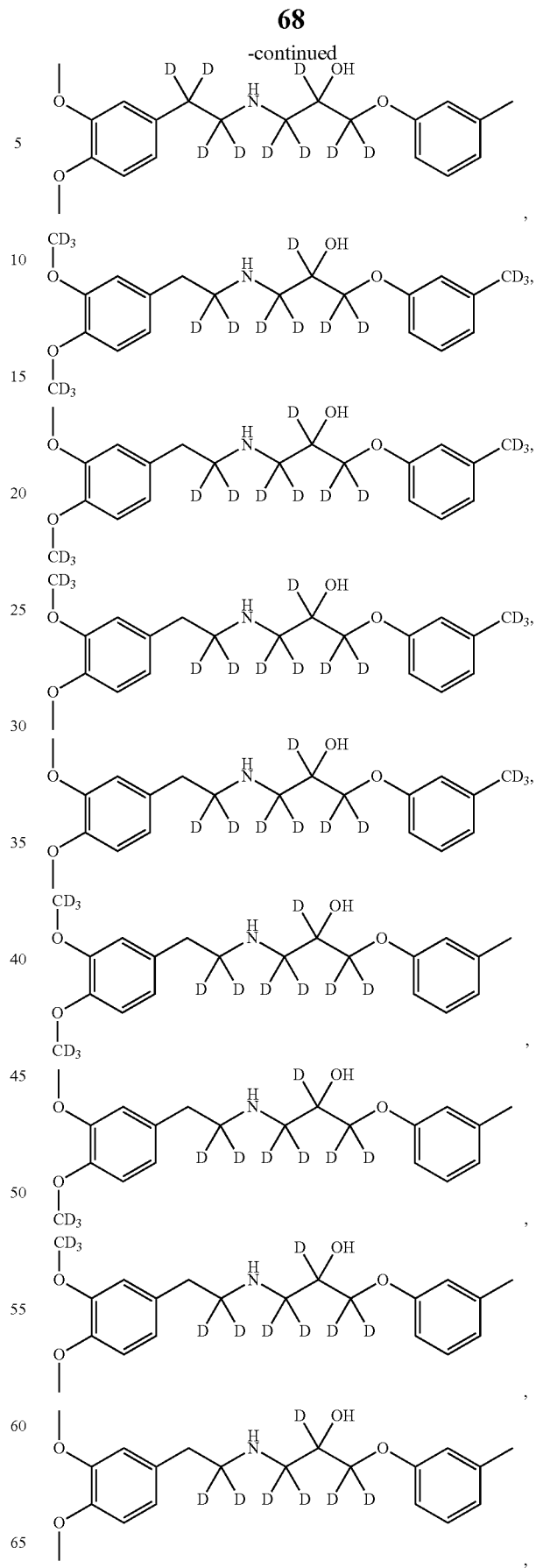

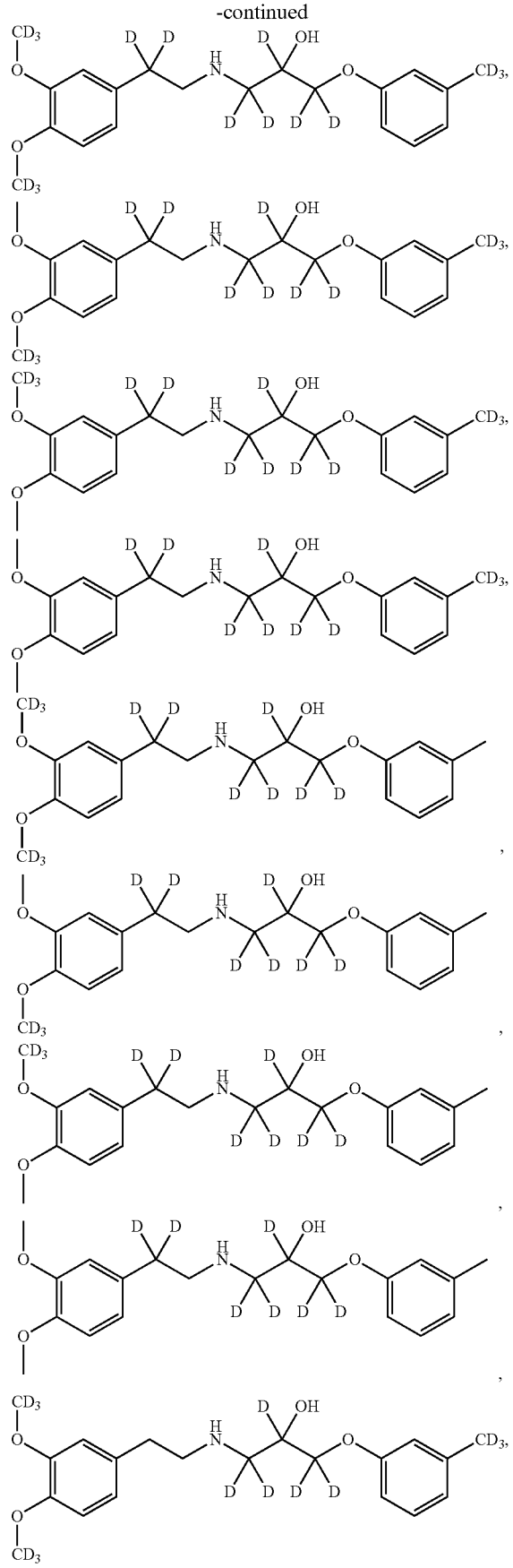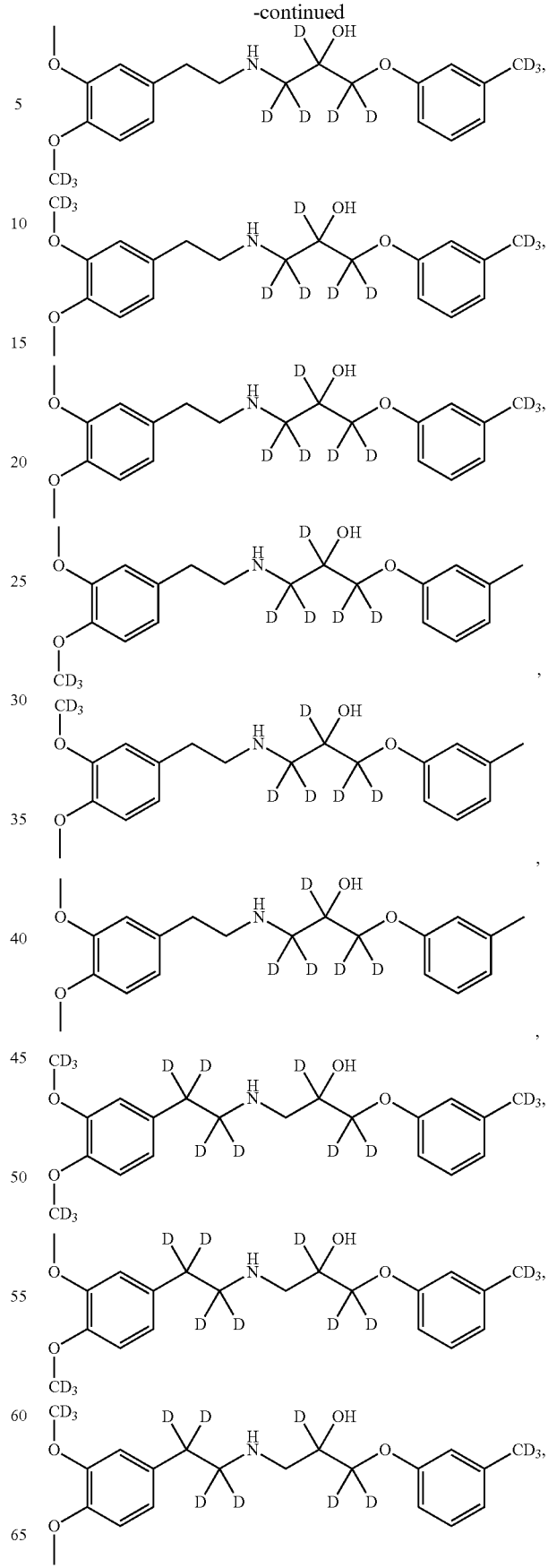

-continued
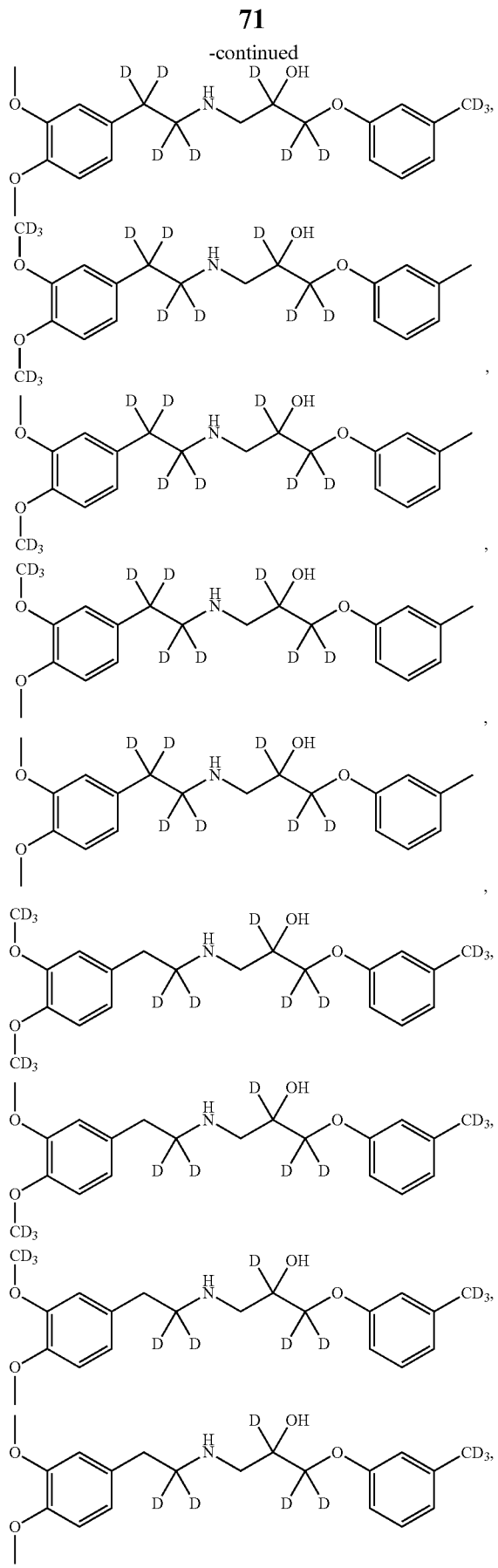
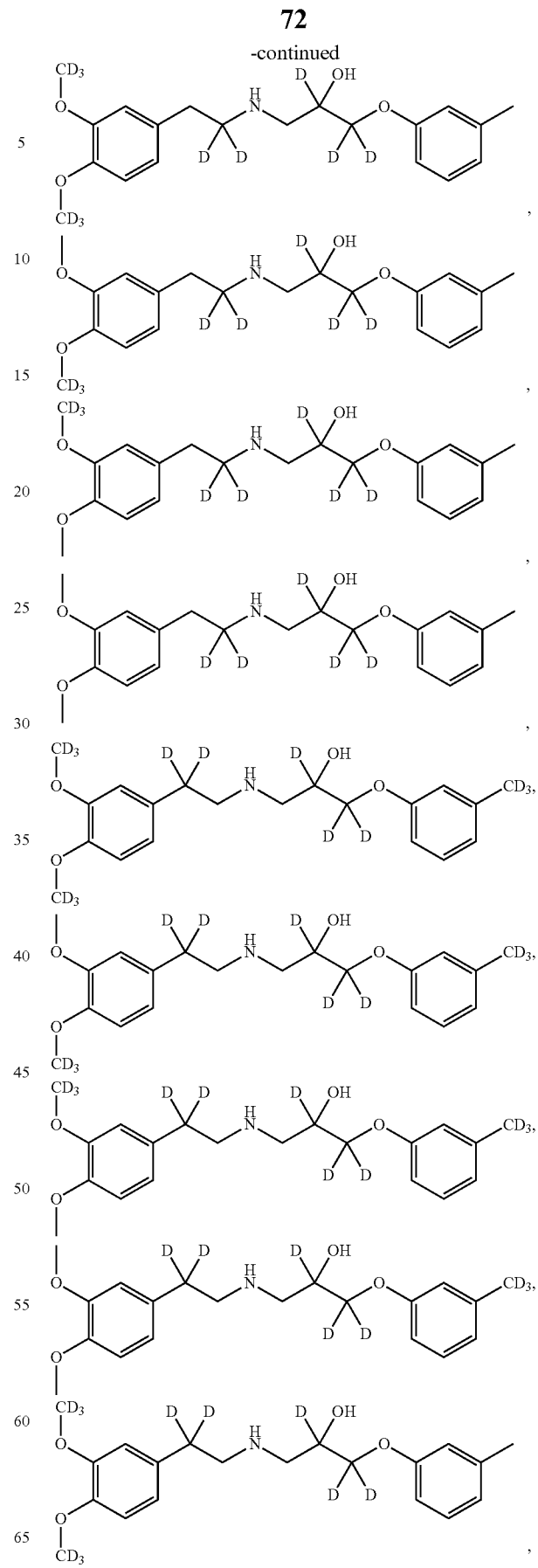

73 74

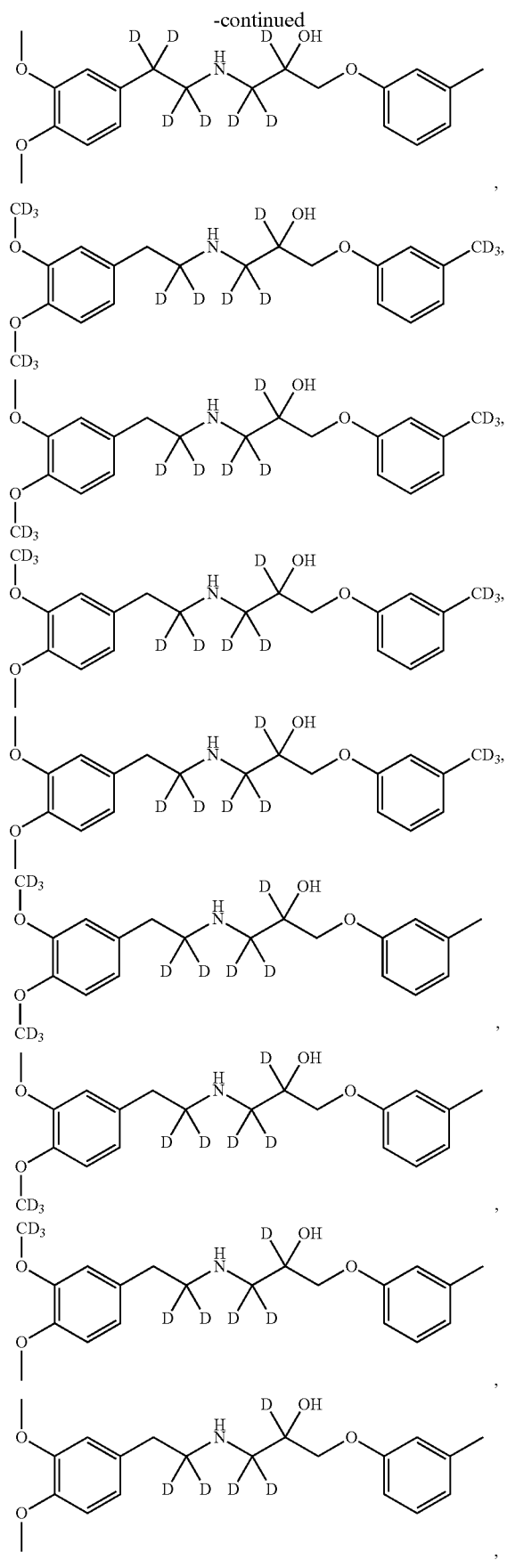
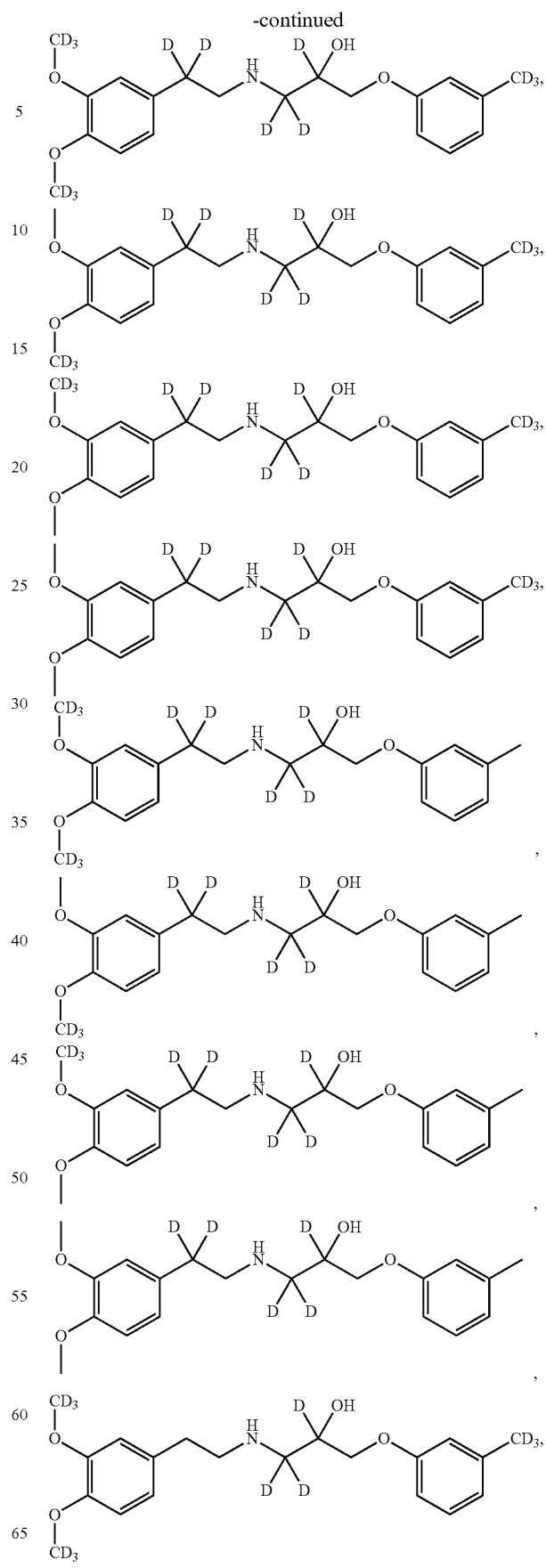

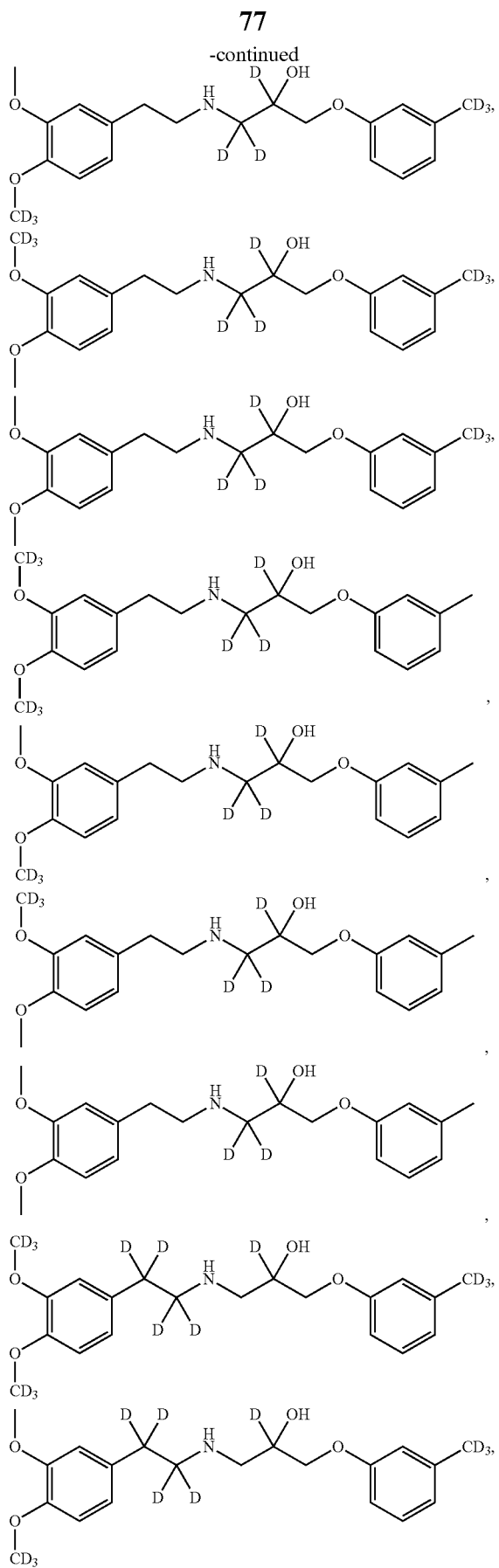
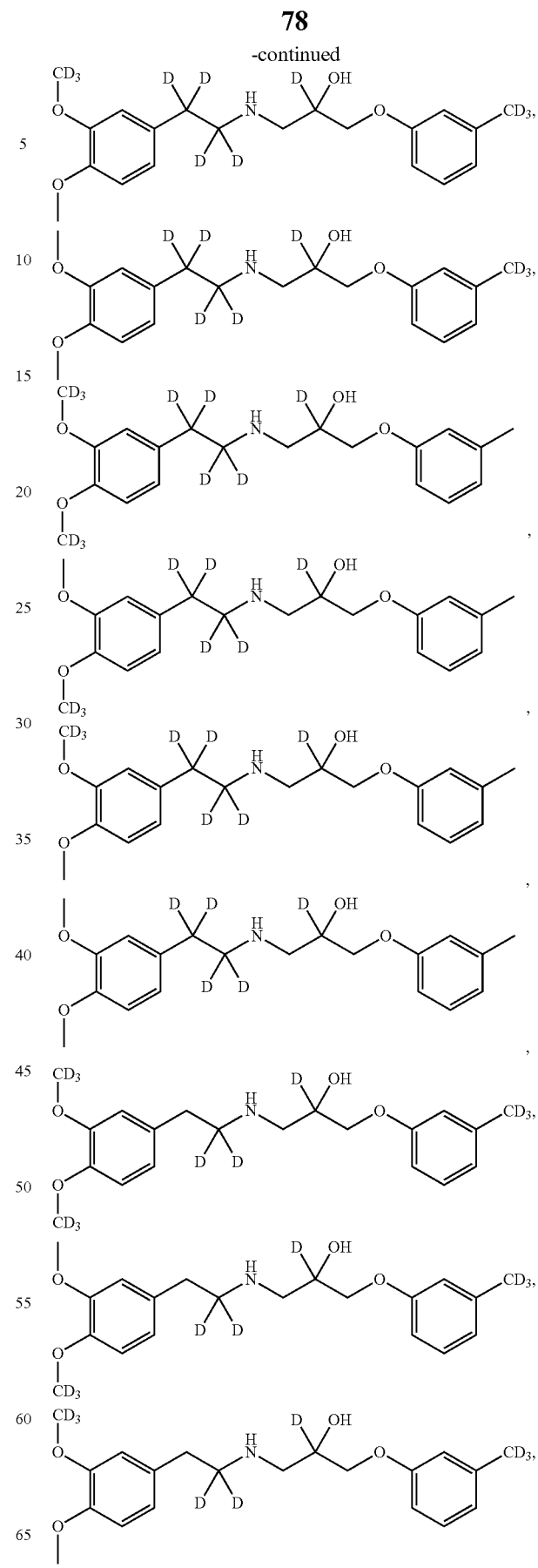

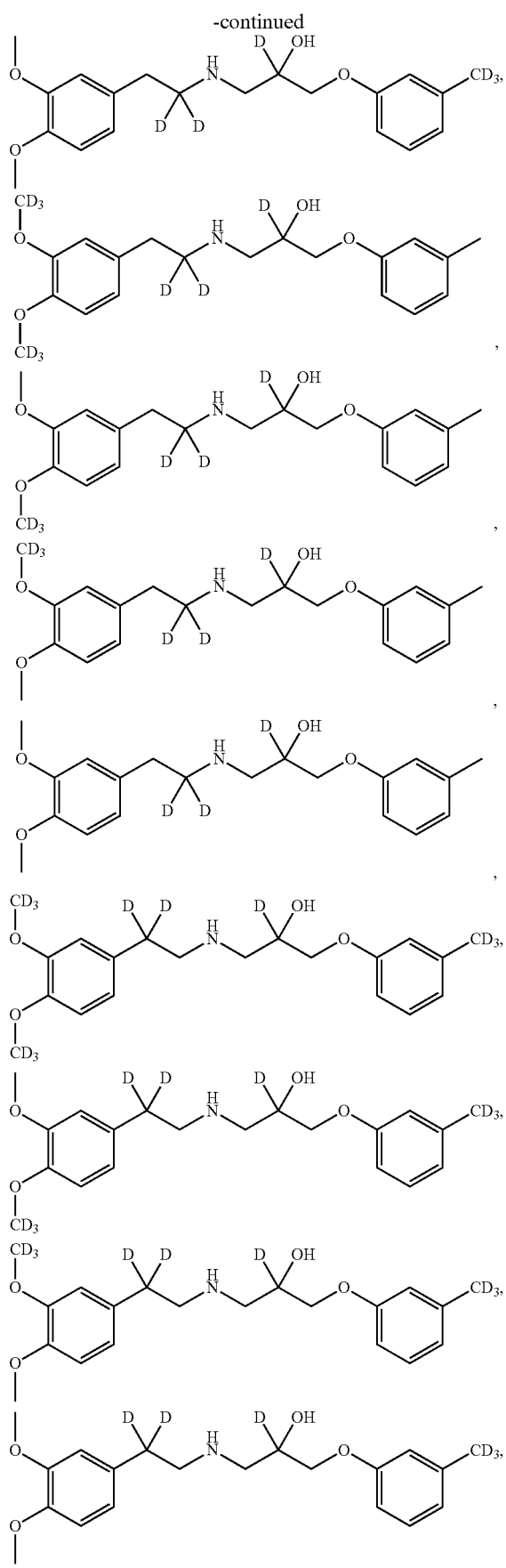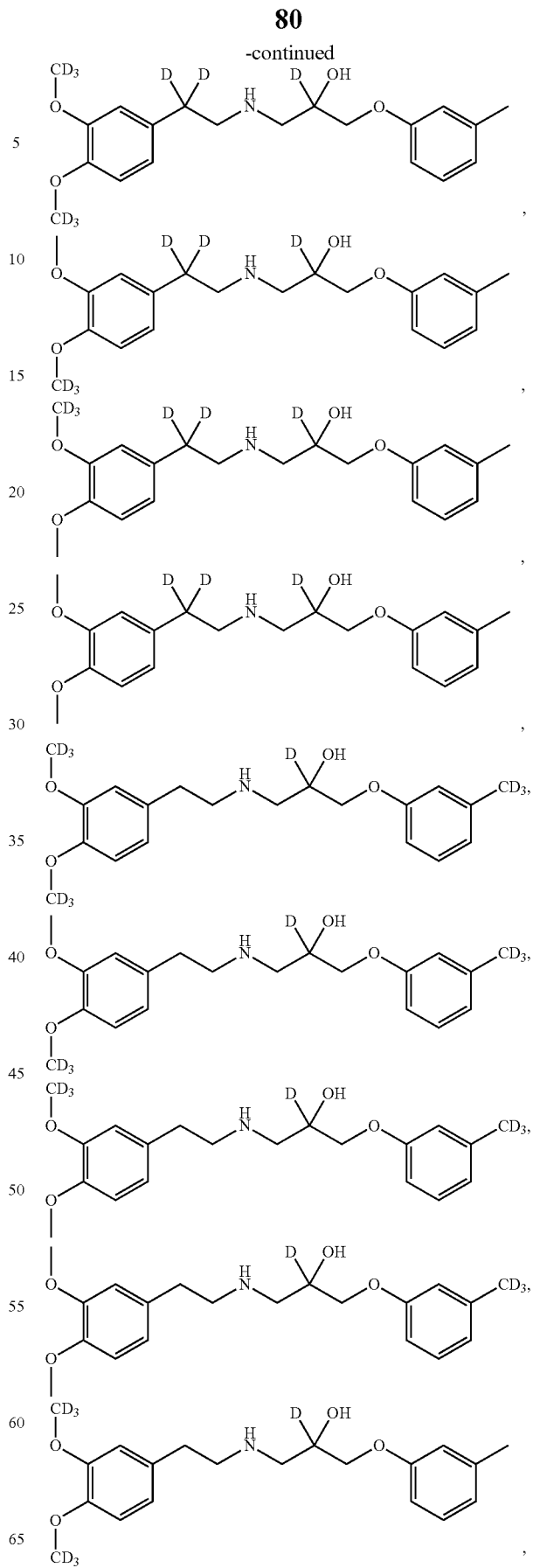

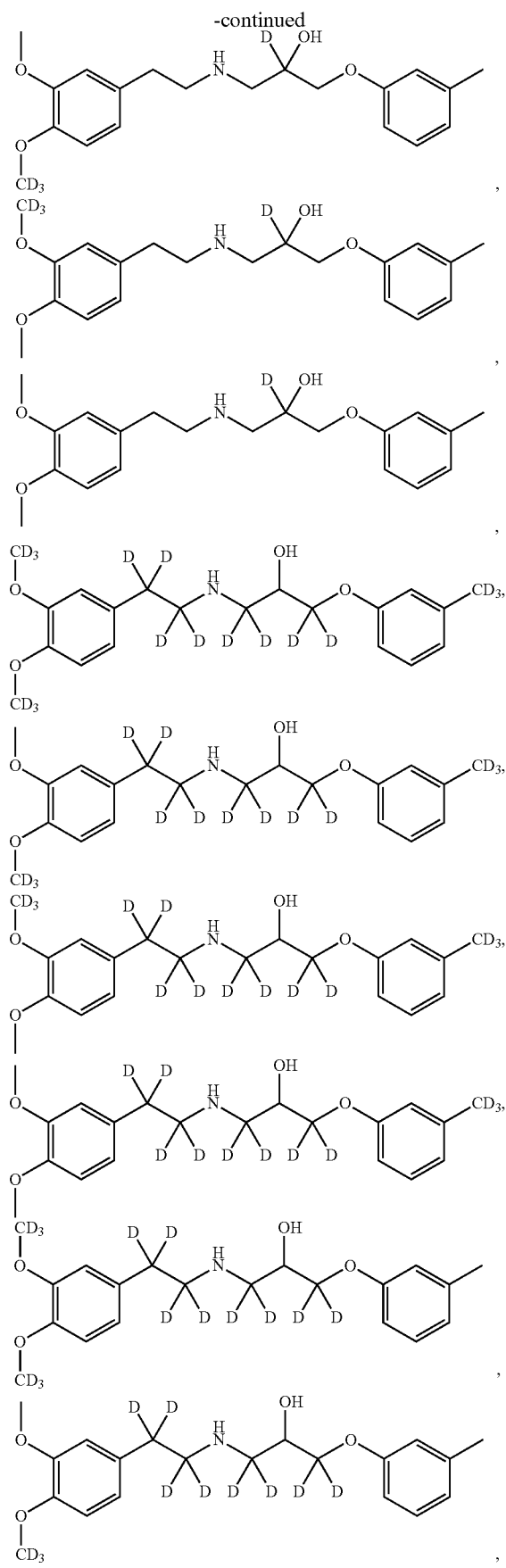

-continued

-continued

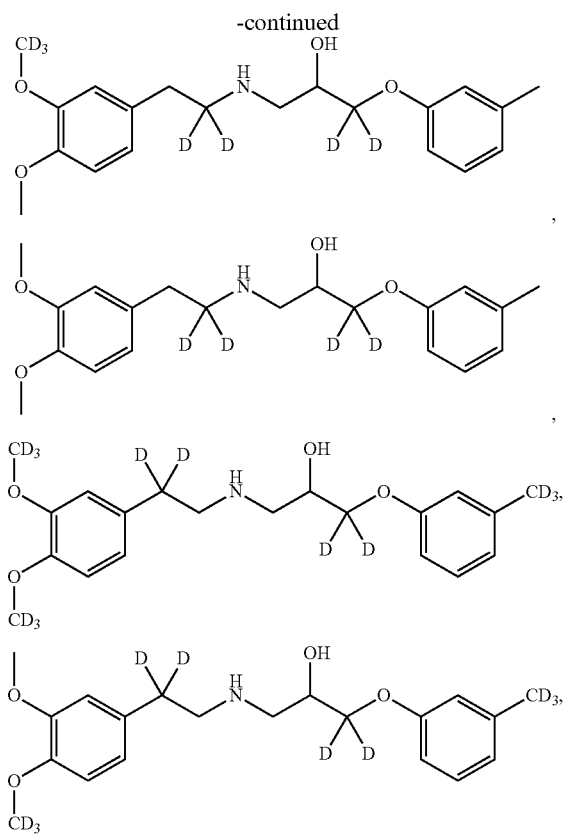
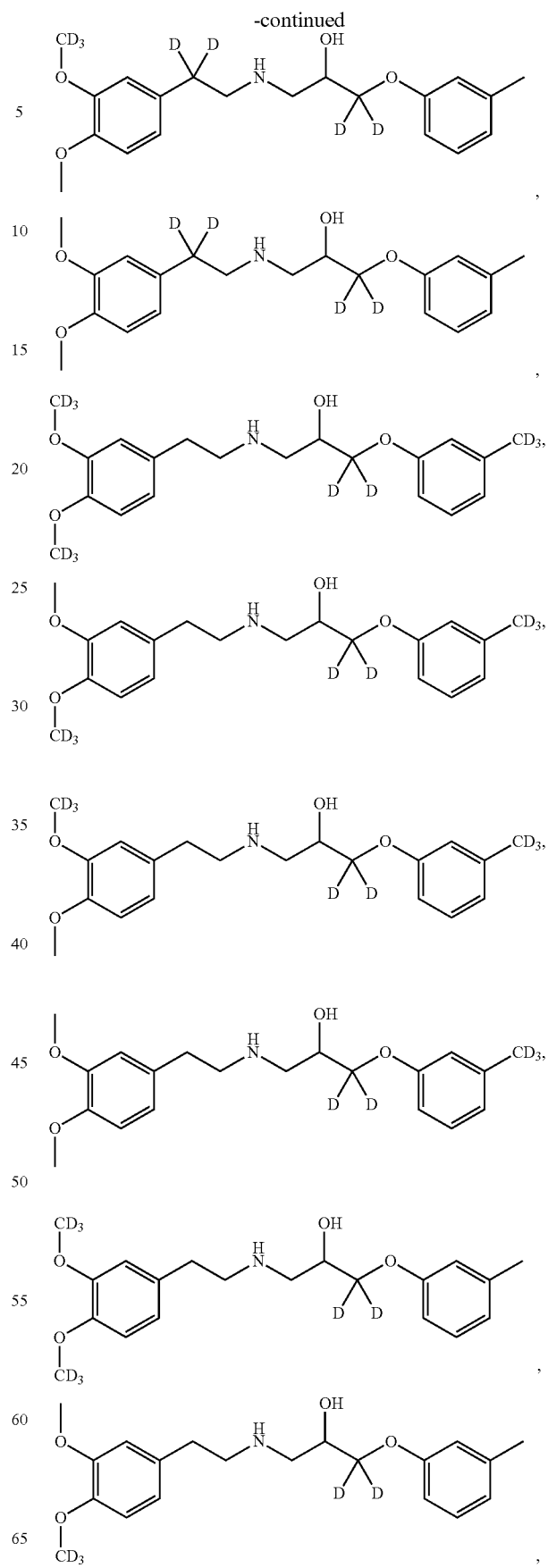

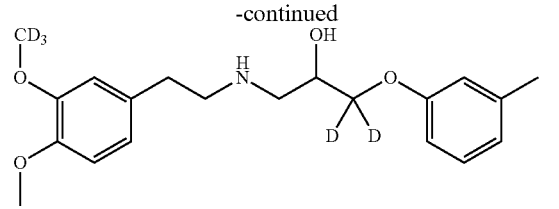,
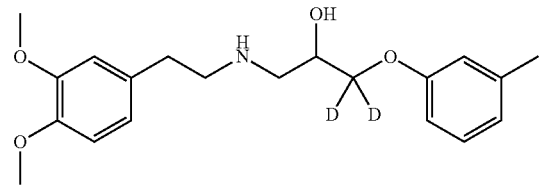,
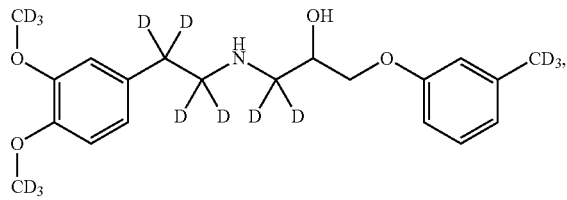,
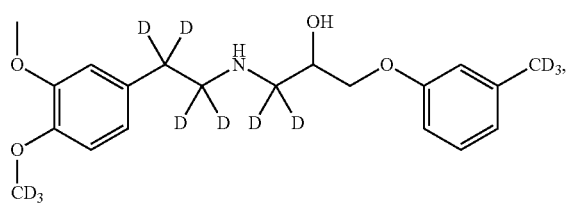,
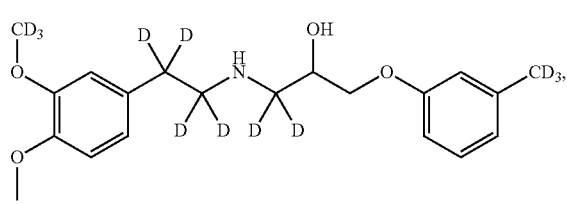,
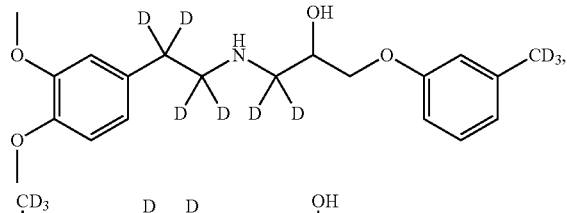,
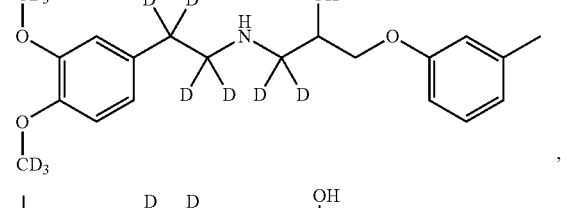,
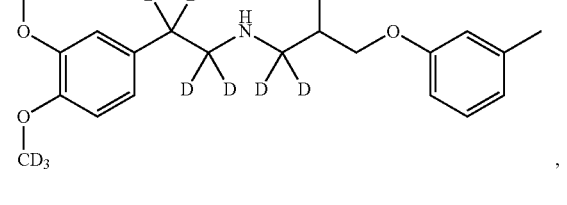,
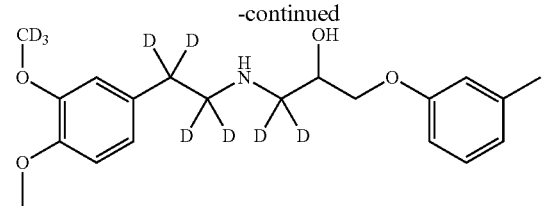,
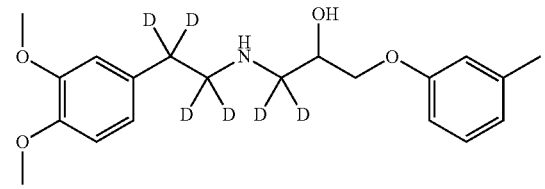,
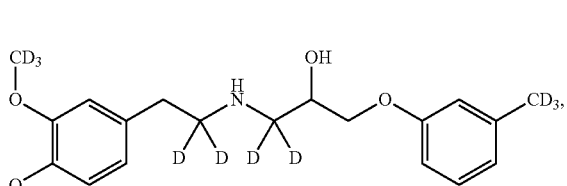,
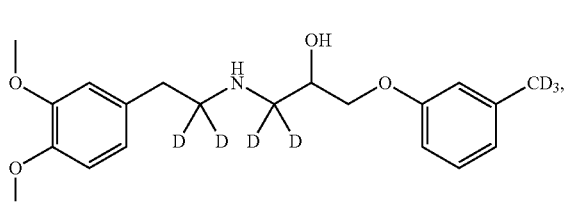,
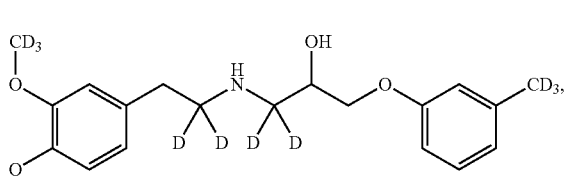,
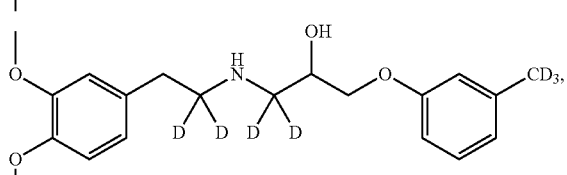,
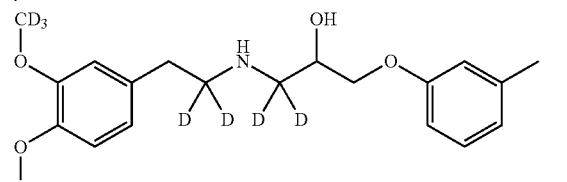,
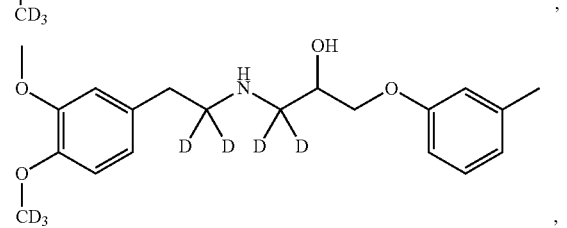,

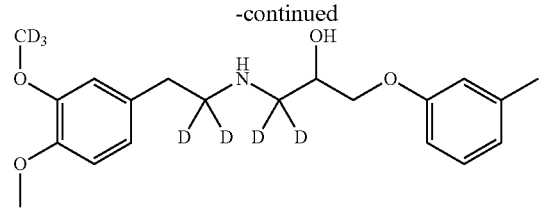
,
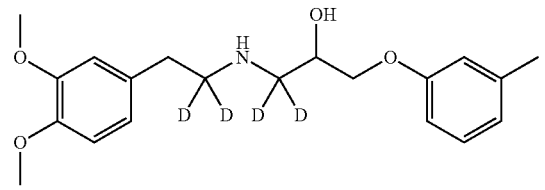
,
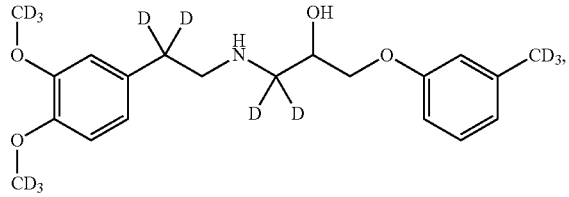
,
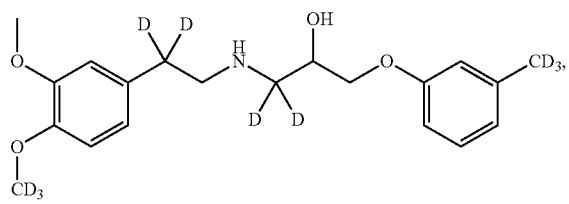
,
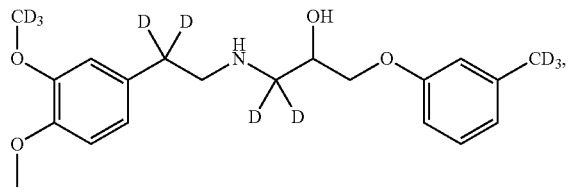
,
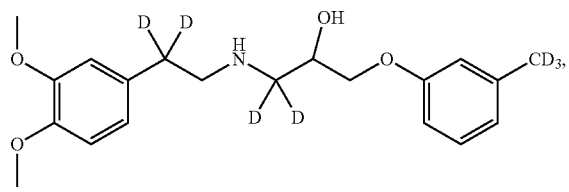
,
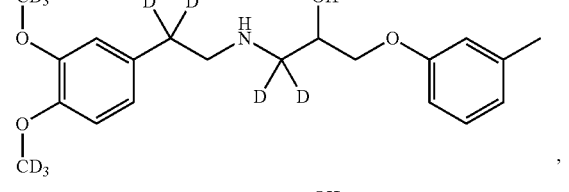
,
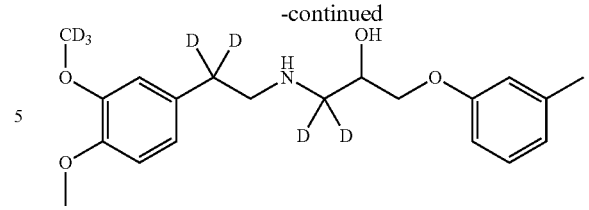
,
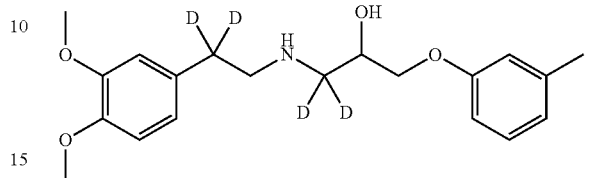
,
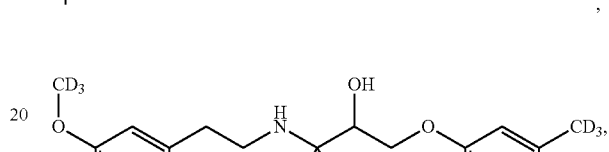
,
,
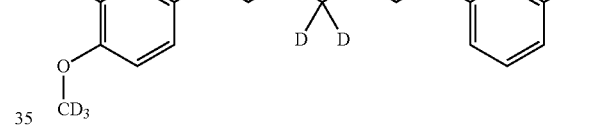
,
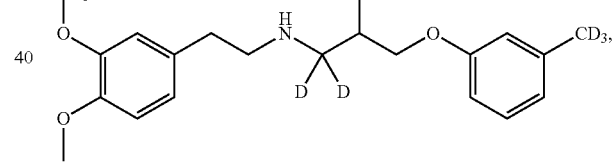
,
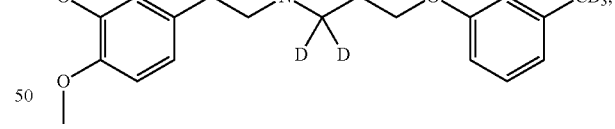
,
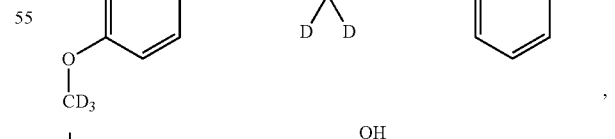
,

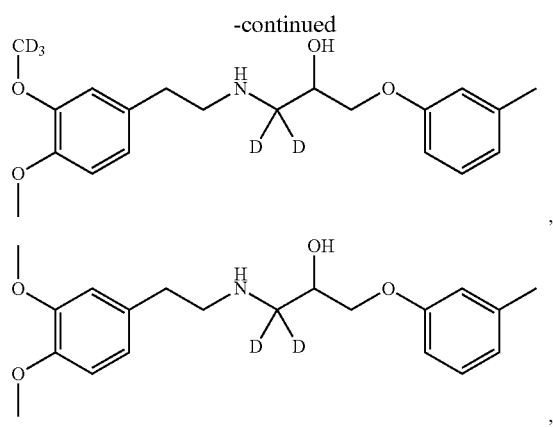
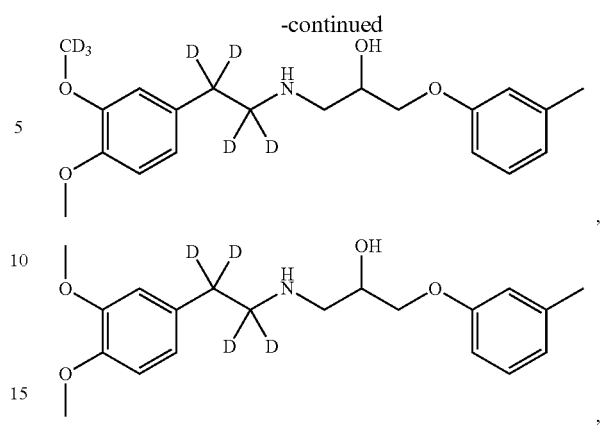
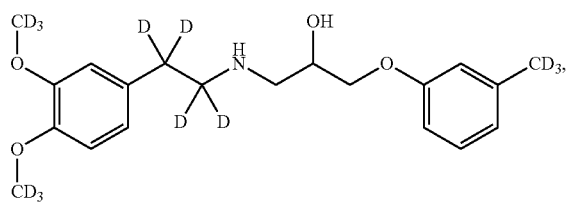
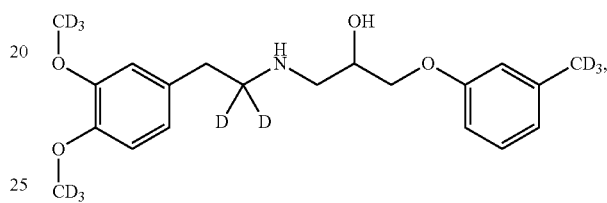
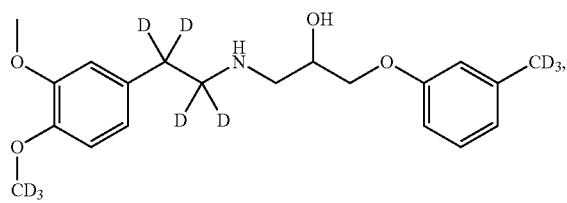
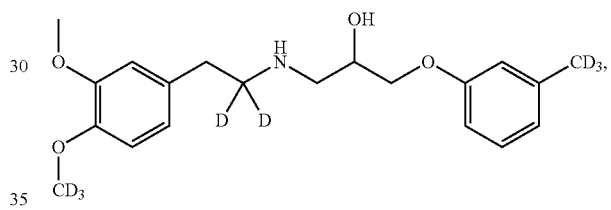
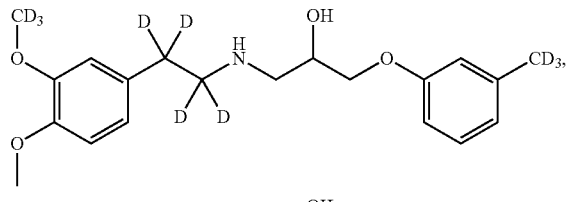
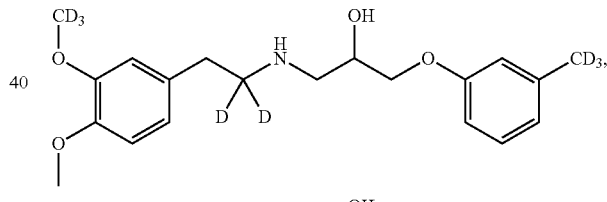
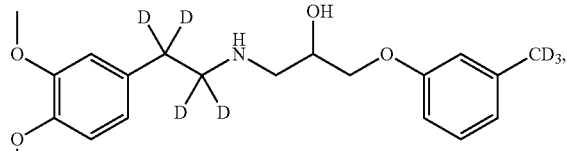
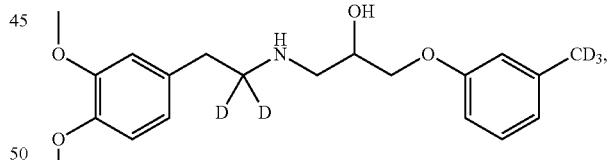
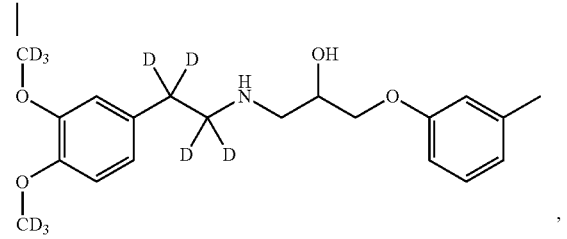
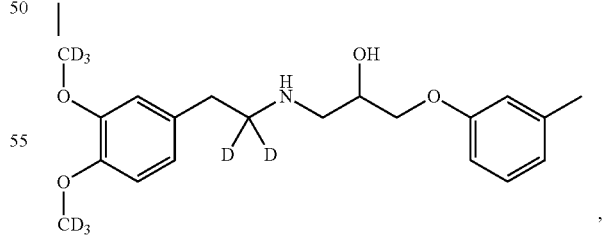
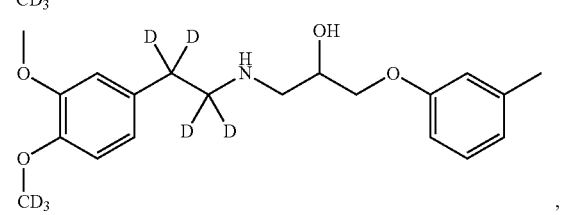
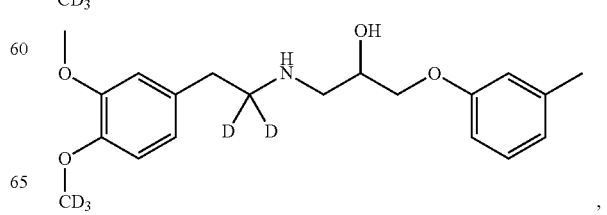

95
-continued
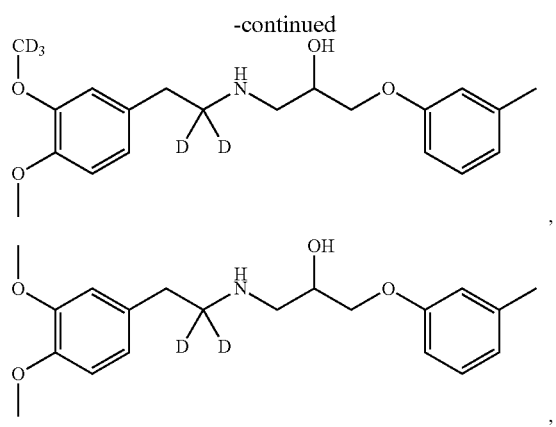
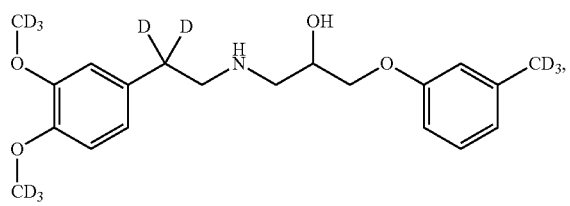
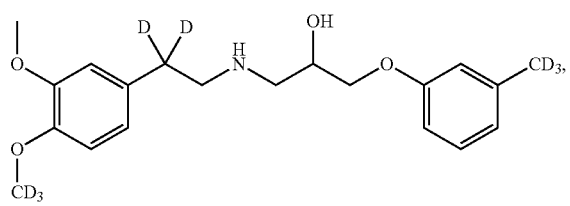
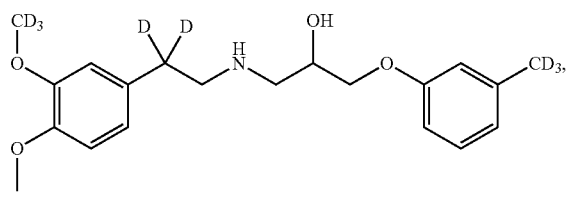
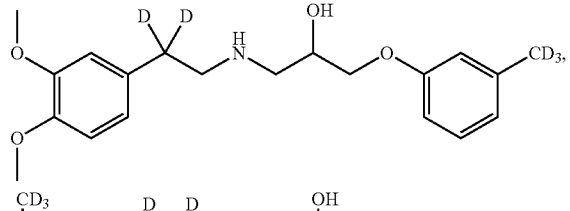
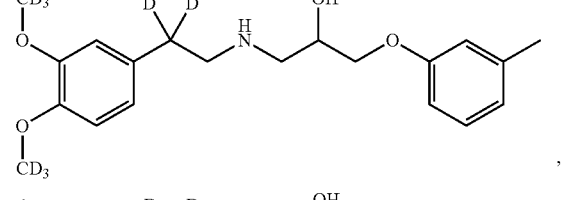
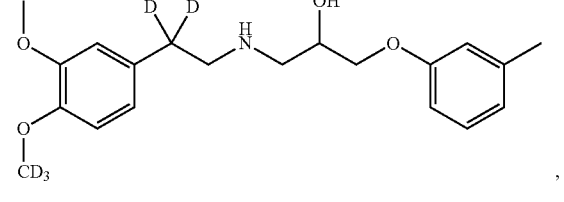
96
-continued
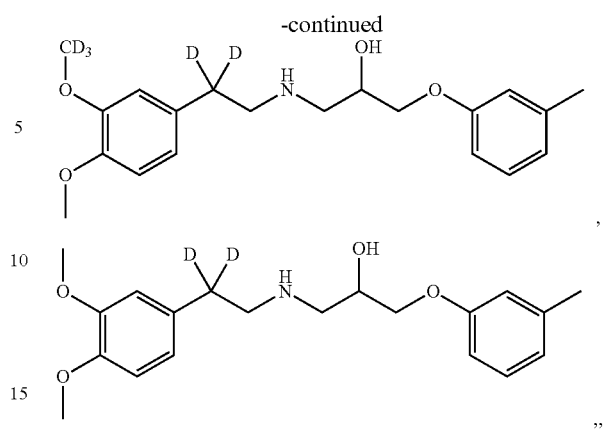
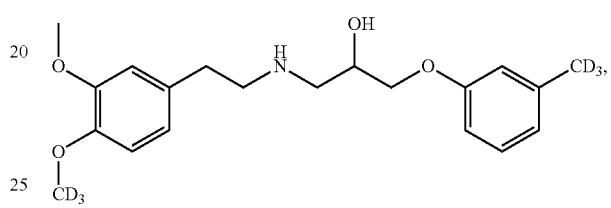
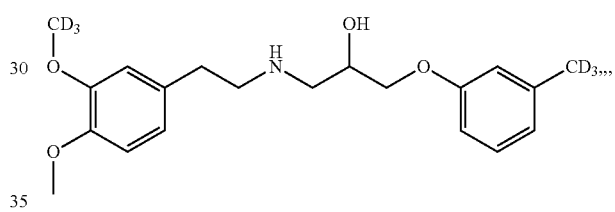
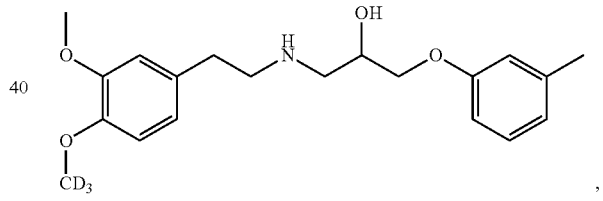
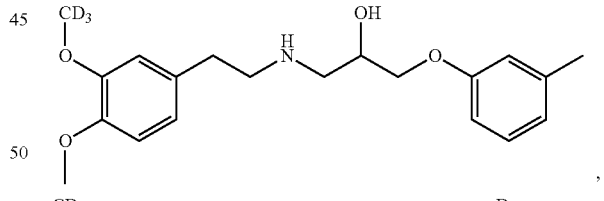
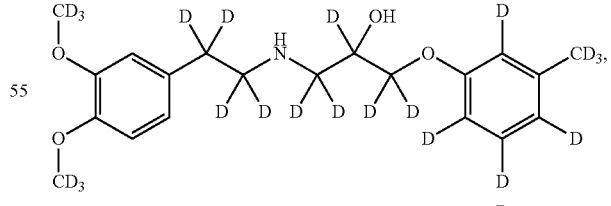
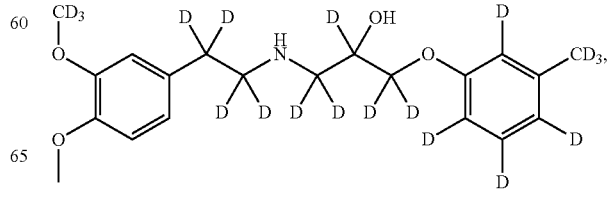

97
-continued
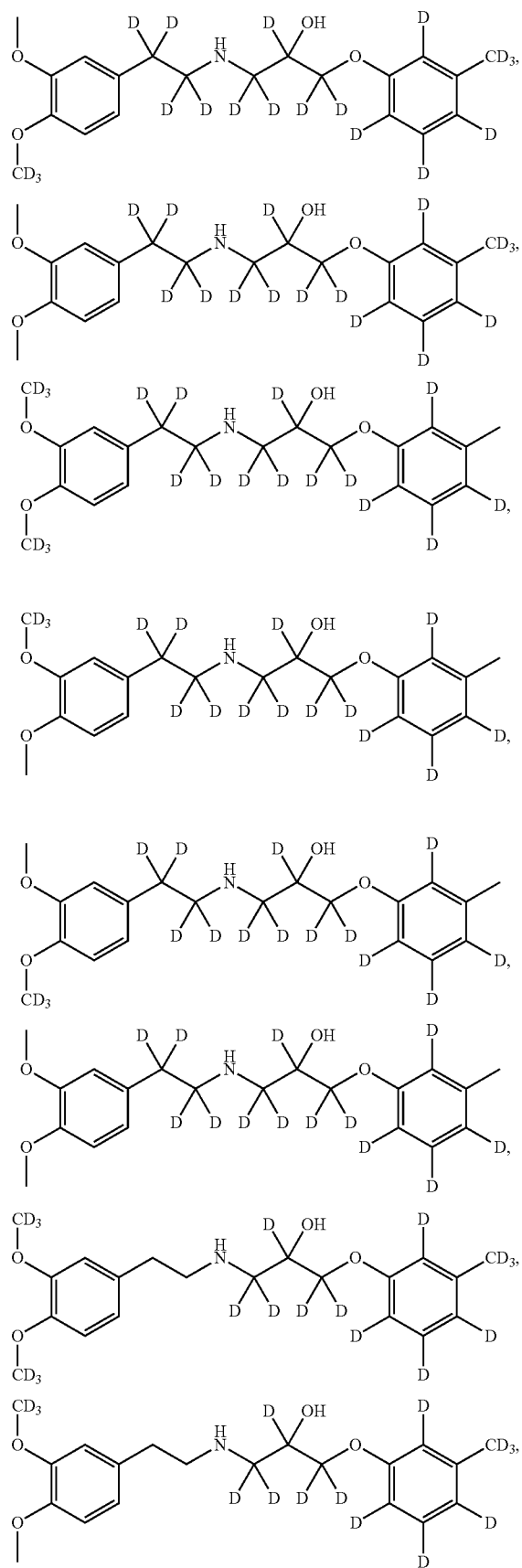
98
-continued
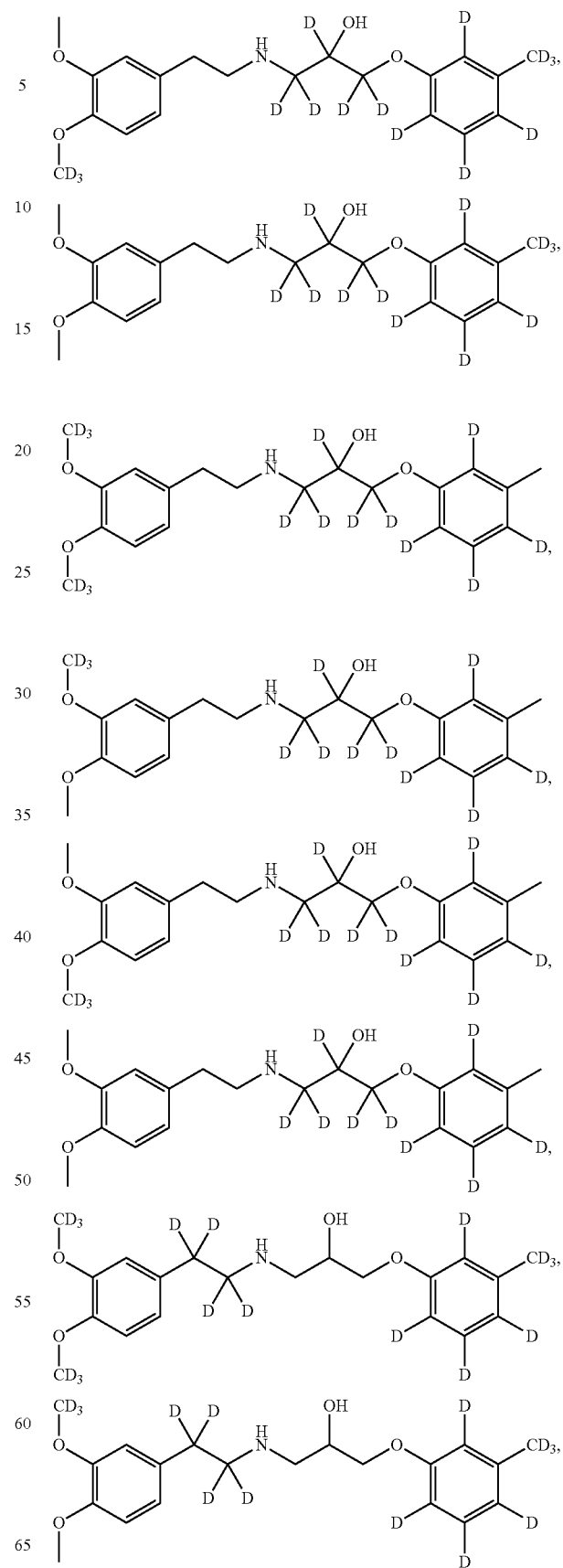

-continued

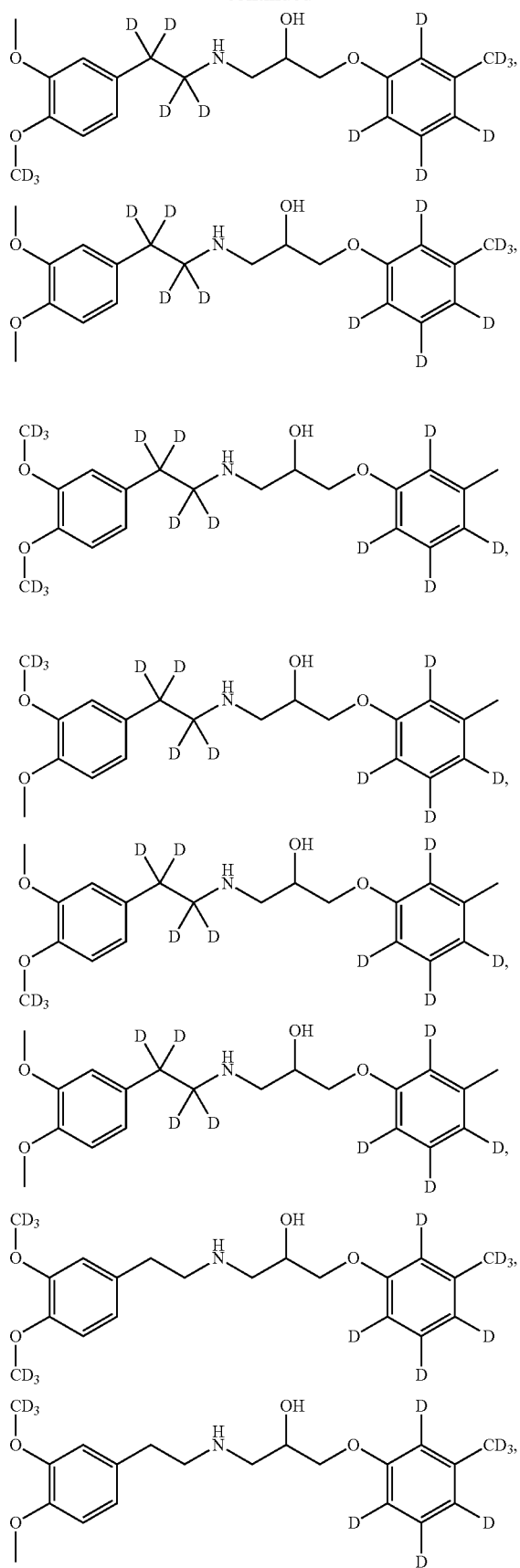

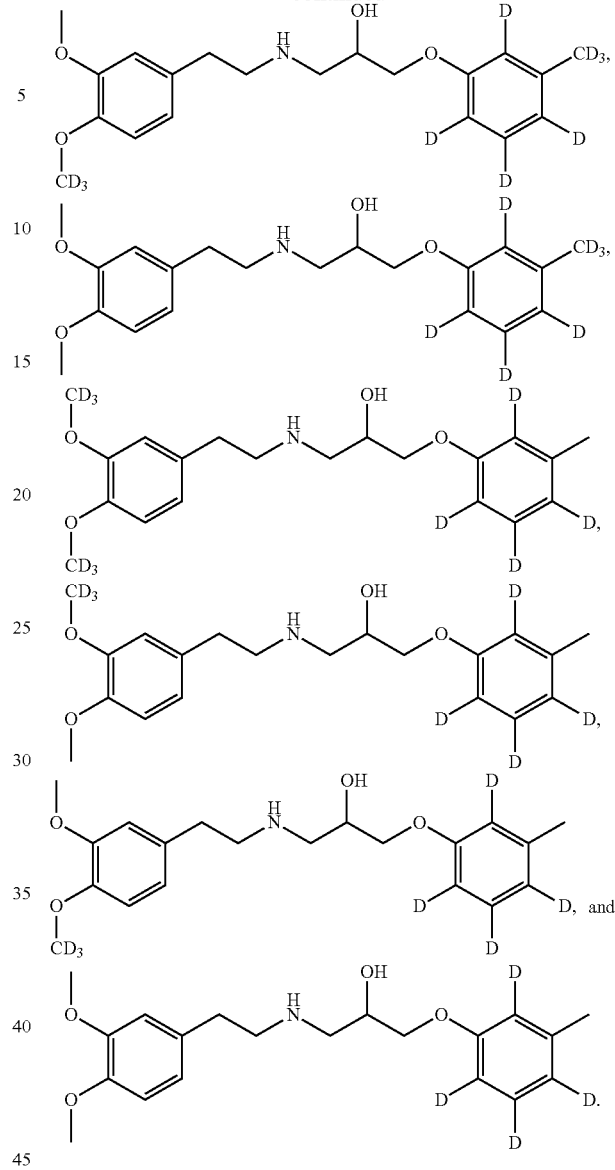

Changes in the metabolic properties of the compounds disclosed herein as compared to their non-isotopically enriched analogs can be shown using the following assays. Compounds listed above which have not yet been made and/or tested are predicted to have changed metabolic properties as shown by one or more of these assays as well.

Biological Activity Assays

In Vitro Liver Microsomal Stability Assay

Human liver microsomal stability assays were conducted at 0.5 mg per mL liver microsome protein with NADPH (2 mM, pH 7.4).

Test compounds were typically prepared as solutions in acetonitrile with 5% DMSO and added to the assay mixture (1 uM, final concentration in incubation) to be incubated at 37° C. Reactions were initiated with the addition of NADPH cofactor and were stopped at 0, 5, 15, 20 or 30 min after cofactor addition with stop reagent, acetonitrile. After quenching, plates containing samples were vibrated for 10 min (600 rpm/min) and then centrifuged at 5594 g for 15 min. Supernatant fractions were analyzed by LC-MS/MS to determine the percent remaining and estimate the degradation half-life of the test compounds. Results are given below.

| Example | Clearance % change over d0 | Half-life % change over d0 |
|---|---|---|
| 1 | 0.00 | 0.00 |
| 2 | 1.68 | −1.65 |
| 3 | −4.71 | 4.95 |
| 4 | −21.15 | 26.83 |
| 5 | 0.85 | −0.84 |

Other compounds disclosed herein are expected to have activity similar to or greater than the compounds disclosed above.

In Vitro Human Liver Microsomal Metabolite ID Assay

In vitro metabolite identification was conducted after incubating compounds (parent compound, final concentration 10 μM) with human liver microsomes (0.5 mg/mL) at 37° C. in 100 mM potassium phosphate buffer containing 5 mM $Mg^{2+}$ (K/Mg-Buffer) in the presence of NADPH. Samples taken at 0 min and 30 min were quenched by acetonitrile and analyzed using UPLC-UV-G2-S Q-Tof. Major metabolites of the tested compounds were identified by comparison of the LC-UV and LC-MS total ion chromatograms (TIC) in $T_0$ and $T_{30}$ samples using MassLynx and MetaboLynx software. The tandem mass spectra or MS/MS data for parent compounds and their metabolites were obtained using product ion scanning under positive and negative ion electrospray conditions. The possible chemical structures of the metabolites were deduced based on their MS/MS spectra.

Approximately 8 metabolites were identified by MS in most of tested compounds with putative structure assignment, including phase I biotransformations including hydroxylation of aromatic ring of the tolyl moiety, demethylation of the methyoxy group(s), and stepwise oxidation of methyl group in the tolyl moiety resulting in formation of a carboxylic acid. A subset of at least 4 of these metabolites could be detected by UV. The pattern of metabolite abundance relative to the unmetabolized parent compound for deuterium-substituted structures was compared to the same pattern with the nondeuterated compound. Examples with O-linked $CD_3$-groups on the aromatic ring were associated with lower abundance of O-demethylated metabolites. By contrast, and unexpectedly, examples with a $CD_3$-group linked to the aromatic ring are associated with higher abundance of ring mono-hydroxylation. Among these monohydroxy metabolites with increased abundance, one has beta-adrenergic receptor blocking activity in preclinical studies (Latts, J. R., Clinical Pharmacokinetics and Metabolism of Bevantolol, *Angiology—Journal of Vascular Diseases*, March 1986, p. 221-225).

In Vitro Competitive Radioligand Binding Assays for Beta-Adrenergic Antagonist Activity Methods as in: Takita M l, Kigoshi S, Muramatsu I. Selectivity of bevantolol hydrochloride towards alpha- and beta-adrenoceptor subtypes in rat cerebral cortex. Jpn J Pharmacol. 1992 February; 58(2):193-6.

Displacement of 1 nM 3H-Dihydroalprenolol binding to beta-adrenoceptors in rat cerebral cortex membranes is evaluated after co-incubation with various concentrations of example compounds. Examples are expected to displace 3H-Dihydroalprenolol in a manner similar to bevantolol (Takita).

In Vivo Assays for Antihypertensive Activity in Rats

Methods as in: Kaplan, H., Pharmacology of bevantolol hydrochloride, *Am J Cardio* 1986 58(12):3E-7E Spontaneously hypertensive rats are outfitted with a heparin-filled catheter into the left carotid artery which is attached heart rate/blood pressure transducer and monitoring device. After administration, example compounds are expected to reduce blood pressure over a 10 hour period to a degree similar as bevantolol (Kaplan).

Cardioselective Effects on Beta Adrenoreceptor Blocking Effects in Ex Vivo Tissues.

Methods as in: Hastings et al., Pharmacologic evaluation of CI-775, a cardioselective beta adrenergic antagonist, *Archives internationales de pharmacodynamie et de therapie*. March 1977; 226(1):81-99\

Guinea-pig atrial and tracheal tissues are attached to force displacement transducers in appropriate oxygenated buffers. Isoproterenol-induced increases in atrial contraction and isoproterenol-induced reductions in tracheal resting tone are compared in the presence of example compound or appropriate vehicles. Pre-incubation with example compounds are expected to inhibit isoproterenol-induced responses manner similar to a degree similar to bevantolol (cite Hastings).

Cardioselective Effects on Beta Adrenoreceptor Blocking Effects in Dog.

Methods as in: Hastings et al., Pharmacologic evaluation of CI-775, a cardioselective beta adrenergic antagonist, *Archives internationales de pharmacodynamie et de therapie*. March 1977; 226(1):81-99\

Anesthetized dogs are equipped with catheters in the common carotid or brachial arteries that are attached to strain gauge pressure transducers. Example compounds at concentrations of 0.2 to 6.0 mg/kg injected intravenously are expected to reduce resting blood pressure in a manner similar to bevantolol (Hastings). Dogs may also receive intravenous infusions of isoproterenol from 0.1 to 2.0 μg/kg before and after various doses of the example compounds. Example compounds are expected to reduce isoproterenol-induced changes in heart rate and blood pressure in a manner similar to bevantolol (Hastings).

In Vitro Metabolism Using Human Cytochrome $P_{450}$ Enzymes

The cytochrome $P_{450}$ enzymes are expressed from the corresponding human cDNA using a baculovirus expression system (BD Biosciences, San Jose, Calif.). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound of Formula I, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 min. The supernatant is analyzed by HPLC/MS/MS.

| Cytochrome $P_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |

| Cytochrome P$_{450}$ | Standard |
|---|---|
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Monoamine Oxidase A Inhibition and Oxidative Turnover

The procedure is carried out using the methods described by Weyler, *Journal of Biological Chemistry* 1985, 260, 13199-13207, which is hereby incorporated by reference in its entirety. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM NaP$_i$ buffer, pH 7.2, containing 0.2% Triton X-100 (monoamine oxidase assay buffer), plus 1 mM kynuramine, and the desired amount of enzyme in 1 mL total volume.

Monoamine Oxidase B Inhibition and Oxidative Turnover

The procedure is carried out as described in Uebelhack, *Pharmacopsychiatry* 1998, 31(5), 187-192, which is hereby incorporated by reference in its entirety.

VMAT2 Functional Assay

The following VMAT2 Functional Assay determines the interaction between compounds and the VMAT2 present in isolated cerebral cortical vesicles. See, e.g., Sandoval et al., J Neurosci, 2002, V. 22, pp. 8705-10, which is hereby incorporated by reference in its entirety.

Rat cortical vesicles are purified using differential centrifugation, and the vesicles obtained are diluted in assay buffer (e.g., 100 mM potassium tartrate, 1.7 mM ascorbic acid, 0.05 mM EGTA, 0.1 mM EDTA, 2 mM Magnesium-ATP and 25 mM HEPES) and pre-incubated with the positive reference control (reserpine 10 µM), the comparative sample (tetrabenazine) or a test compound for 30 minutes at room temperature. Uptake begins with the addition of [$^3$H]-dopamine (30 µM) and the mixture is allowed to incubate for 15 minutes at room temperature. After that time, the reaction is stopped by vacuum filtration, and the amount of radioactivity of the radiolabeled [$^3$H]-dopamine trapped onto the filters is determined using liquid scintillation spectrophotometry (e.g., Beckman and Perkin Elmer). The amount of radioactivity obtained with the comparative sample or a test compound is compared with the amount of radioactivity obtained with the positive-reference control (reserpine).

The half maximal inhibitory concentration (IC$_{50}$) of the comparative sample and test compounds is determined by measuring the concentration of competing ligand which displaces 50% of the specific binding of the [$^3$H]-dopamine. The IC$_{50}$ value is converted to an absolute inhibition constant K$_i$ using the Cheng-Prusoff equation. Two separate, independent experiments are typically performed. IC$_{50}$ values in roughly the same order of magnitude as the comparative sample (e.g., tetrabenazine) are indicative of efficacy in treatment of hyperkinetic movement disorders by the compounds of the present invention. Test compounds of the present invention are expected to yield IC$_{50}$ values similar to, or lower than, the comparative sample, and similar to, or lower than, bevantolol.

In Vitro Radioligand Binding Assay

The procedure is carried out as described in Scherman et al., *Journal of Neurochemistry* 1988, 50(4), 1131-36, which is hereby incorporated by reference in its entirety. Male rats are killed and the whole brain, except cerebellum, is removed, homogenized in 50 mM Tris buffer, pH 7.4, and stored frozen at −70° C. Binding of [$^3$H]-TBZOH (α-dihydrotetrabenazine) is evaluated by incubating brain homogenates (3-5 mg protein/ml) in 0.3 M sucrose, 50 mM HEPES, pH 8, at 30° C. in 50 µl final volume, for 30 min, in the presence or absence of test compounds or tetrabenazine as a comparison. The samples are then filtered on GF/C glass fiber filters as described in Scherman et al. (Scherman et al. Brain Res. 1986, 370, 186-191) with a washing buffer containing 0.3 M sucrose; 10 mM Tris, pH 8 and 100 µM test compounds, or tetrabenazine as a positive control. Samples are assayed in triplicate, and nonspecific binding (measured in the presence of 1 mM tetrabenazine) is subtracted. Test compounds of the invention are expected to displace [$^3$H]-TBZOH with potencies that are significantly different than nonspecific binding.

In Vivo Radioligand Binding Assay

The procedure is carried out as described in Kilbourn et al., *Synapse* 2002, 43(3), 188-194, which is hereby incorporated by reference in its entirety. In vivo binding of radioligands is done in Sprague-Dawley CD rats. Animals are anesthetized with sodium pentobarbital and a catheter is inserted into one or both femoral veins. The incisions are closed and animals are placed in a plastic restraining tube and allowed to awaken. Test compounds or saline (controls) injections are done via the femoral vein catheter. Radioligand ([$^3$H]-TBZOH (α-dihydrotetrabenazine) injection is done through the femoral vein catheters using a programmable infusion pump. Bolus administration of radioligands is done using a 1-min infusion of radioligand in a volume of 1 ml. Equilibrium infusion studies are performed using a bolus administration of 66.6% of the dose (1 ml) over a 1-min period, followed by a constant infusion of the remaining 33.3% (o.5 ml) of the dose over the remaining 59 min (for 10 hr infusion studies) or 119 min (2-hr infusion studies). Test compounds (i.e. bevantolol and analogs as well as tetrabenazine as a positive control and vehicle as a negative control) are co-infused with radioligand. At designated times, animals are killed by i.v. injection of an overdose of sodium pentobarbital and the brains removed and dissected according to a literature method (Glowinski and Iversen, J. Neurochem. 1966, 13, 655-669) into samples of striatum, cortex, hippocampus, hypothalamic region, thalamus, pons/medulla, and cerebellum. Tissue samples are weighed and tissue solubilizer is added and after digestion (2-3 days) scintillation fluid is added and the sample counted for tritium. Data are calculated as percent injected dose/gram tissue. Test compounds of the present invention are expected to displace [$^3$H]-TBZOH with potencies significantly different than vehicle.

In Vivo Radioligand Binding Assay

The procedure is carried out as described in Kilbourn et al., *European Journal of Pharmacology* 1997, 331(2-3), 161-68, which is hereby incorporated by reference in its entirety. Sprague-Dawley female rats are anesthetized and prepared with catheters as described for the previous assay above. Binding of (α-(+)-[$^3$H]-TBZOH (α-(+)-dihydrotetrabenazine), in the presence or absence of test compounds, is evaluated after bolus, or bolus plus infusion, administration. Test compounds (bevantolol, test compound, or 50 mg/kg tetrabenazine as a positive control) are dissolved in 1.5 ml of saline containing 5% ethanol. In some animals, this vehicle servers as a negative control. For the bolus plus infusion experiments, α-(+)-[$^3$H]-TBZOH (10 µCi) is added to this solution and the combination of radioligand and test compound is infused for 1 hr using the ⅔ bolus:⅓ infusion protocol described in the previous assay. For the bolus experiments, 30 mg/kg test compound is administered using the identical infusion protocol, but α-(+)-[$^3$H]-TBZOH is administered α-(+)-[$^3$H]-TBZOH as a 1 min bolus starting 45 min into the test compound infusion. In each set of experiments, animals are killed at the end of the 60 min infusion. Evaluation of binding is performed as described in the previous assay above. Test compounds of the present invention are expected to displace α-(+)-[$^3$H]-TBZOH with potencies comparable significantly different than vehicle.

$^3$H-Histamine Transport Assay

The procedure is carried out as described in Erickson et al., *Journal of Molecular Neuroscience* 1995, 6(4), 277-87, which is hereby incorporated by reference in its entirety. CV-1 cells expressing VMAT1 and VMAT2 are prepared as described in Erickson et al. and rinsed with intracellular buffer (110 mM potassium tartrate, 5 mM glucose, 1 mM ascorbic acid, 10 μM pargyline, and 20 mM HEPES, pH 8.0) and permeabilized for 10 min at 37° C. in uptake buffer with 10 mM digitonin. The medium is replaced with fresh buffer without digitonin containing 5 mM MgATP and [$^3$H]histamine (45 Ci/mmol) and incubated at 37° C. for various lengths of time. Tetrabenazine at concentrations of 2 μM (as a positive control), solution (as a negative control) or test compounds are added immediately prior to addition of radiolabeled substrate [$^3$H]histamine. Uptake of [$^3$H]histamine is terminated with two washes in buffer containing 2 mM MgSO$_4$ on ice. Test compounds of the present invention are expected to inhibit VMAT2-mediated histamine transport with potencies significantly greater than test article-free solution.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I:

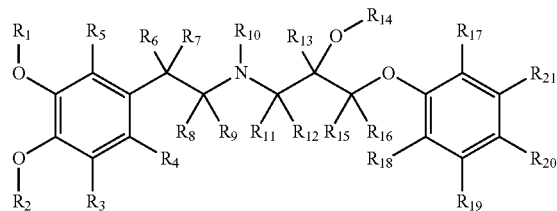

(I)

or a salt thereof, wherein:
$R_1$-$R_2$ and $R_{21}$ are independently —CH$_3$, —CH$_2$D, —CD$_2$H, or —CD$_3$; and
(i) $R_6$ and $R_7$ are deuterium; and
$R_3$-$R_5$ and $R_8$-$R_{20}$ are, independently, hydrogen or deuterium; or
(ii) $R_8$ and $R_9$ are deuterium; and
$R_3$-$R_7$ and $R_{10}$-$R_{20}$ are, independently, hydrogen or deuterium; or
(iii) $R_6$-$R_9$ are deuterium; and
$R_3$-$R_5$ and $R_{10}$-$R_{20}$ are, independently, hydrogen or deuterium; or
(iv) $R_{11}$ and $R_{12}$ are deuterium; and
$R_3$-$R_{10}$ and $R_{13}$-$R_{20}$ are, independently, hydrogen or deuterium; or (v) $R_{13}$ is deuterium; and
$R_3$-$R_{12}$ and $R_{14}$-$R_{20}$ are, independently, hydrogen or deuterium; or
(vi) $R_{15}$ and $R_{16}$ are deuterium; and
$R_3$-$R_{14}$ and $R_{17}$-$R_{20}$ are, independently, hydrogen or deuterium; and
at least one of the deuteriums has a deuterium enrichment of no less than about 10%.

2. The compound as recited in claim 1 wherein $R_{10}$ and $R_{14}$ are hydrogen.

3. The compound as recited in claim 1 wherein $R_1$ is CD$_3$.

4. The compound as recited in claim 1 wherein $R_2$ is CD$_3$.

5. The compound as recited in claim 1 wherein $R_{21}$ is CD$_3$.

6. The compound as recited in claim 1 wherein $R_6$ and $R_7$ are deuterium.

7. The compound as recited in claim 1 wherein $R_8$ and $R_9$ are deuterium.

8. The compound as recited in claim 1 wherein $R_6$-$R_9$ are deuterium.

9. The compound as recited in claim 1 wherein $R_{11}$ and $R_{12}$ are deuterium.

10. The compound as recited in claim 1 wherein $R_{13}$ is deuterium.

11. The compound as recited in claim 1 wherein $R_{15}$ and $R_{16}$ are deuterium.

12. The compound as recited in claim 1 wherein the compound is

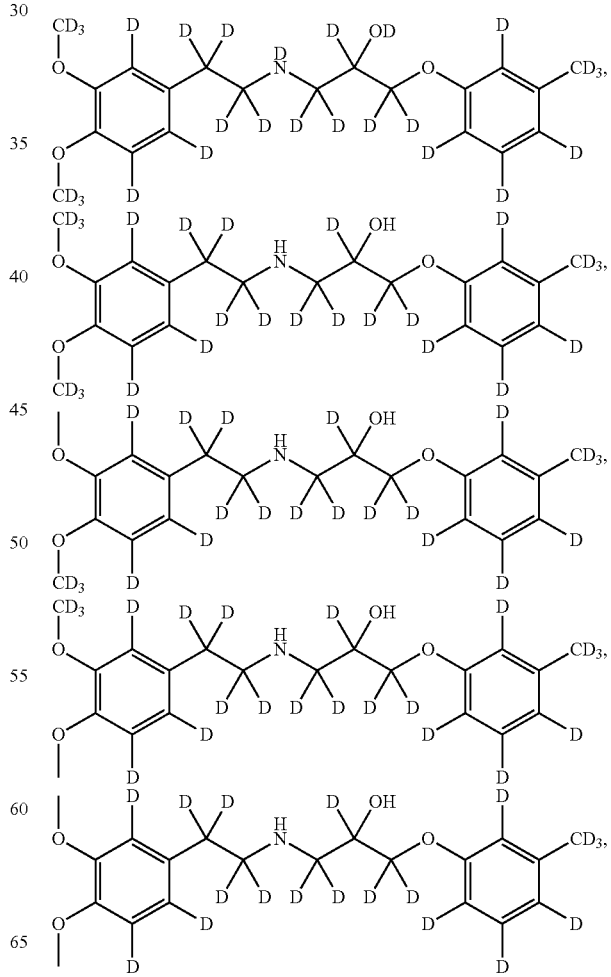

-continued
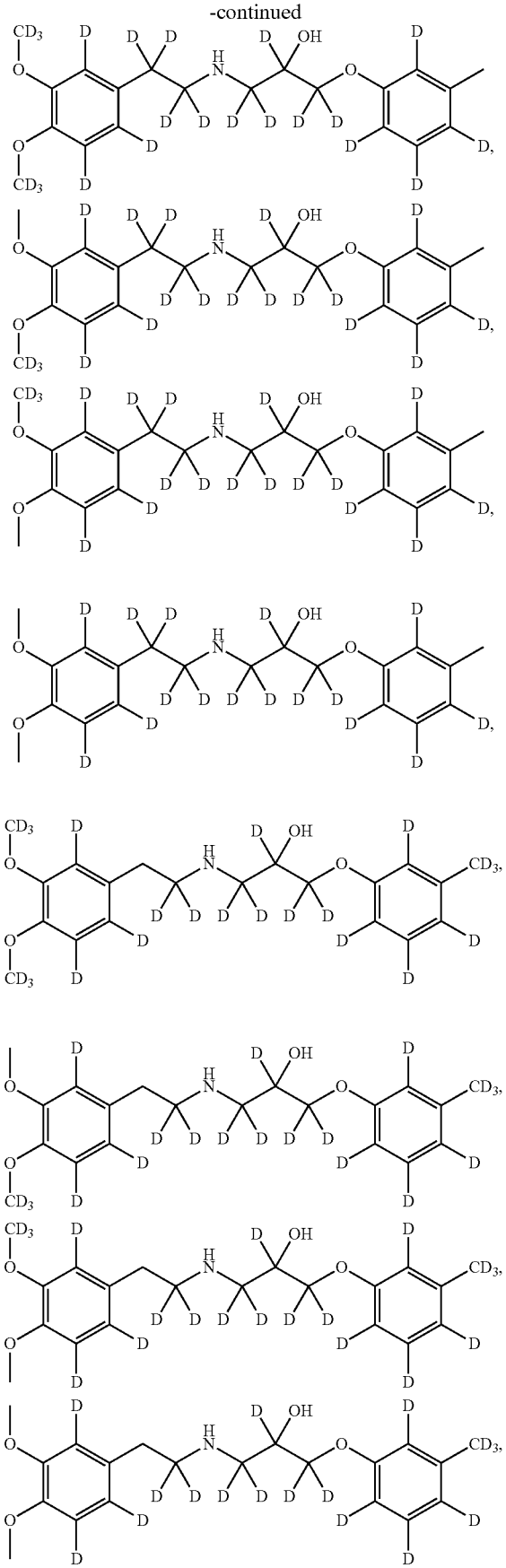
-continued
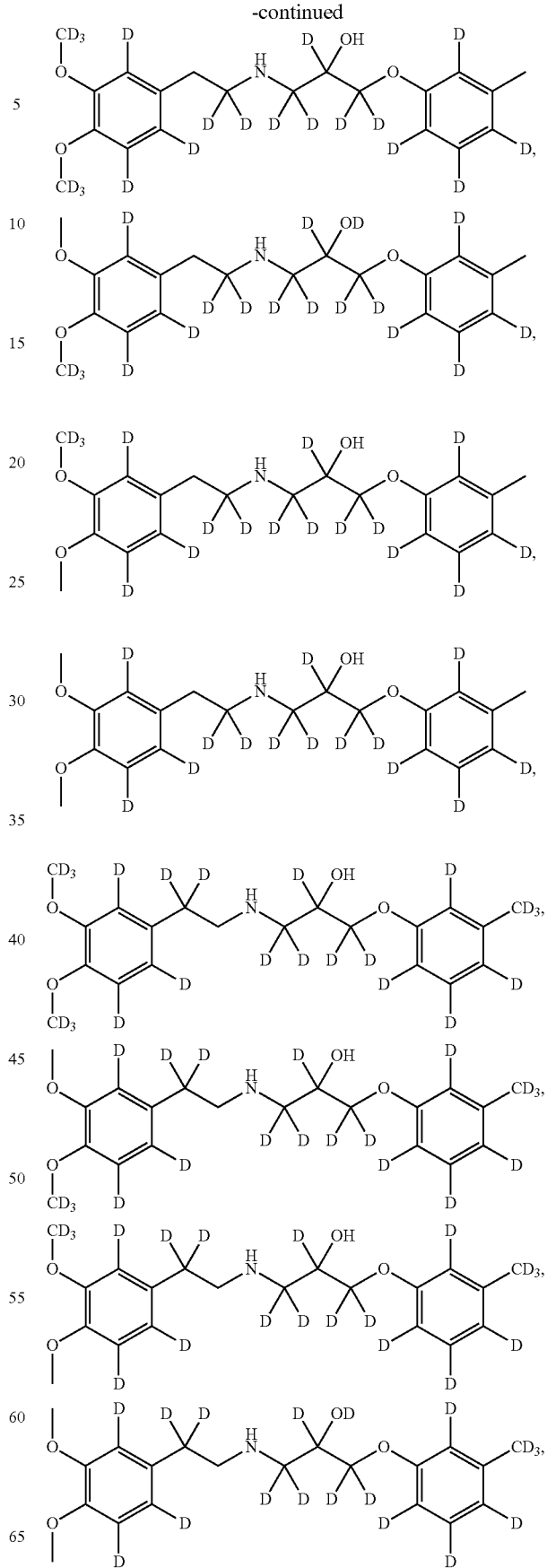

109
-continued
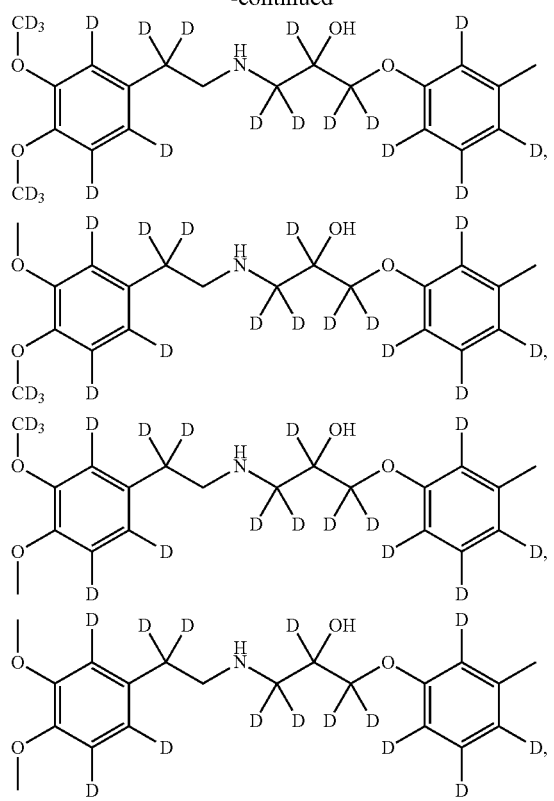
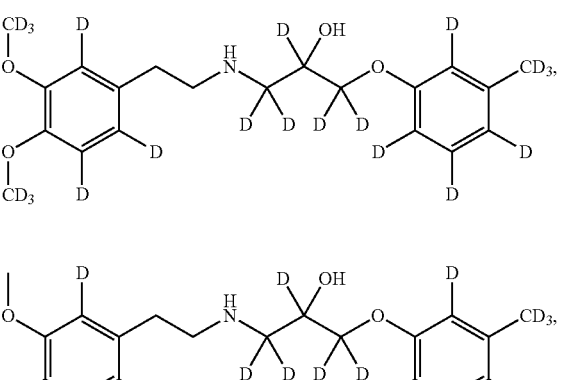
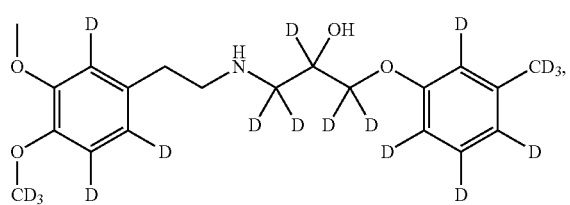
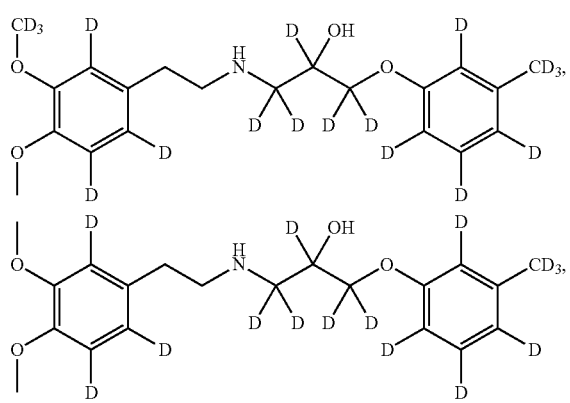
110
-continued
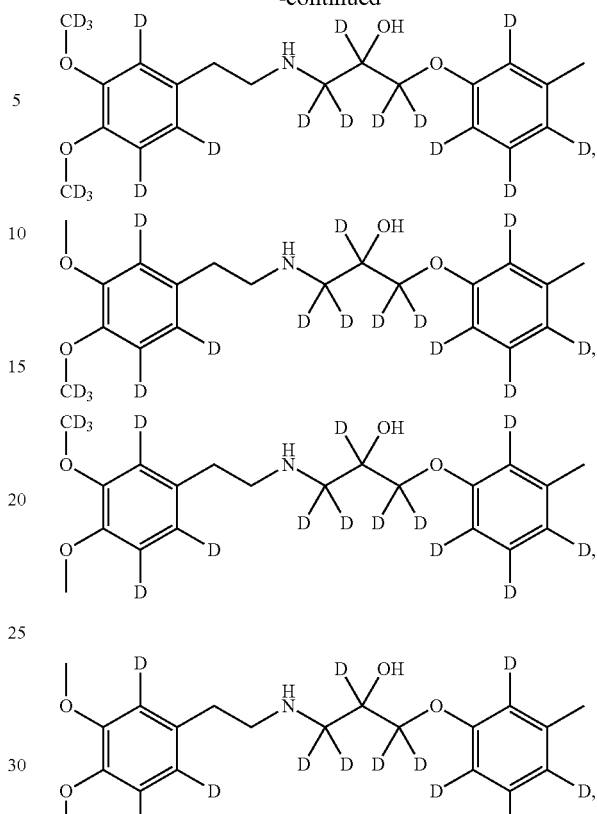
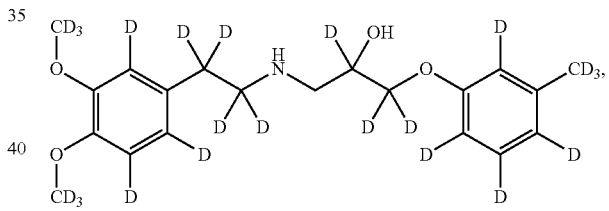
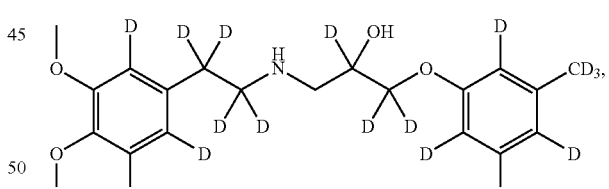
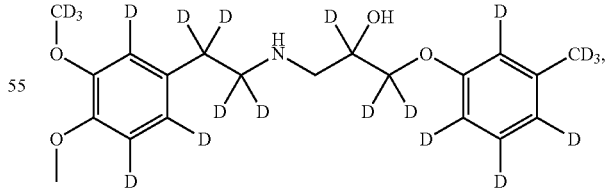
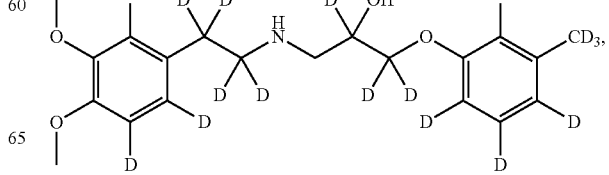

111
-continued
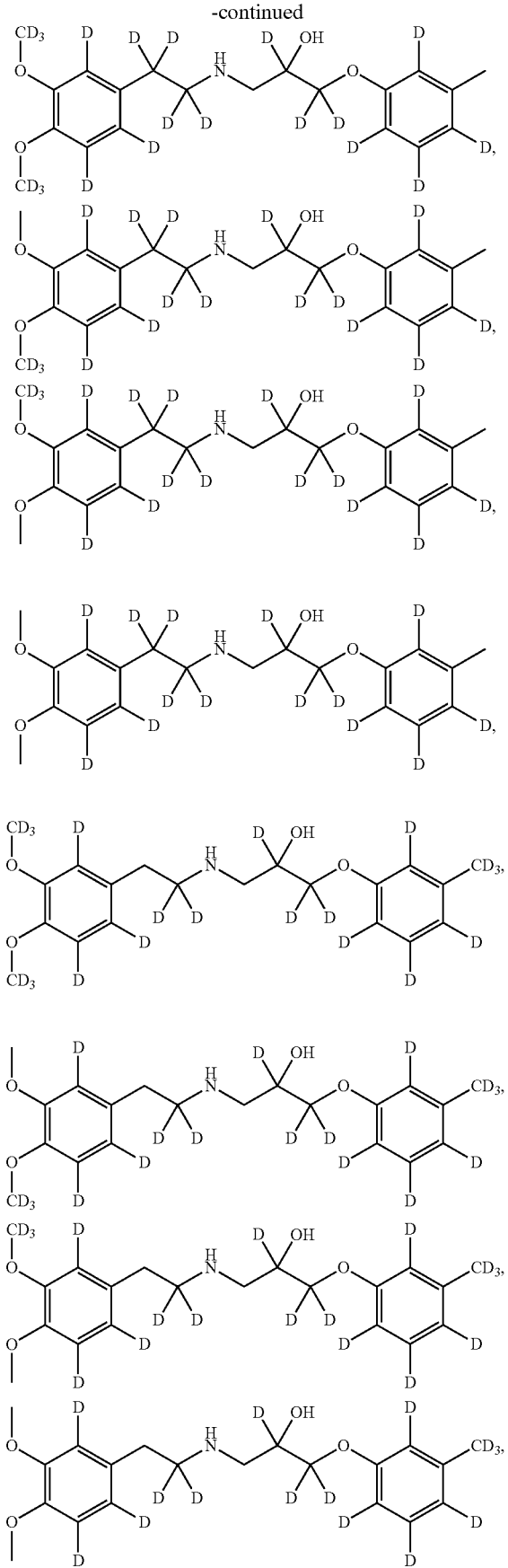
112
-continued
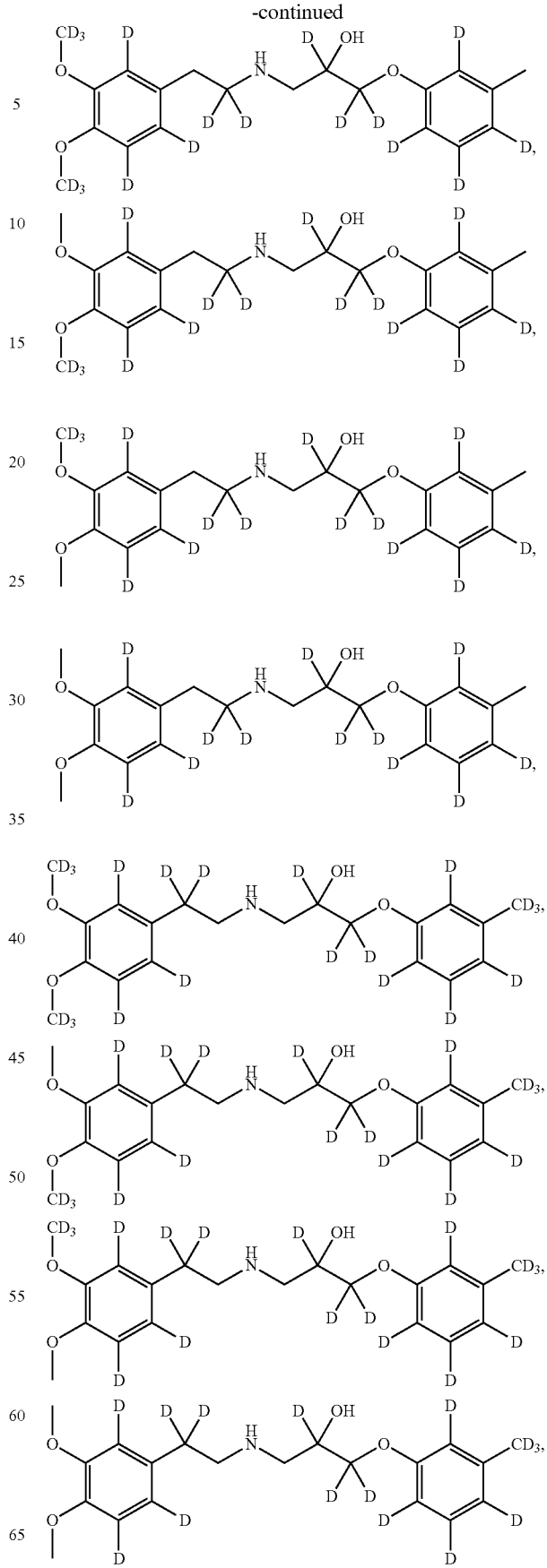

113
-continued
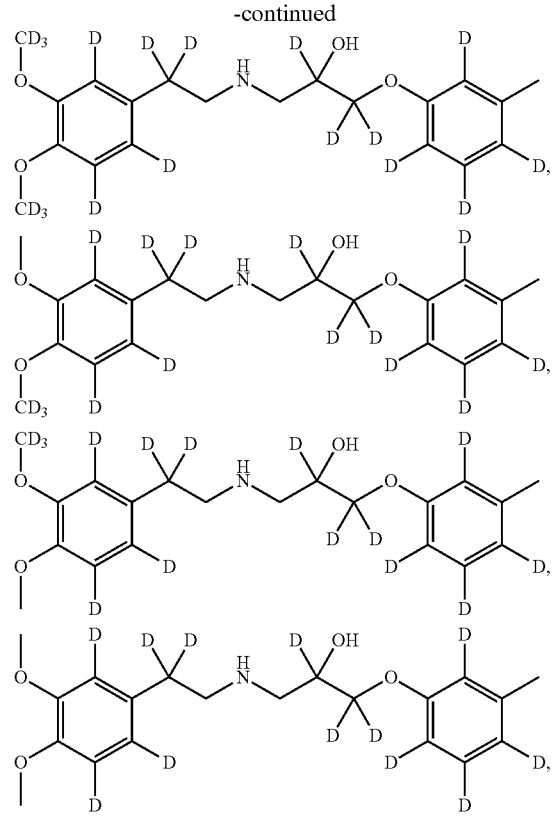
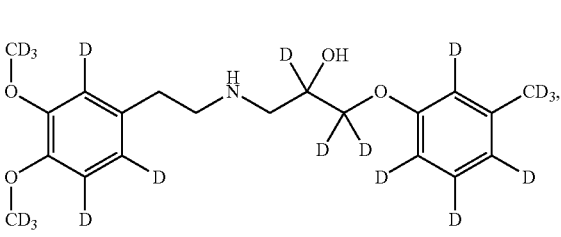
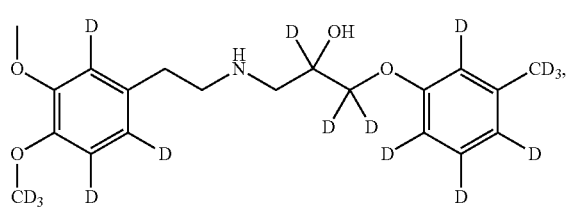
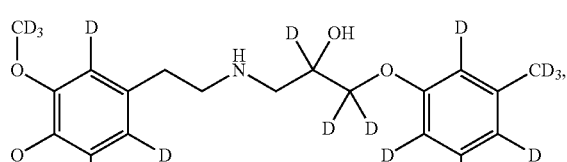
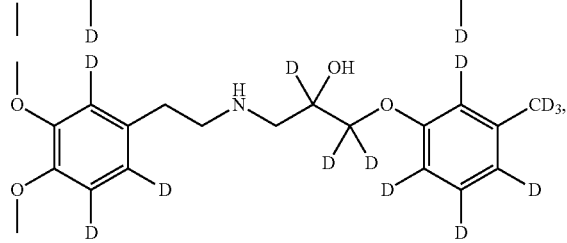
114
-continued
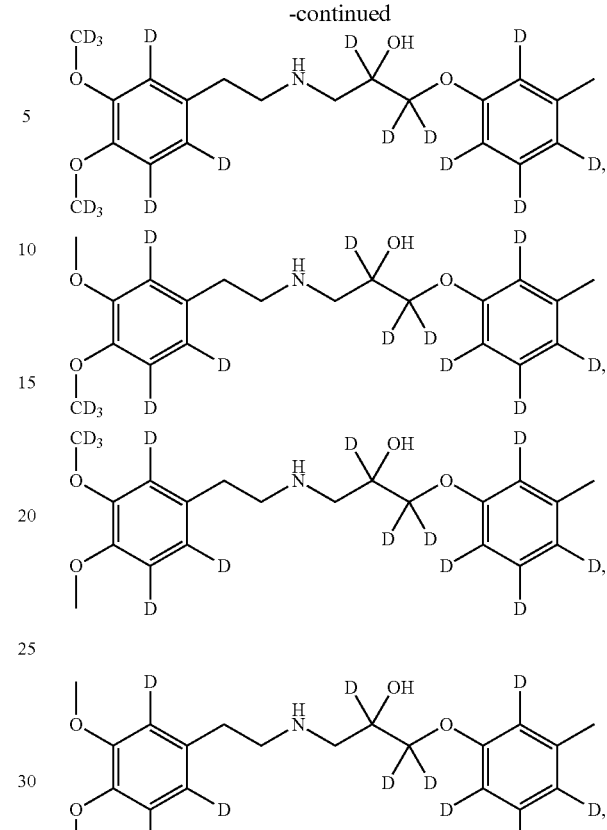
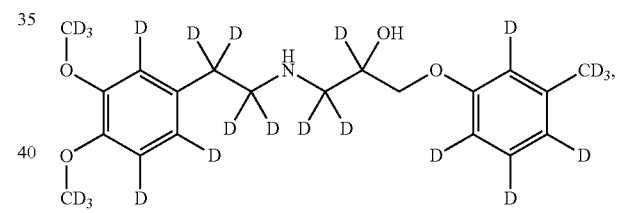
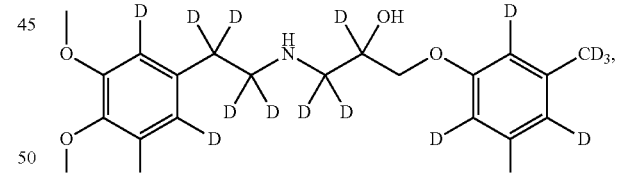
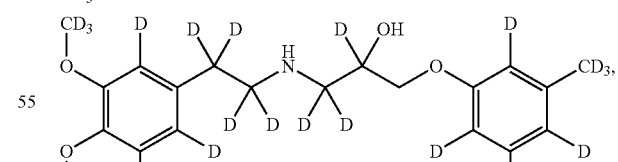
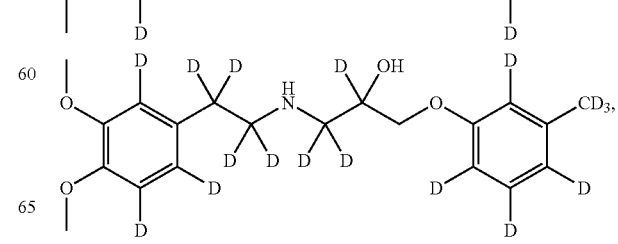

115
-continued
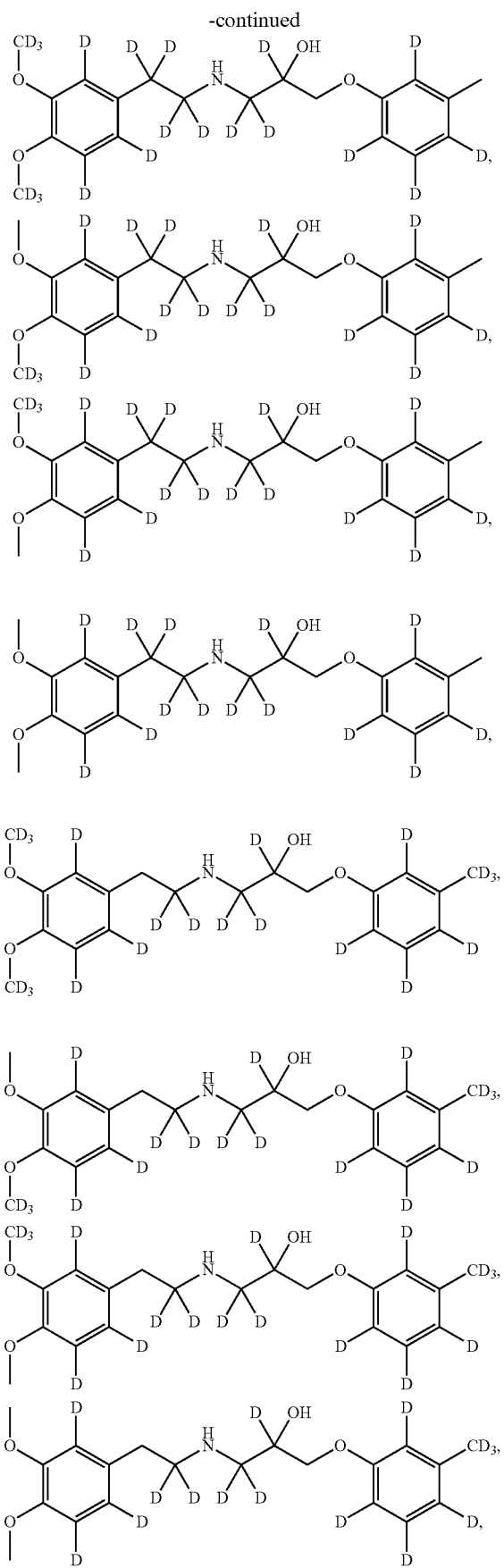
116
-continued
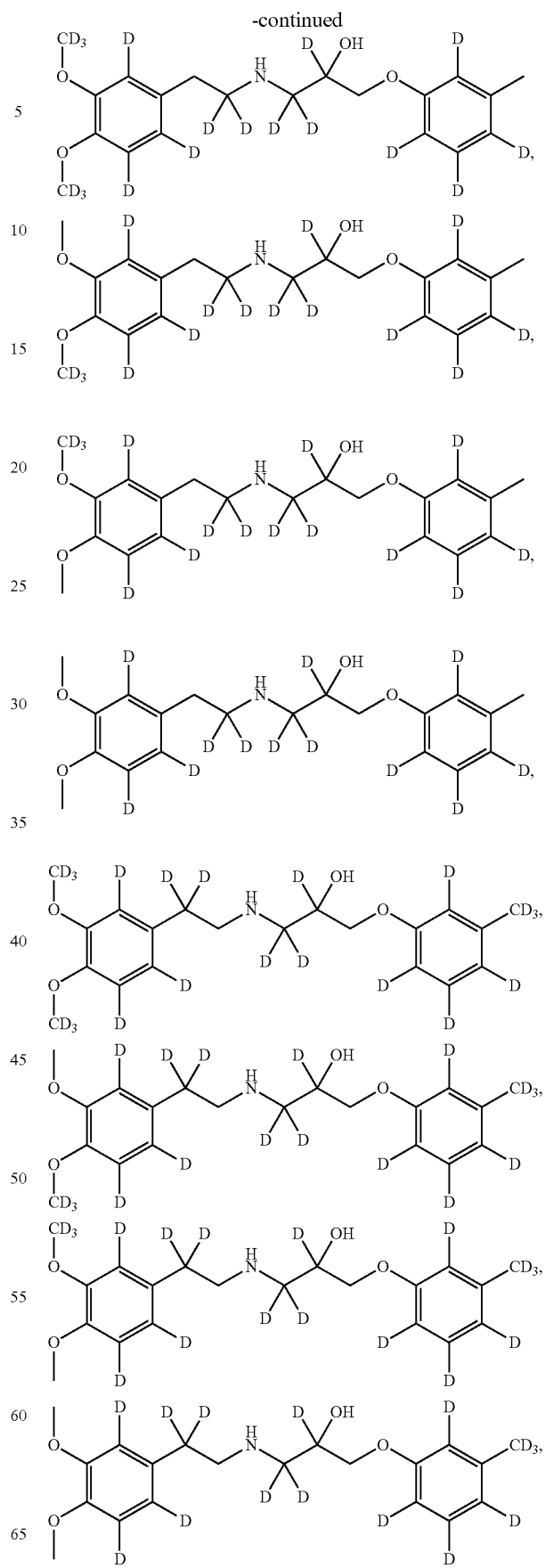

117
-continued
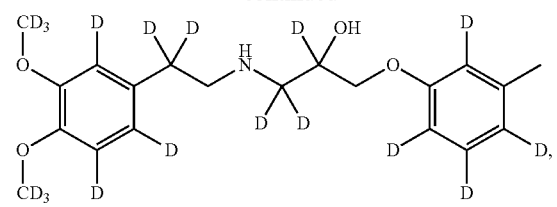
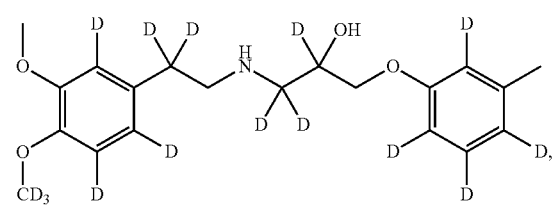
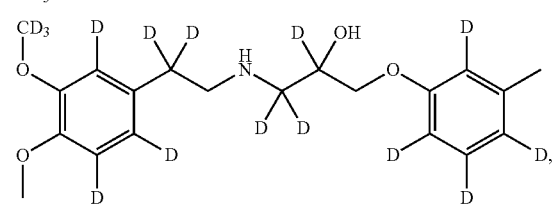
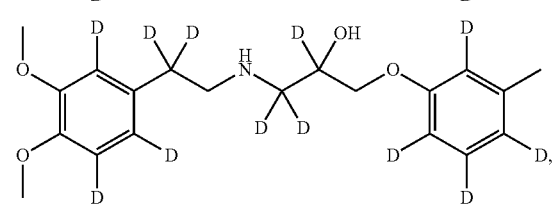
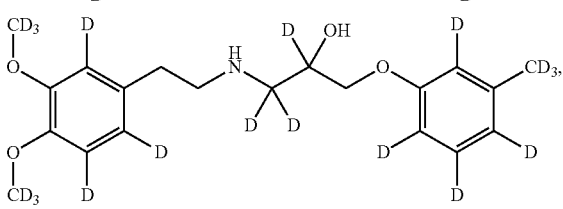
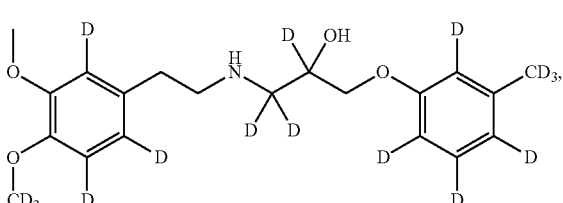
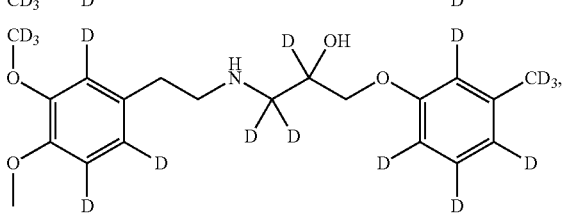
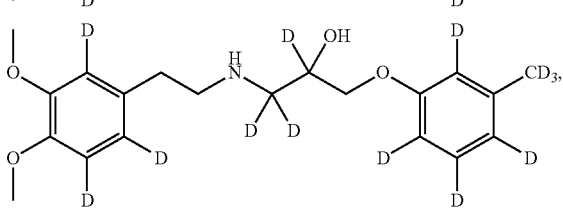
118
-continued
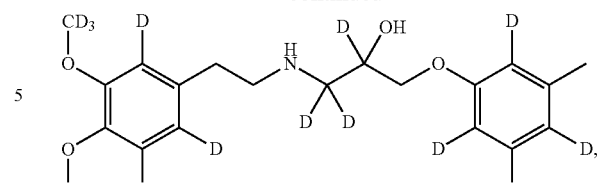
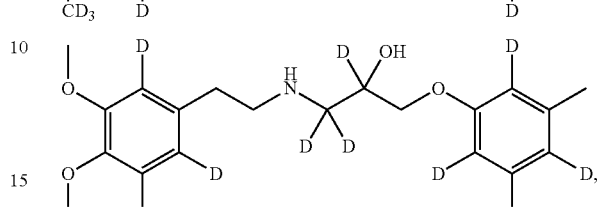
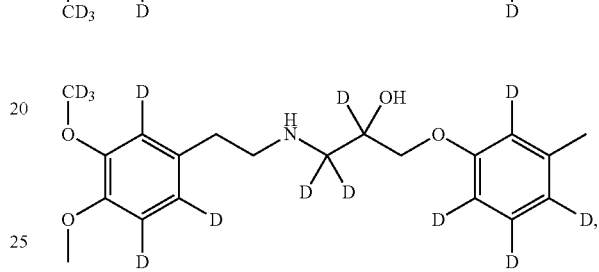
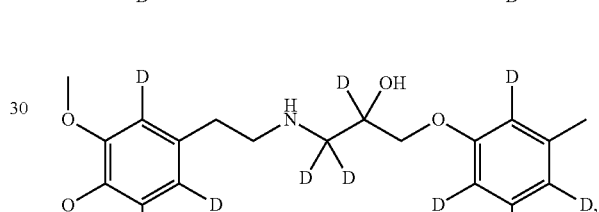
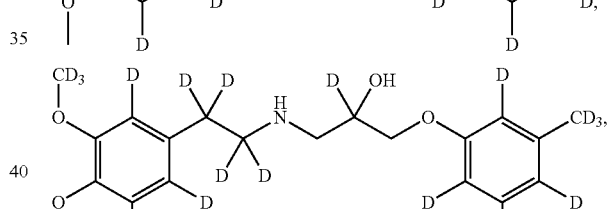
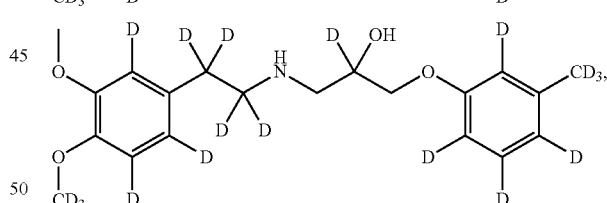
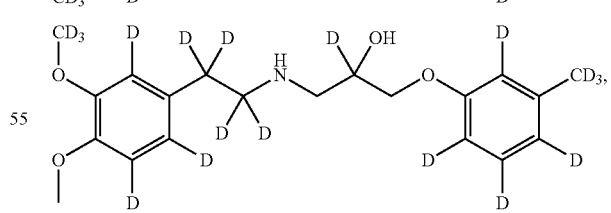
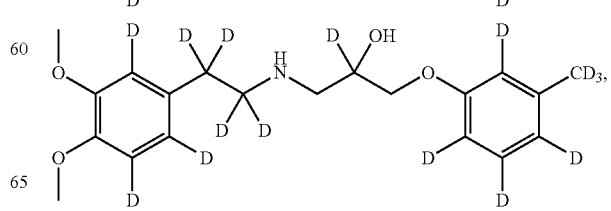

119
-continued
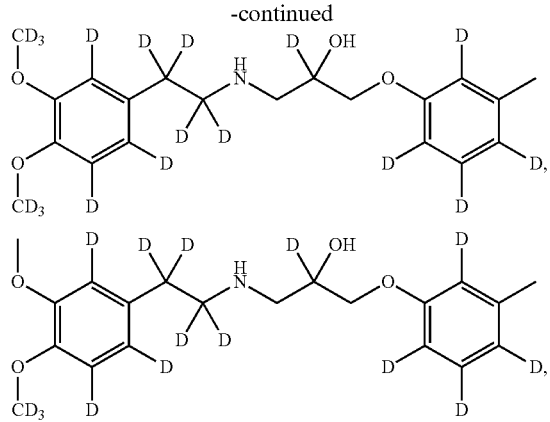
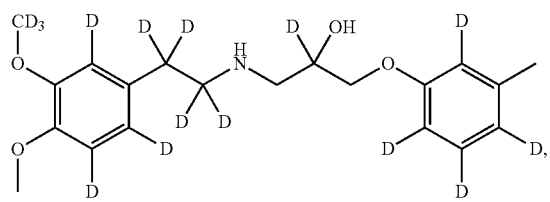
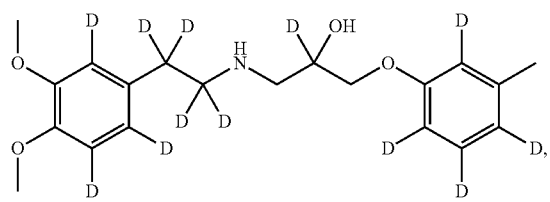
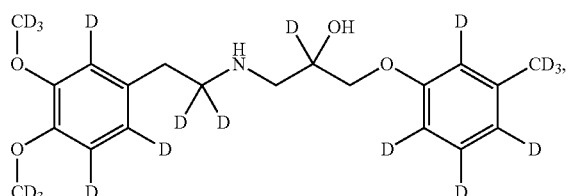
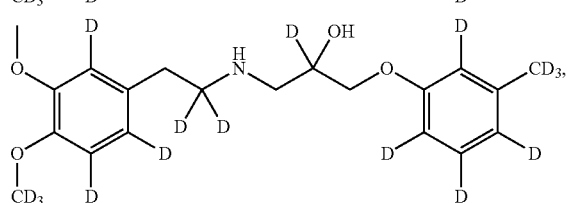
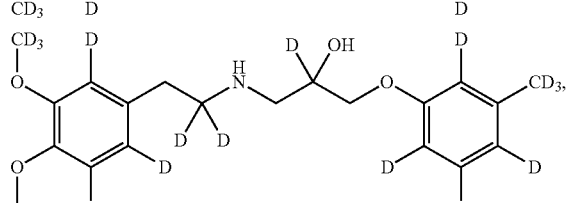
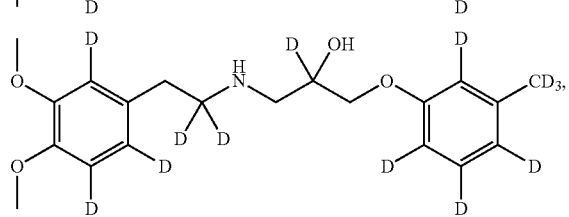
120
-continued
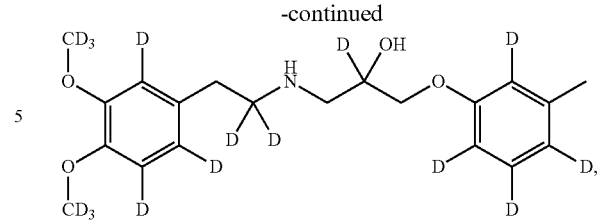
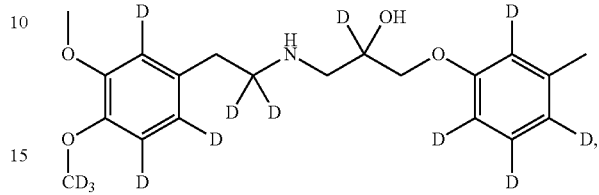
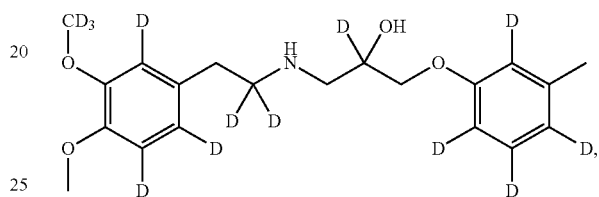
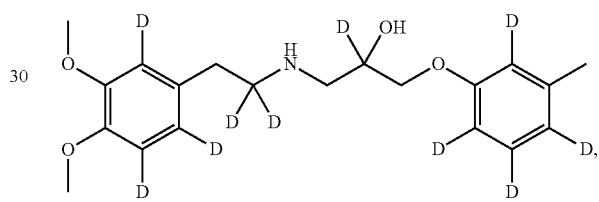
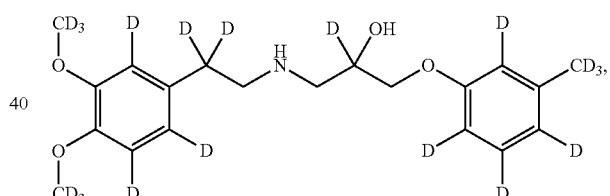
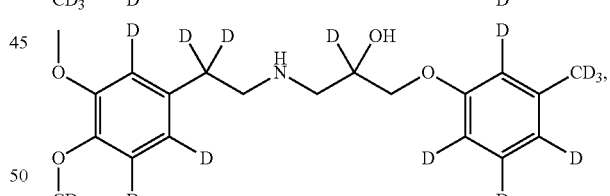
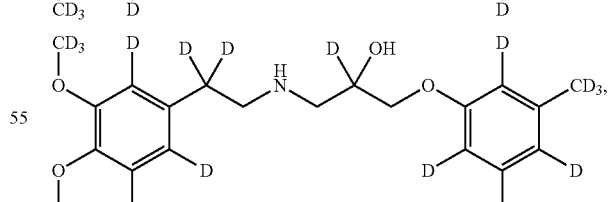
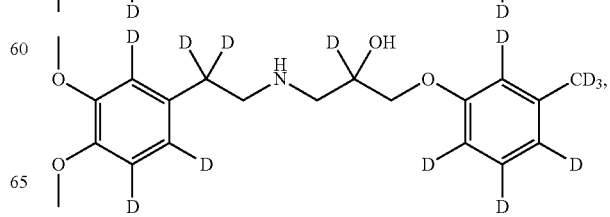

121
-continued
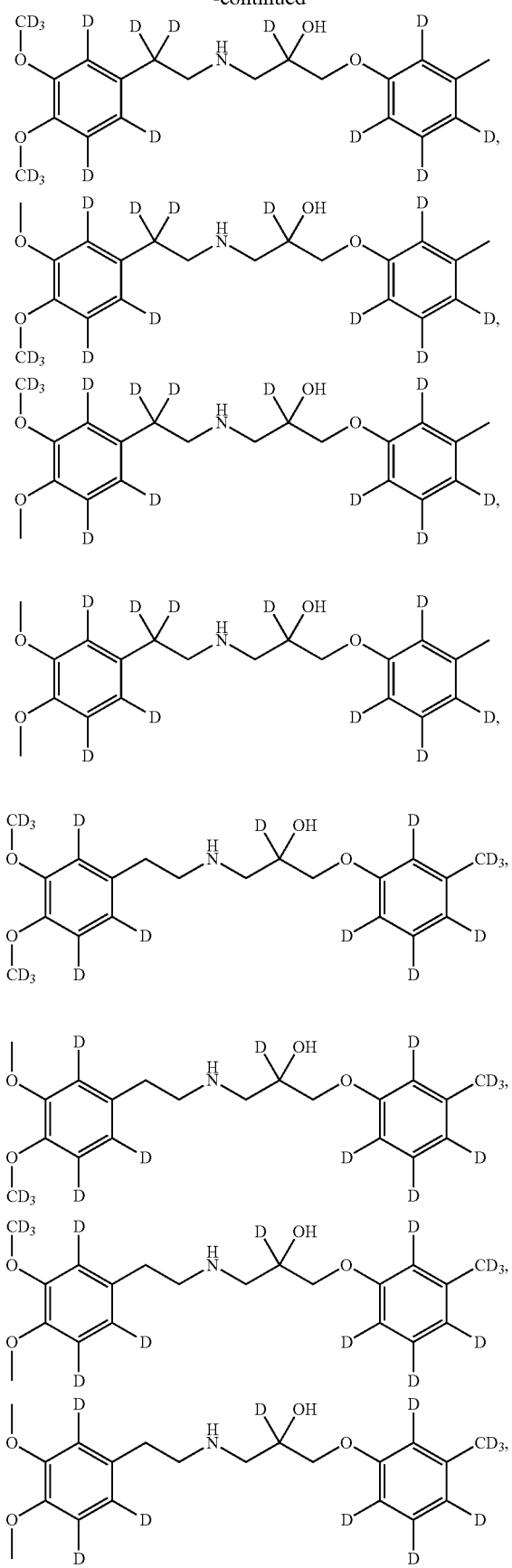
122
-continued
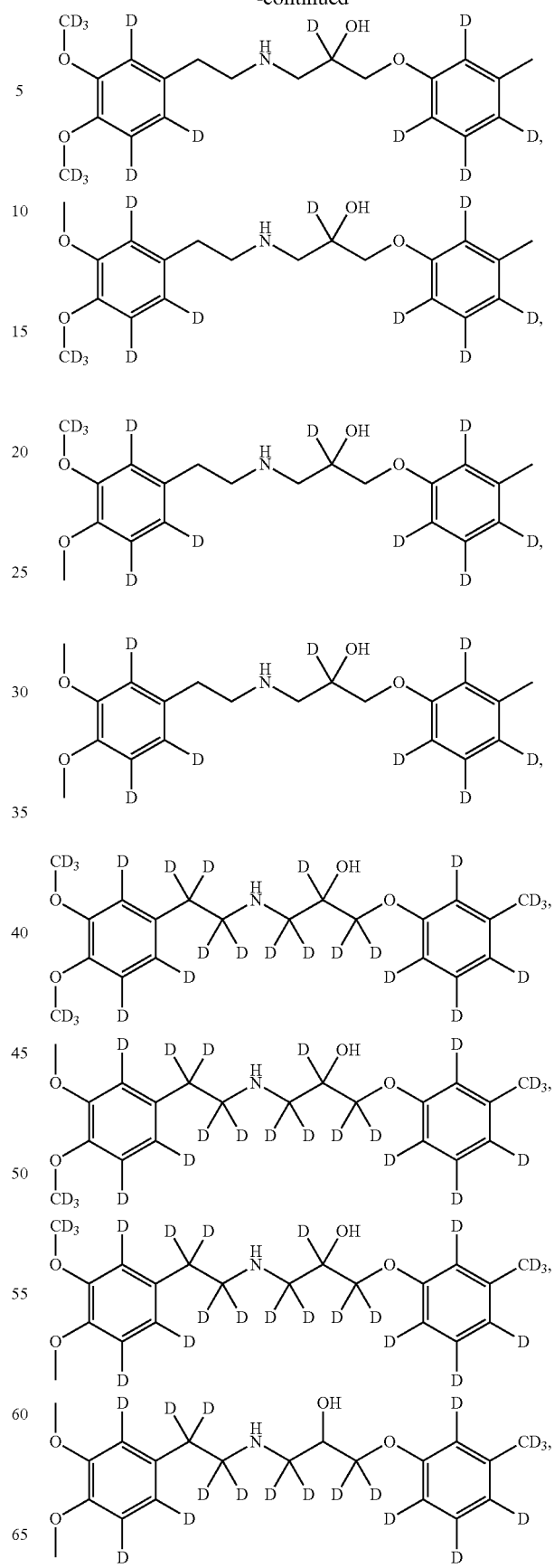

123
-continued
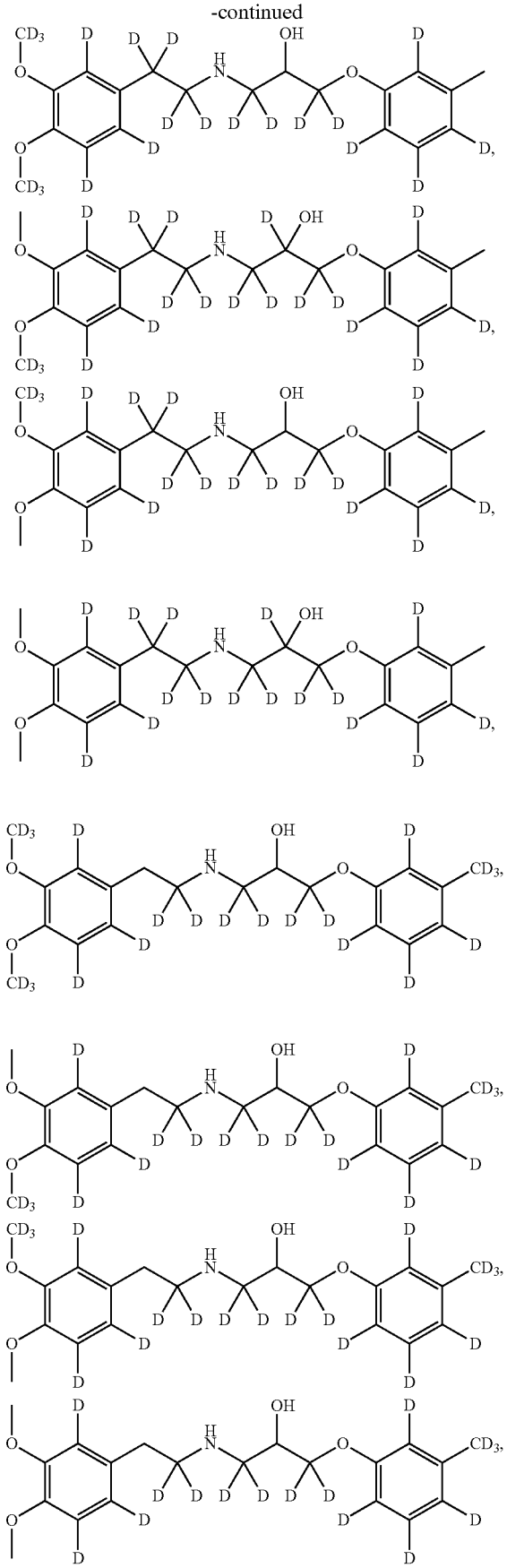
124
-continued
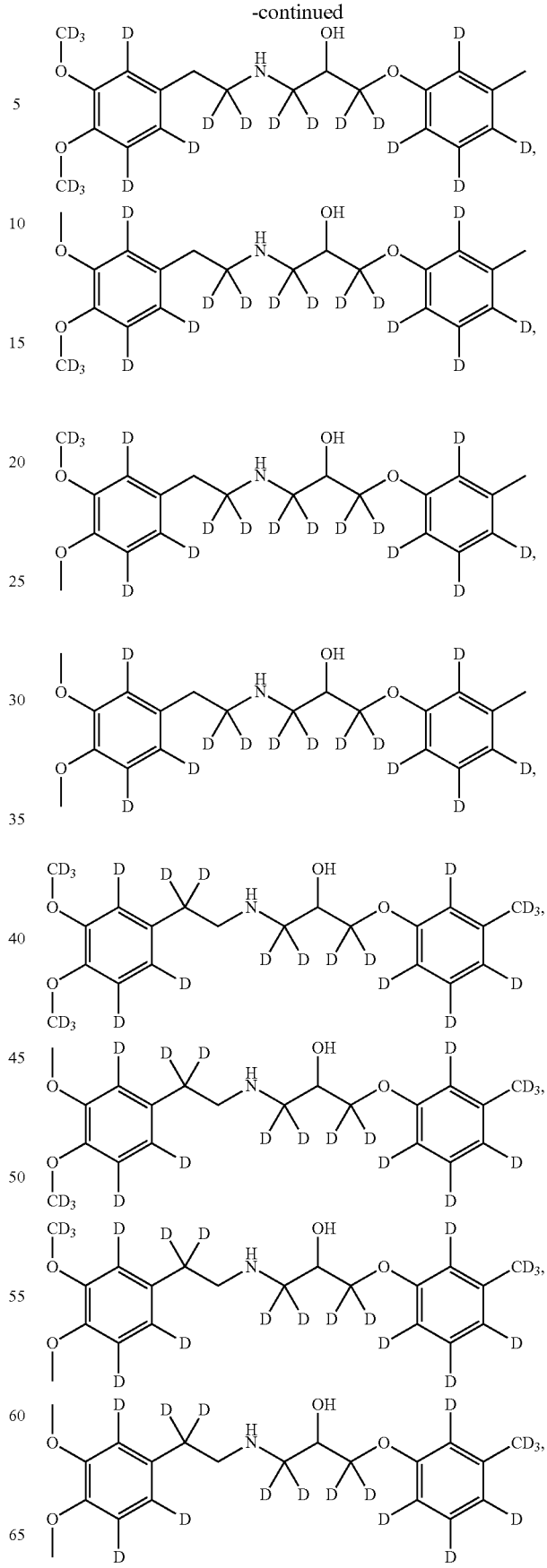

125
-continued
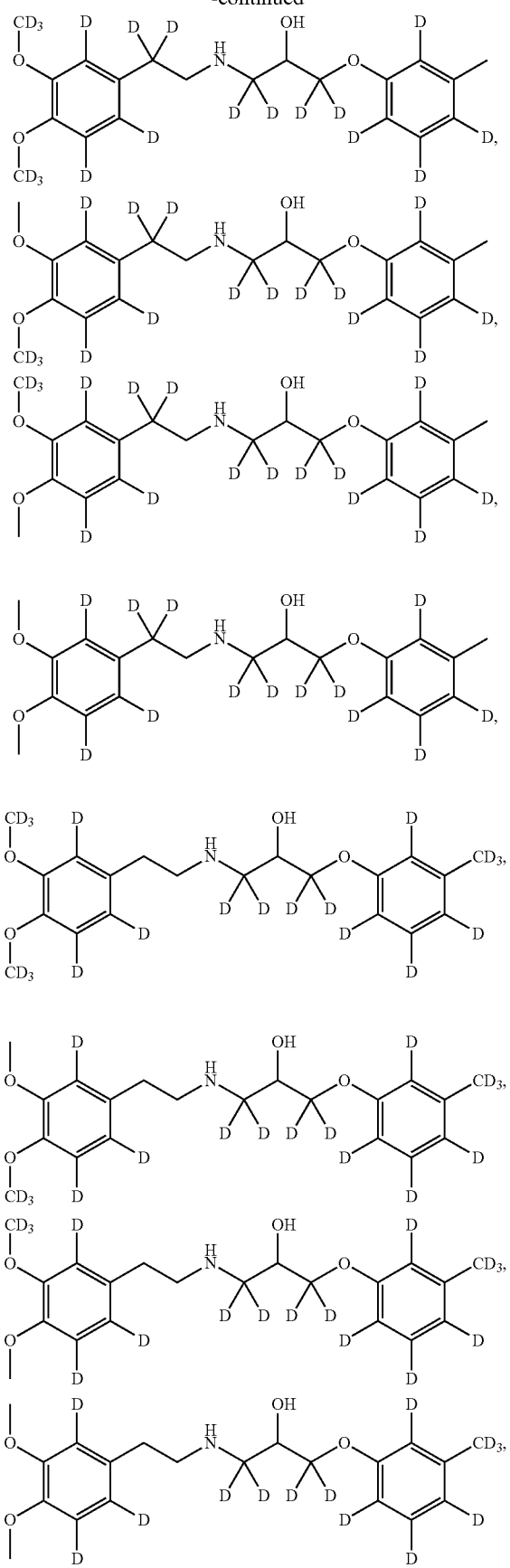
126
-continued
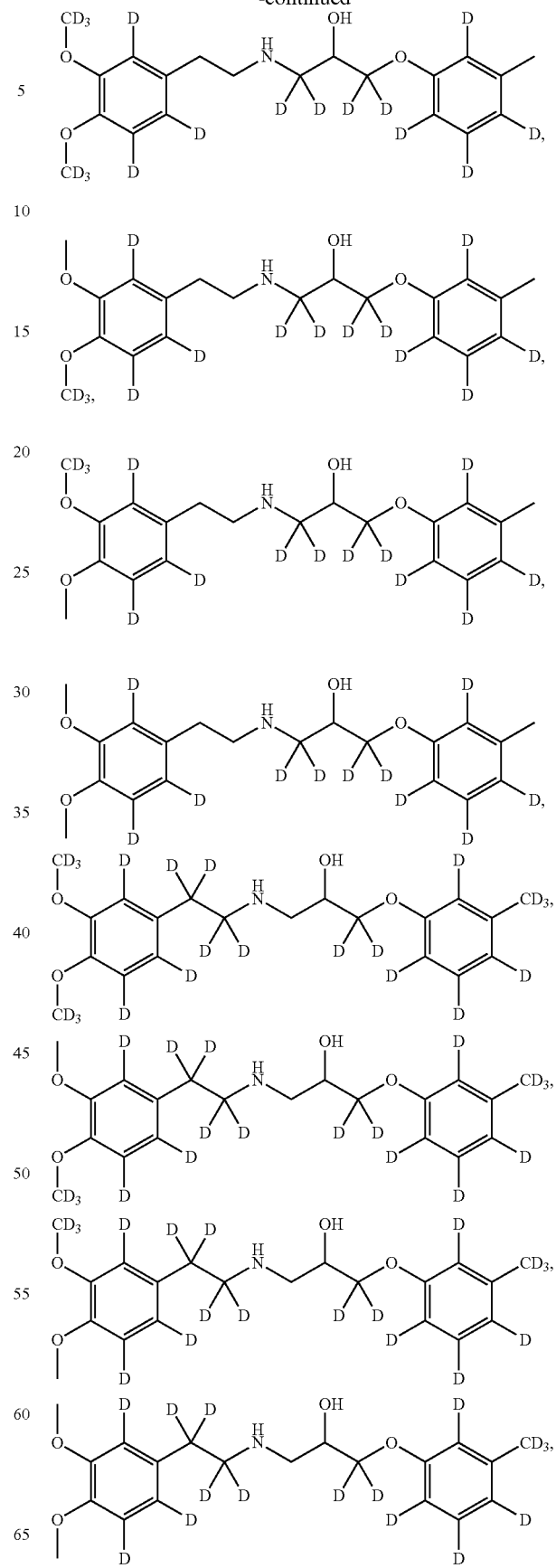

127
-continued
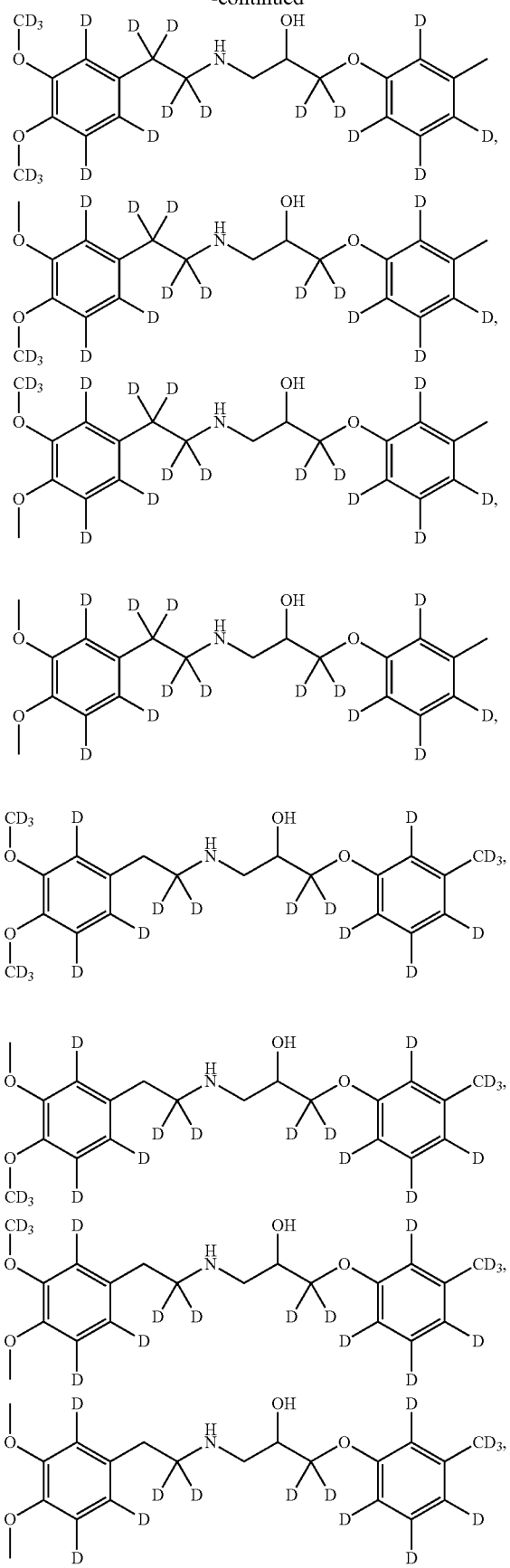
128
-continued
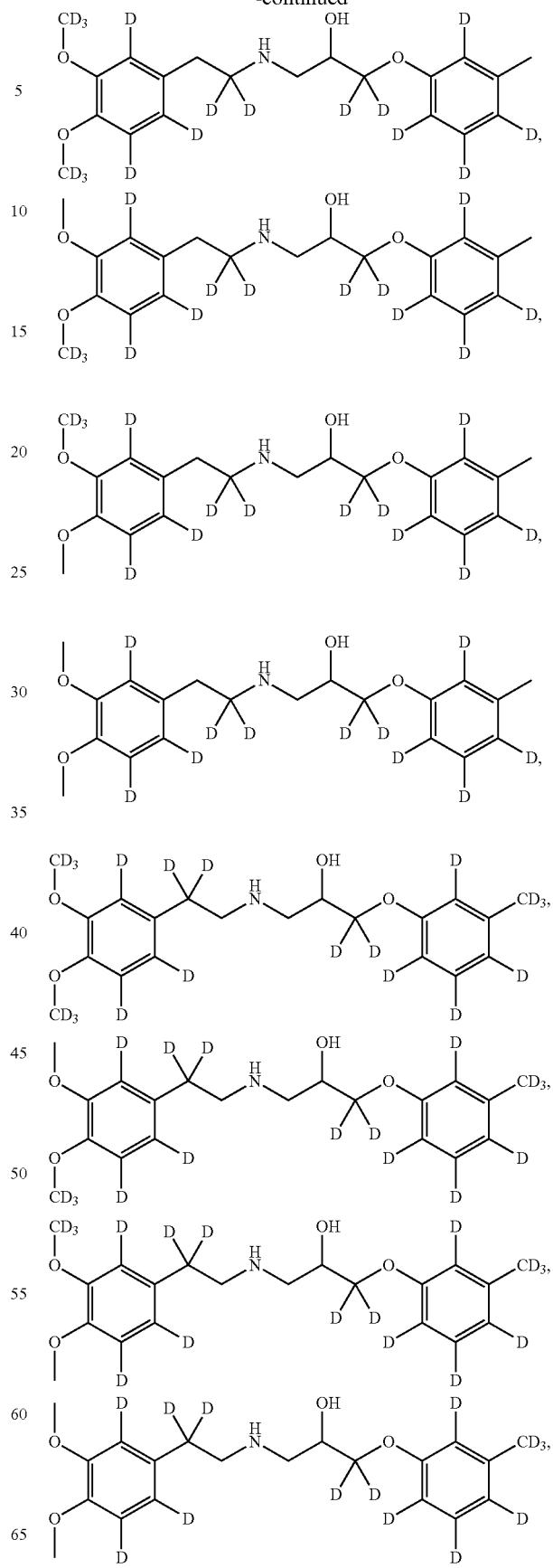

-continued
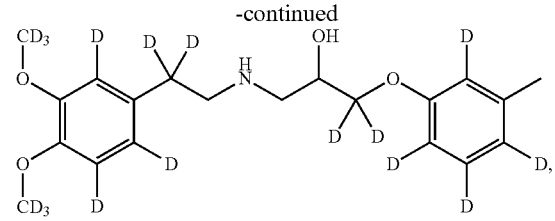
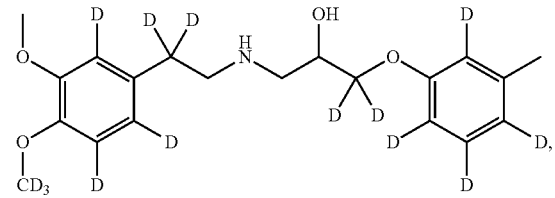
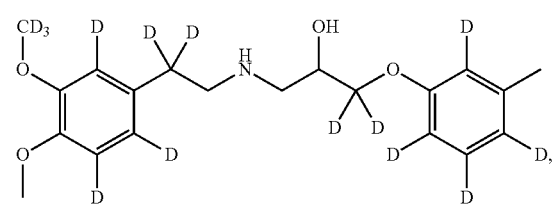
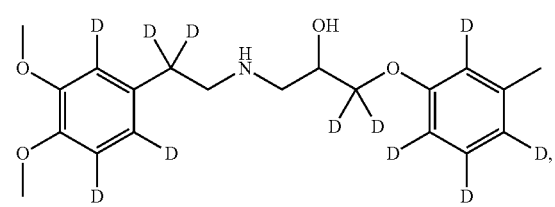
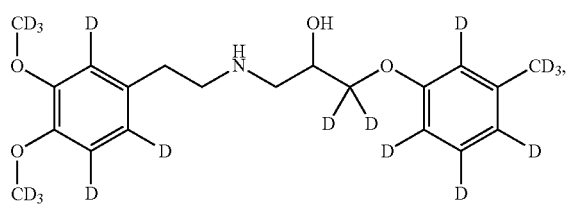
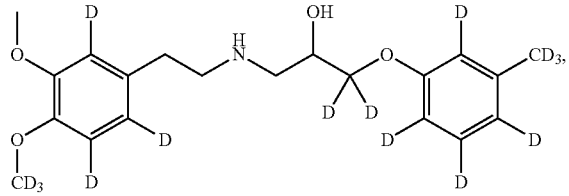
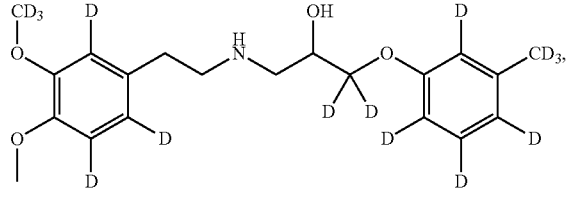
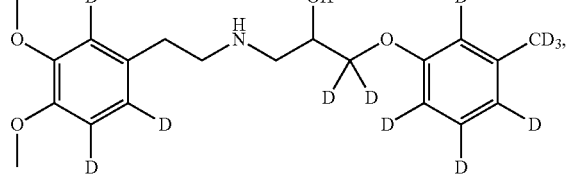
-continued
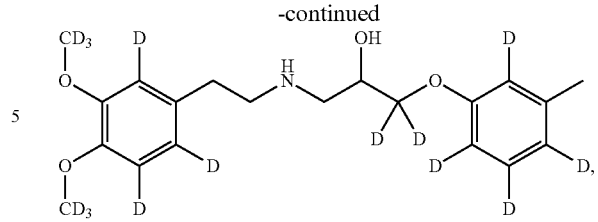
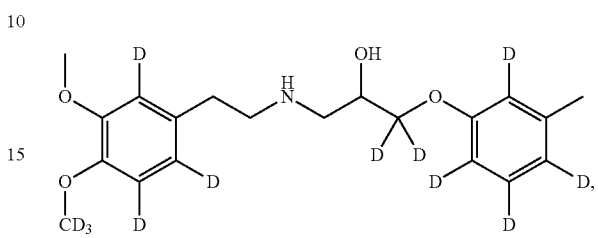
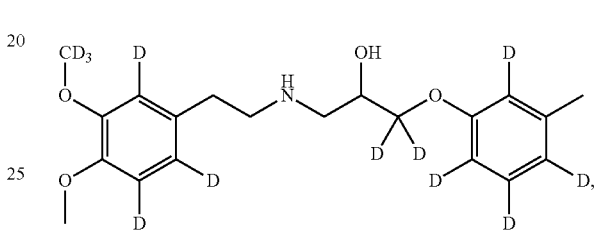
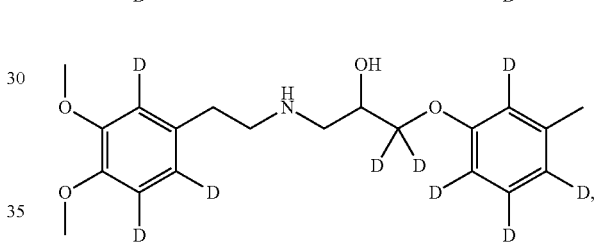
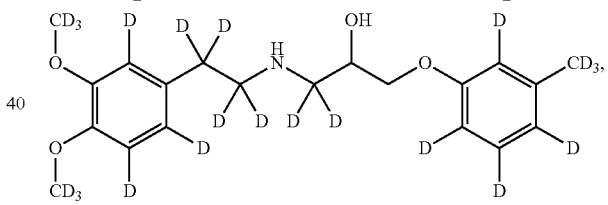
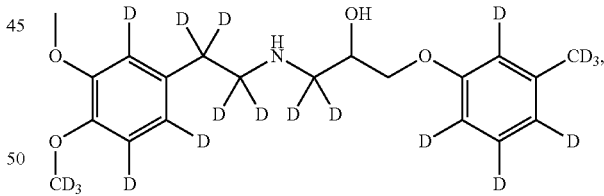
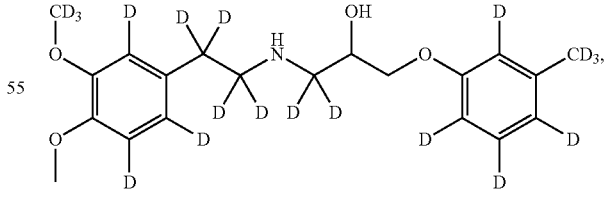
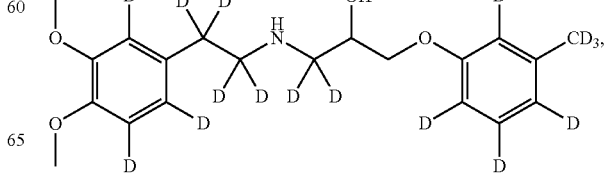

131
-continued
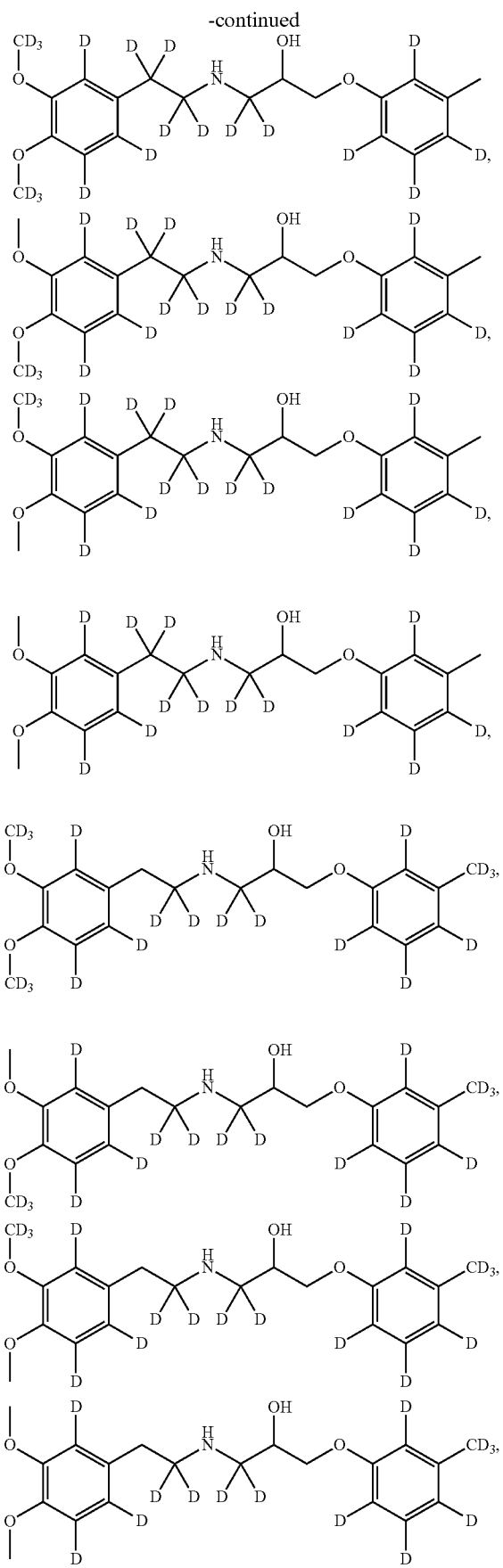
132
-continued
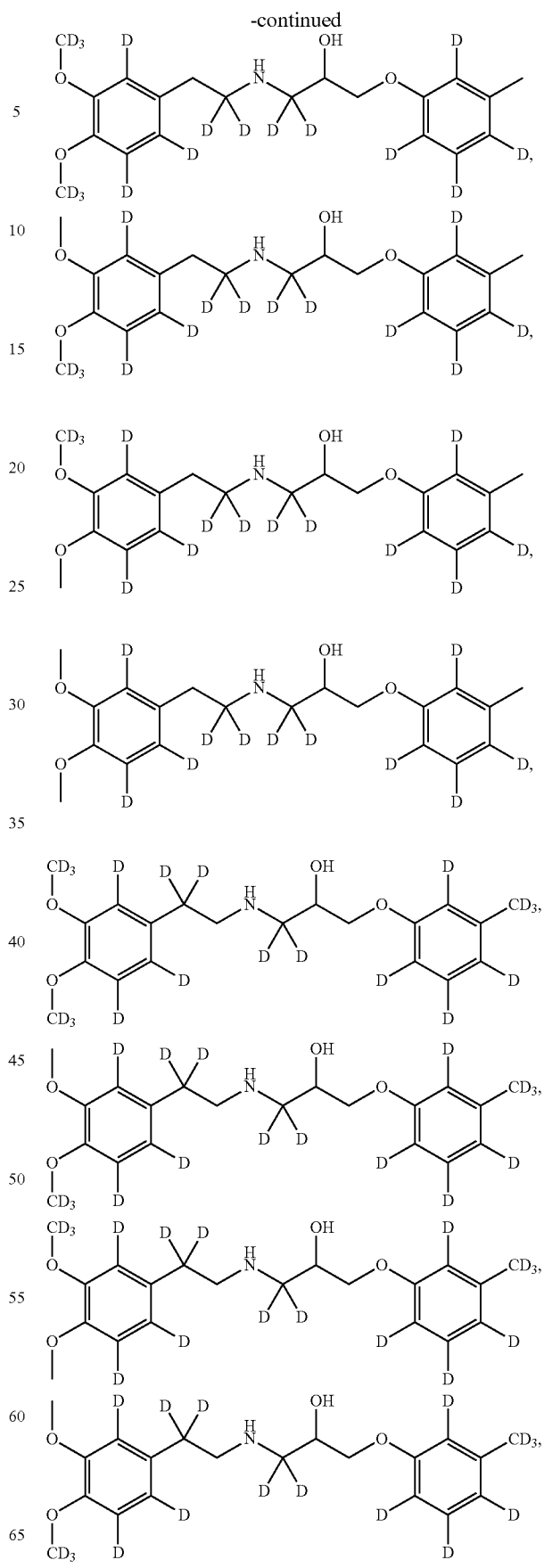

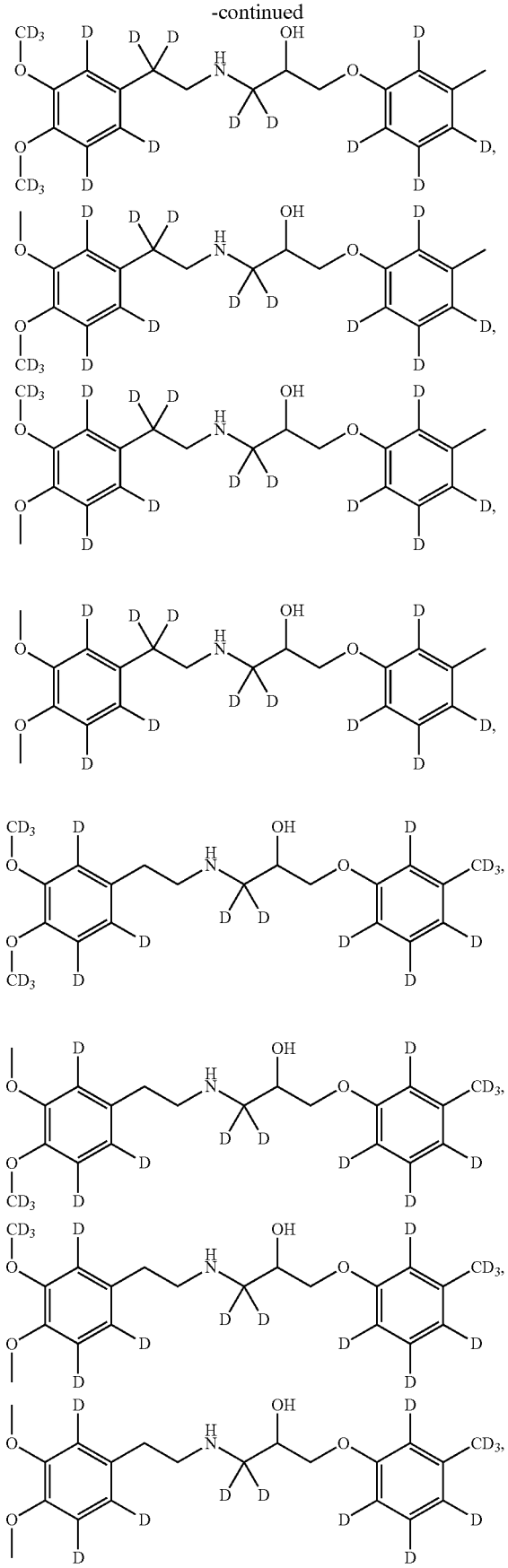
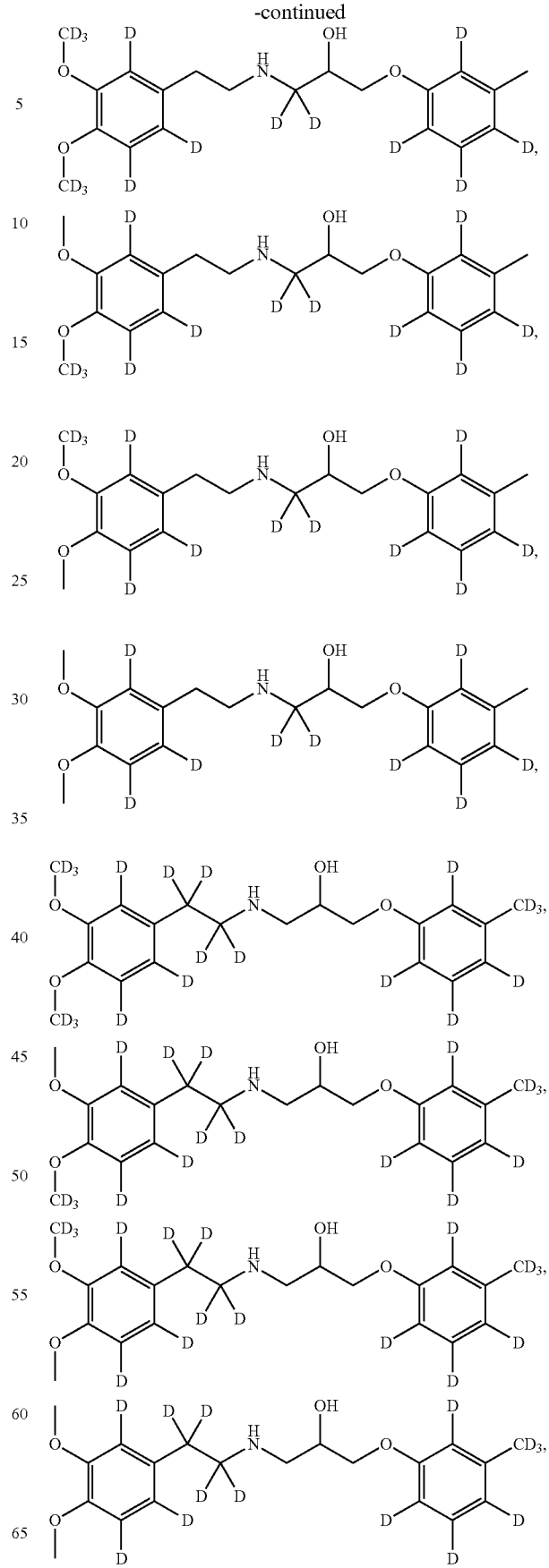

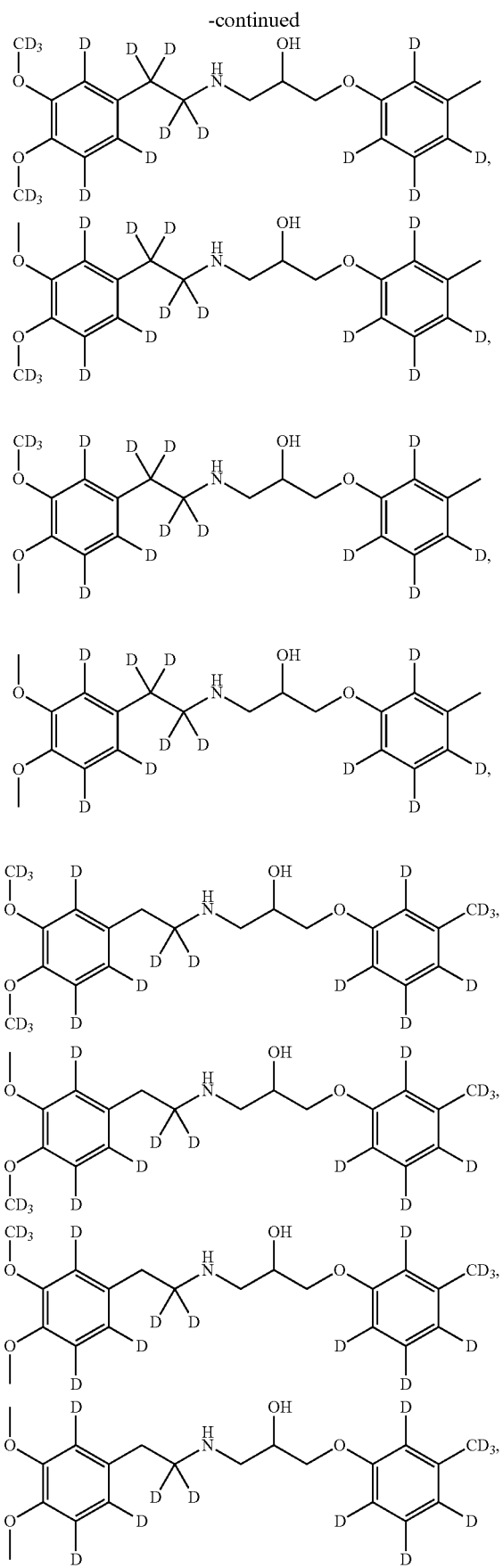
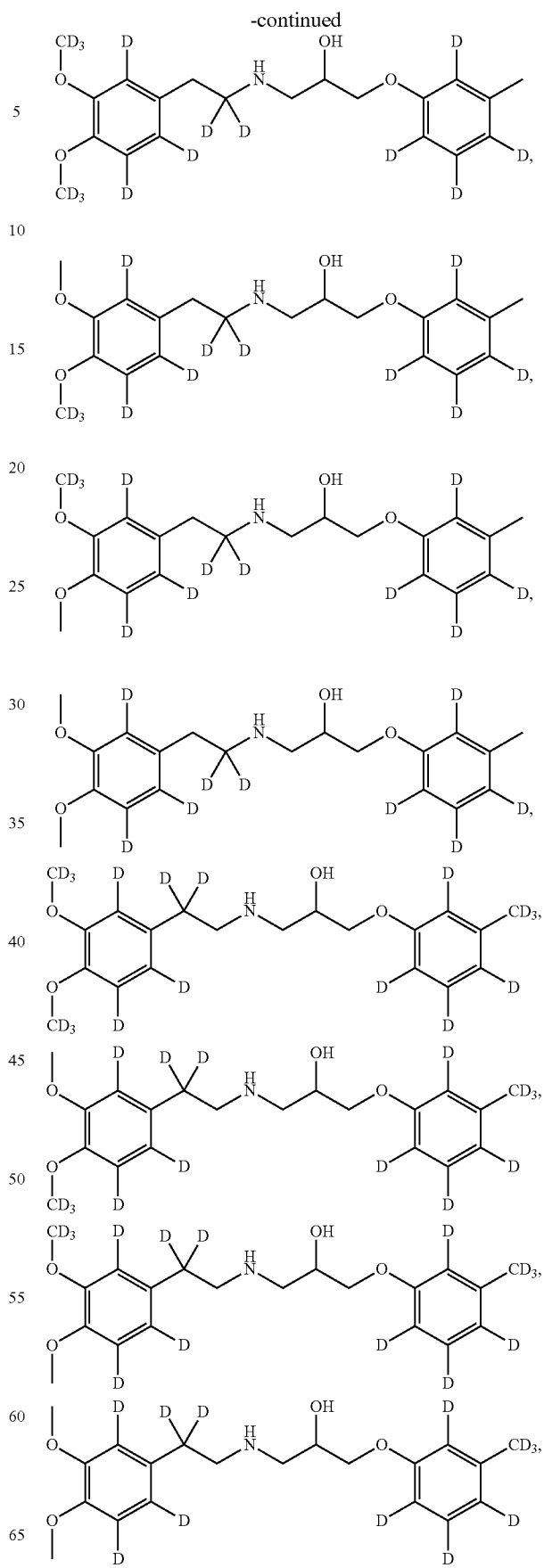

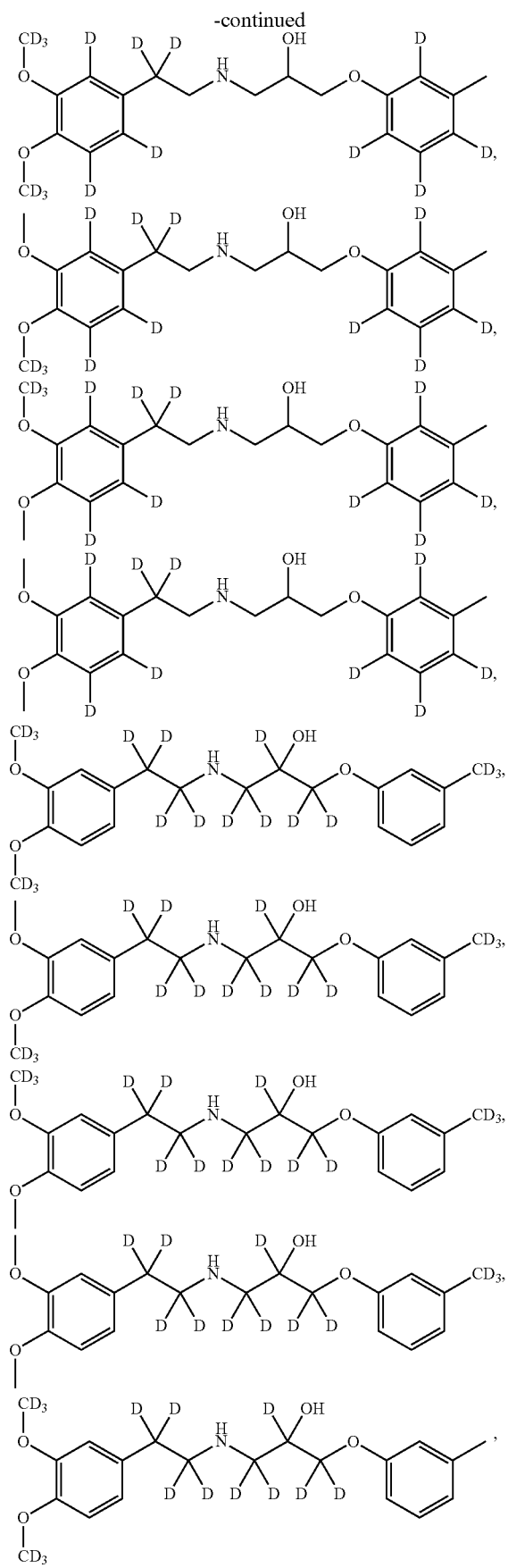
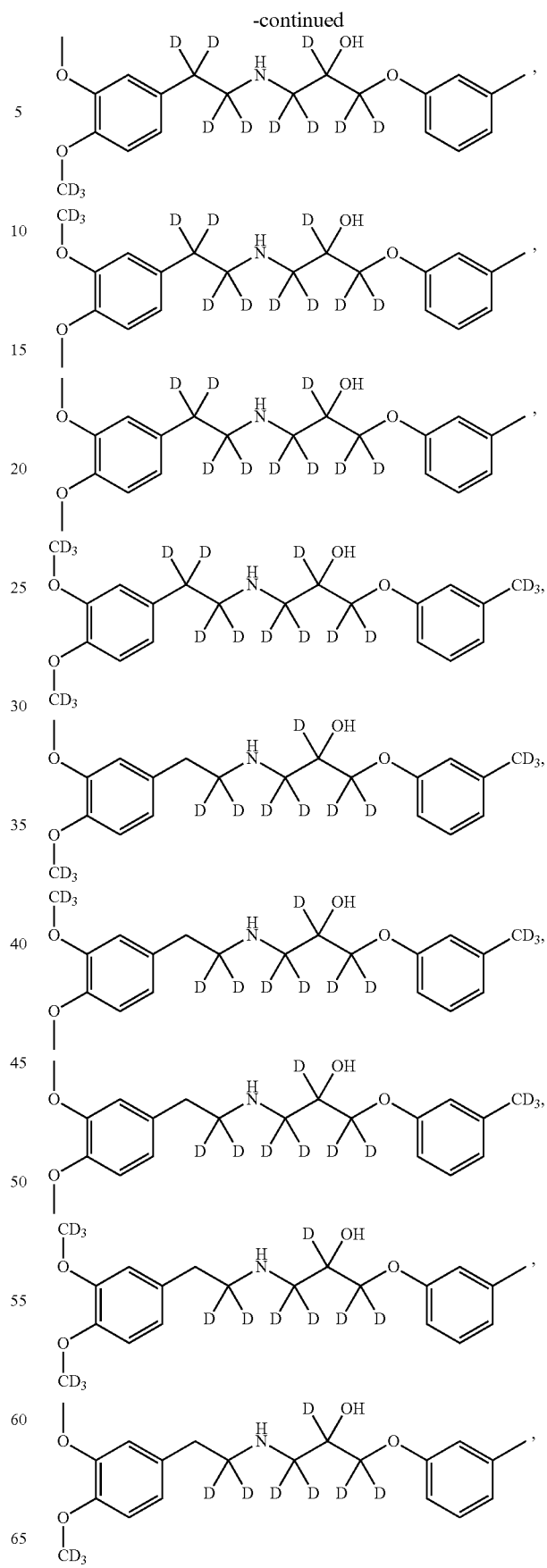

139
-continued
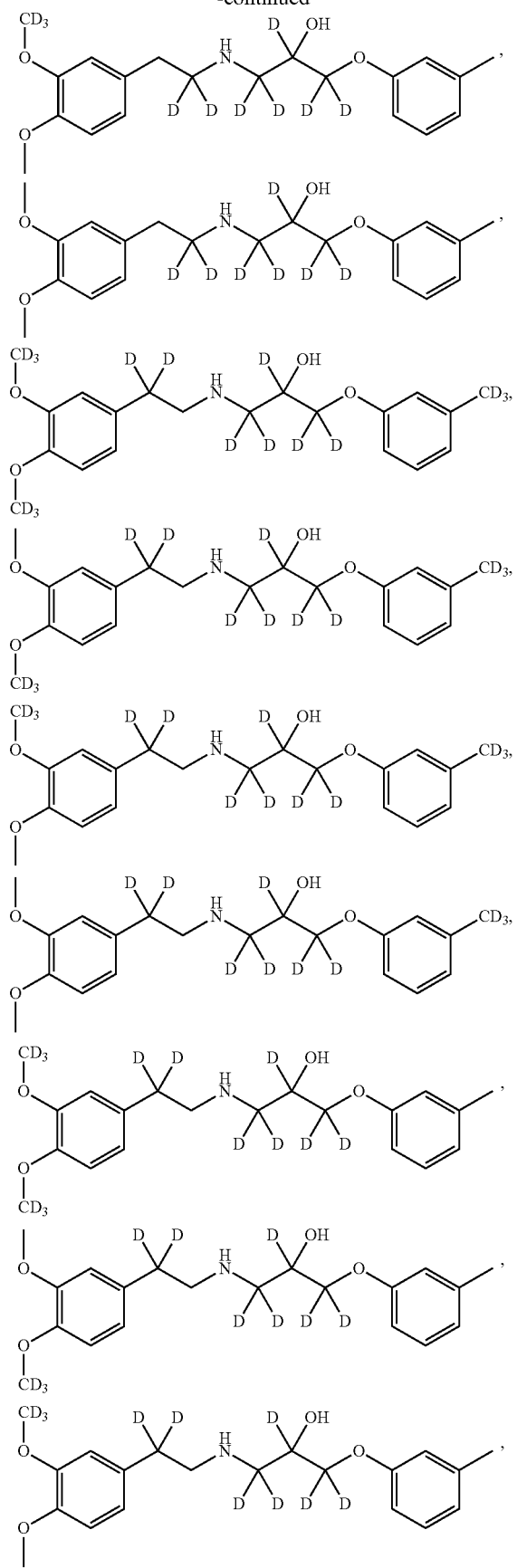
140
-continued
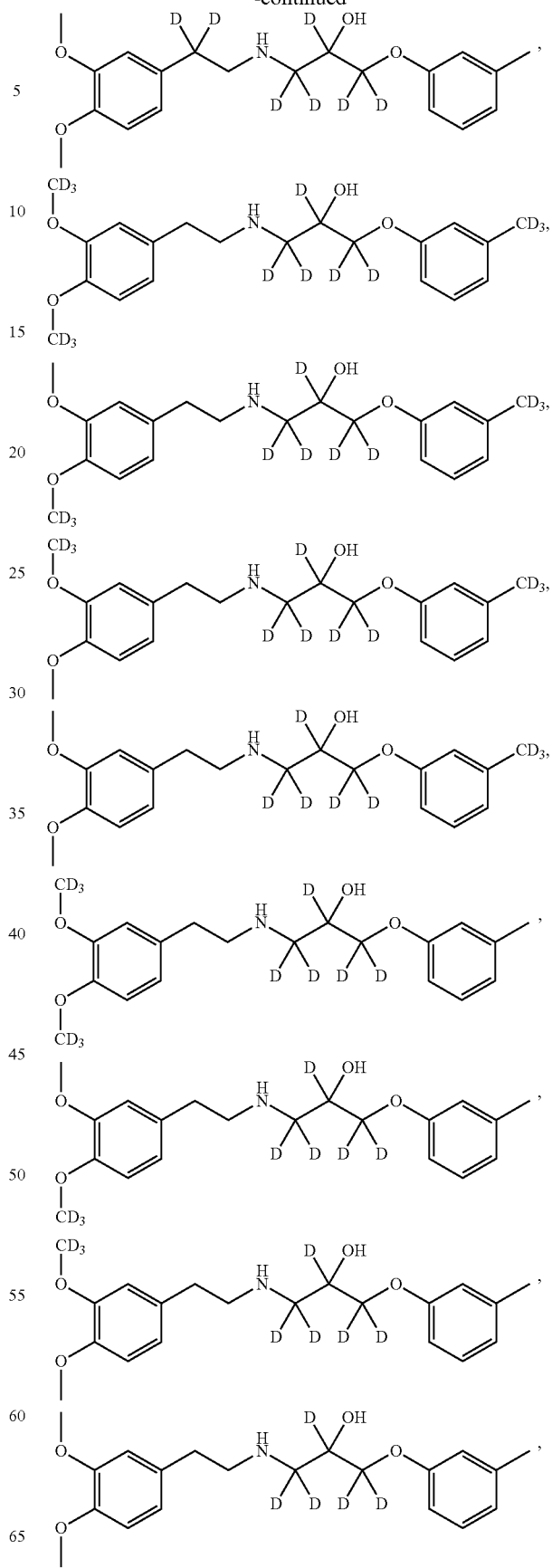

-continued
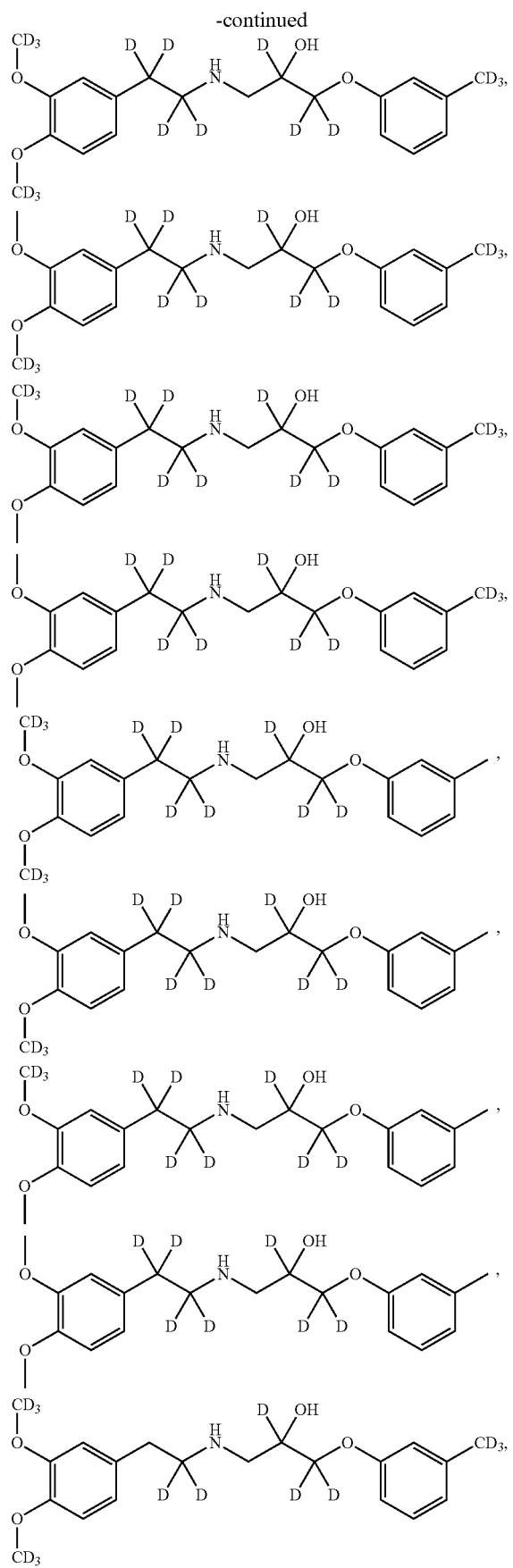
-continued
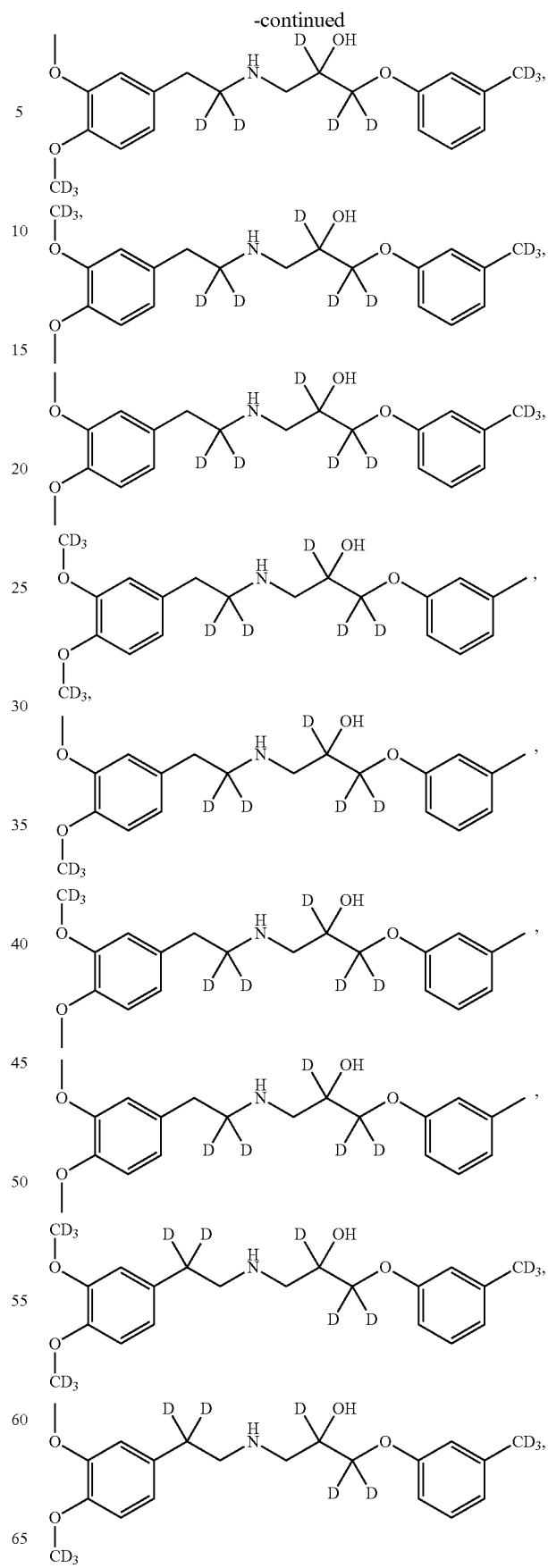

-continued
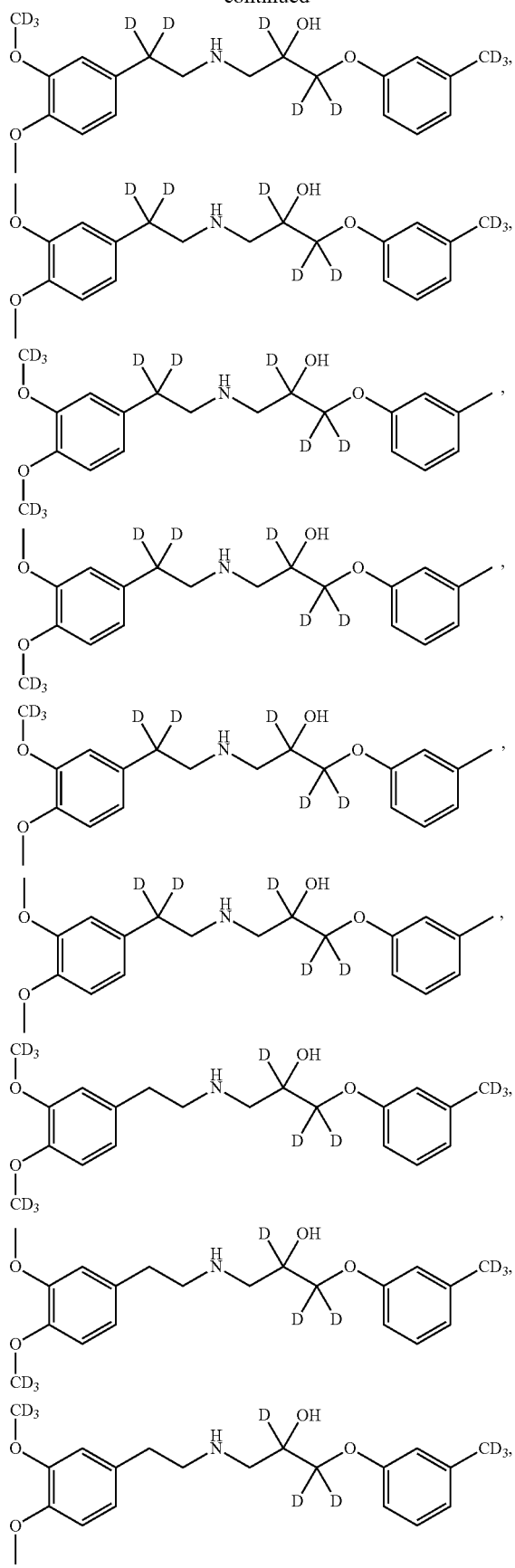
-continued
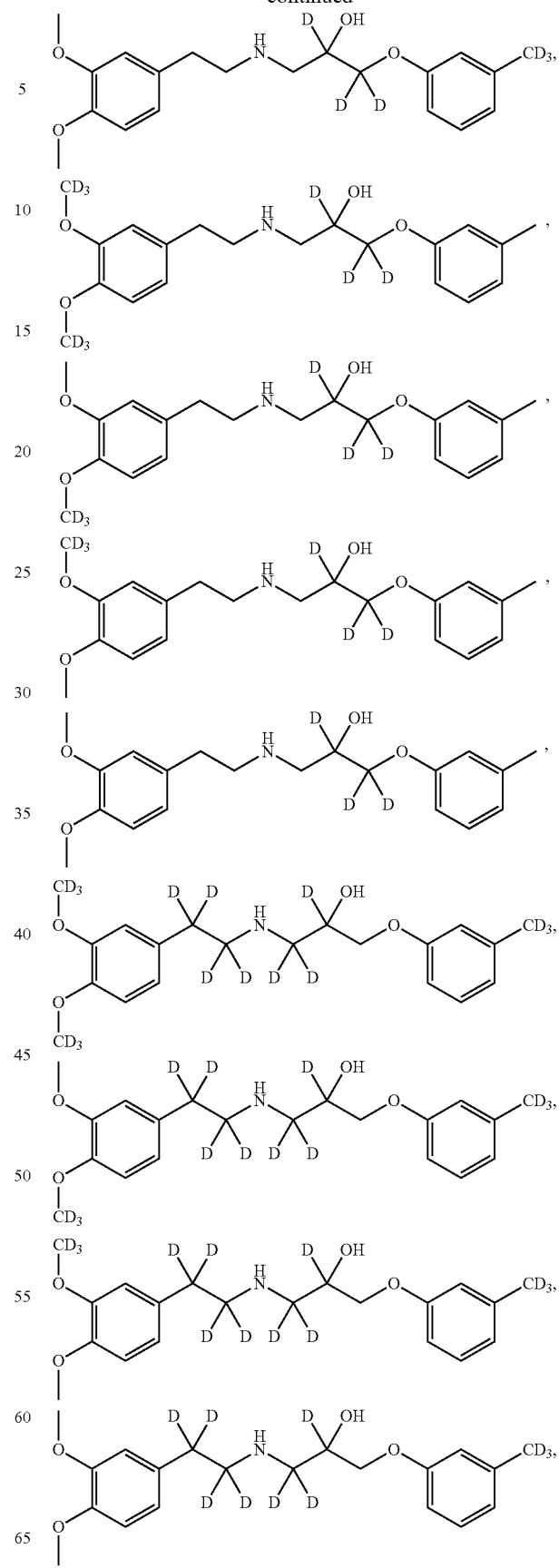

-continued
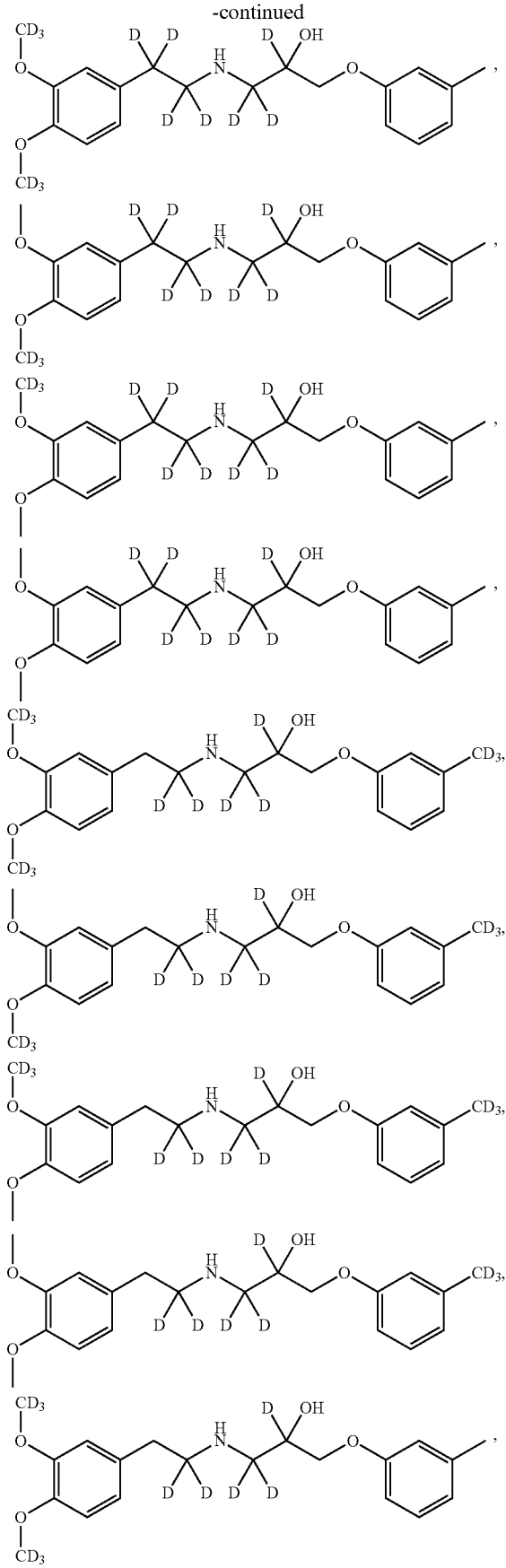
-continued
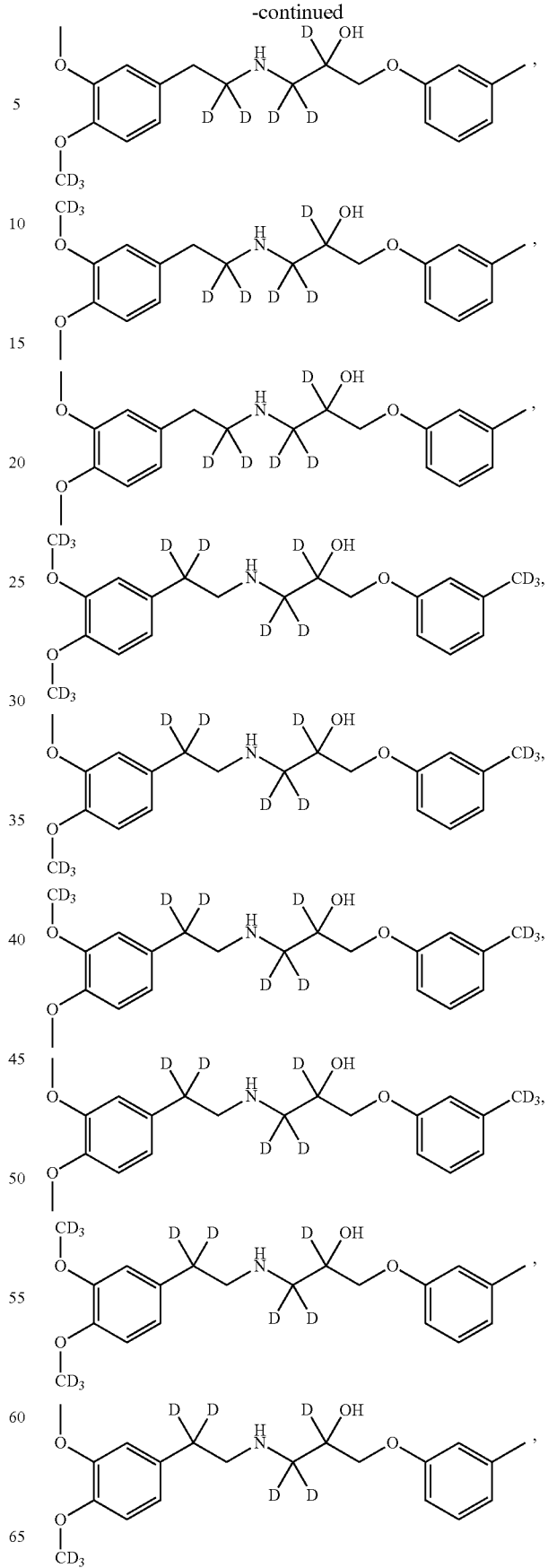

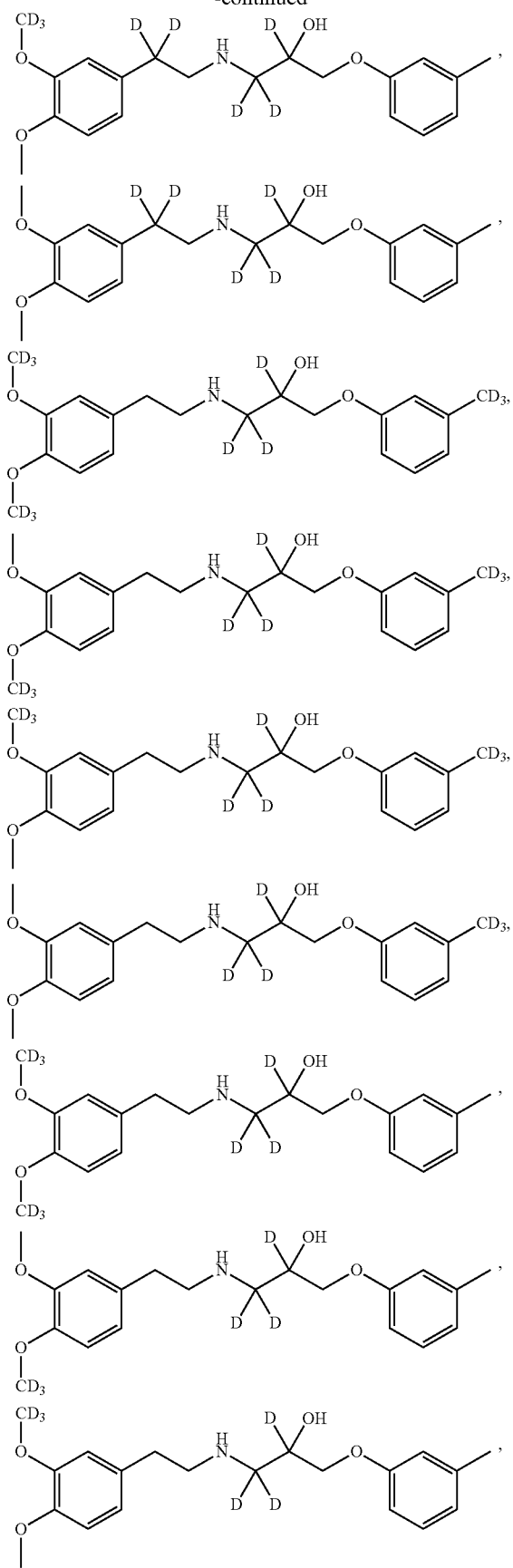
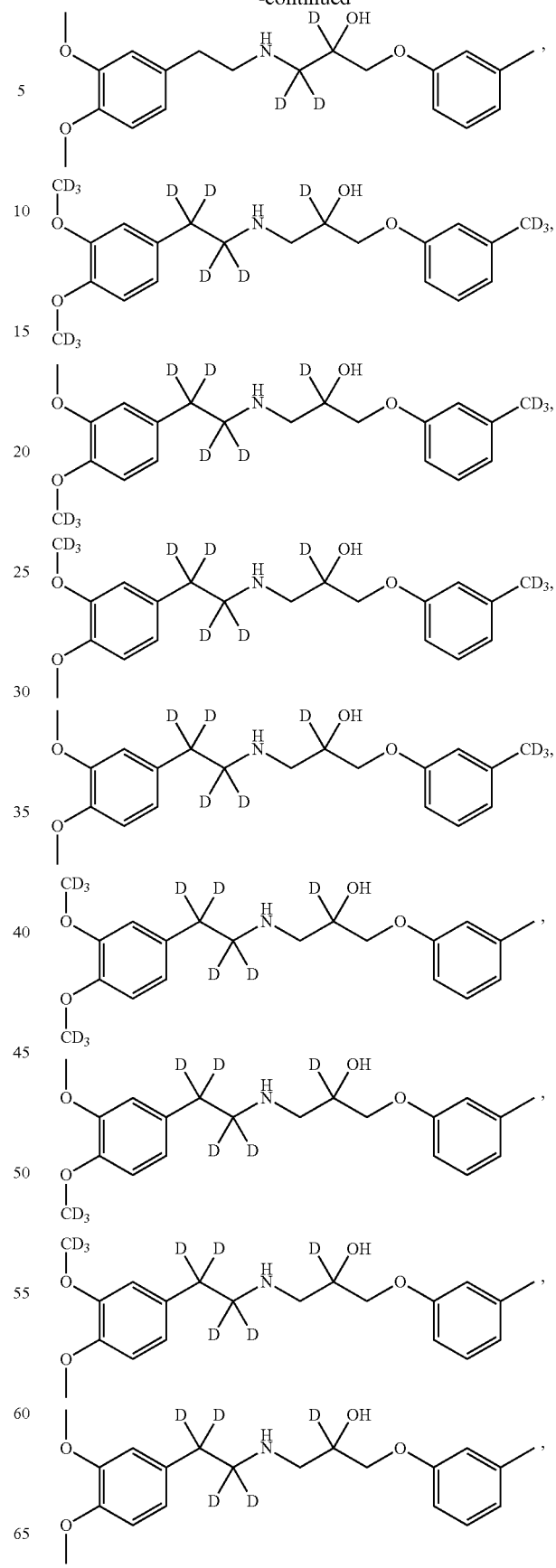

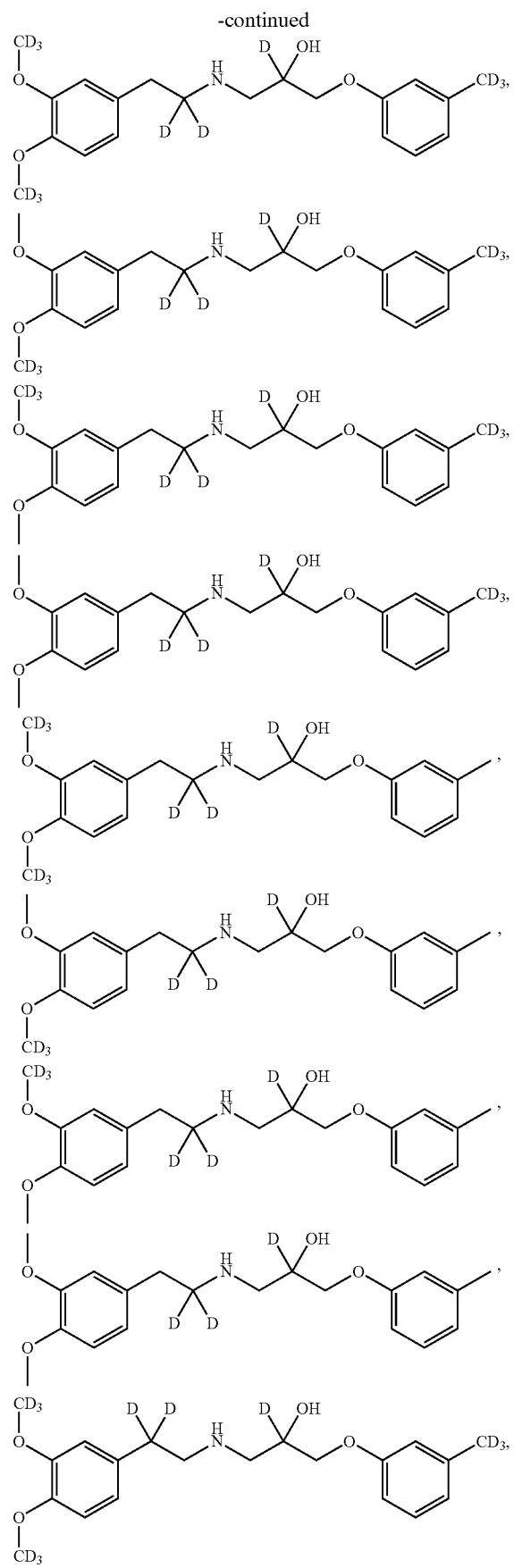
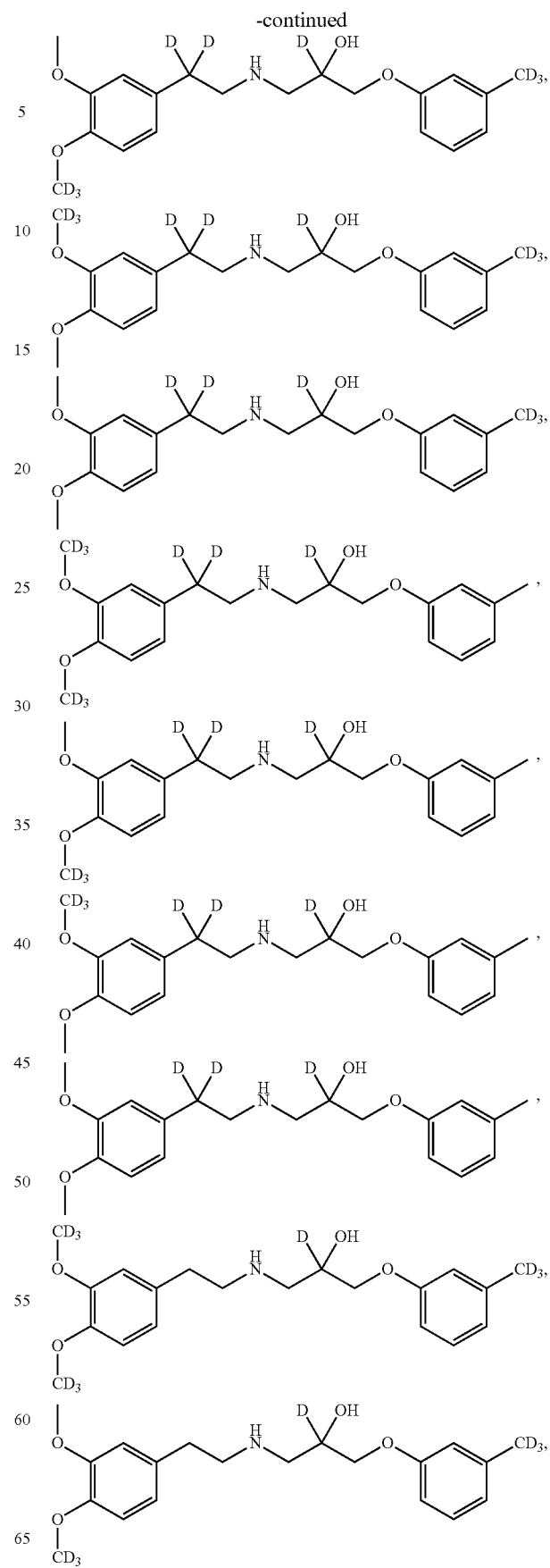

151
-continued
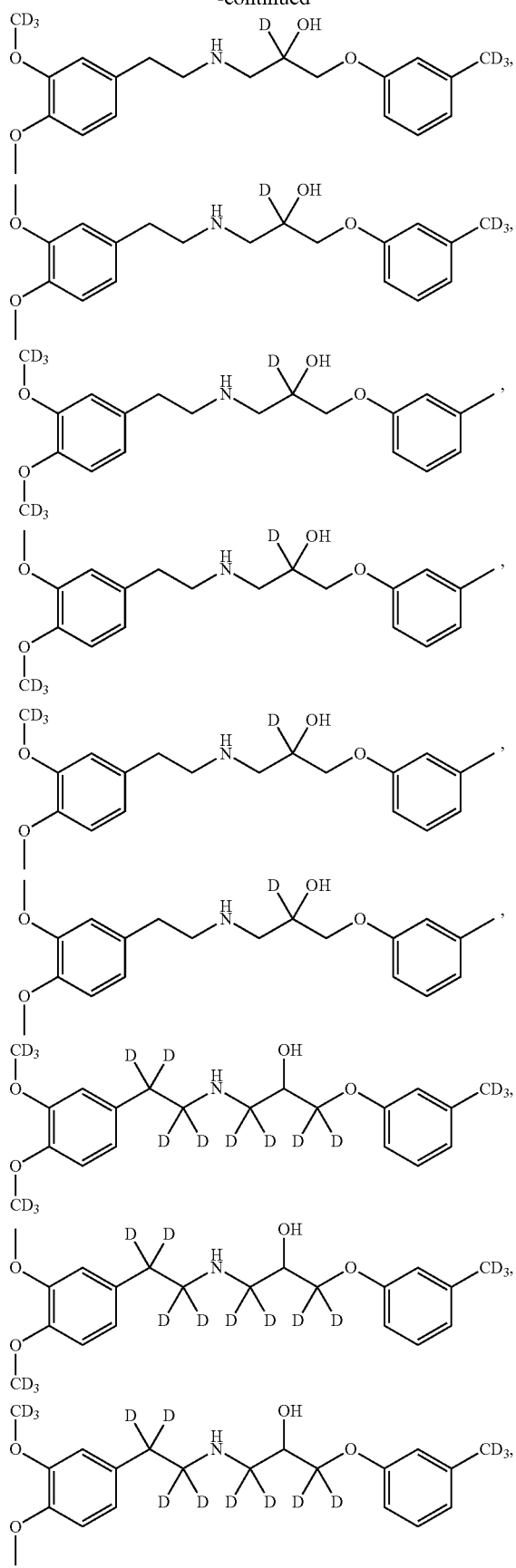
152
-continued
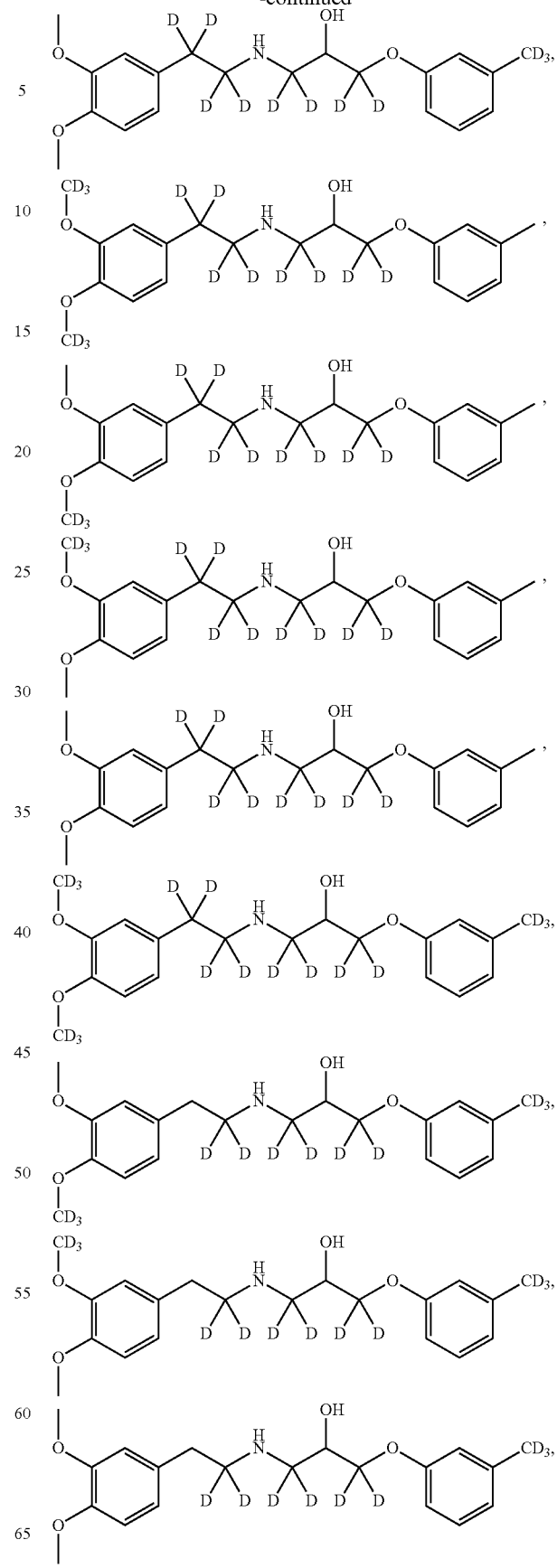

153
-continued
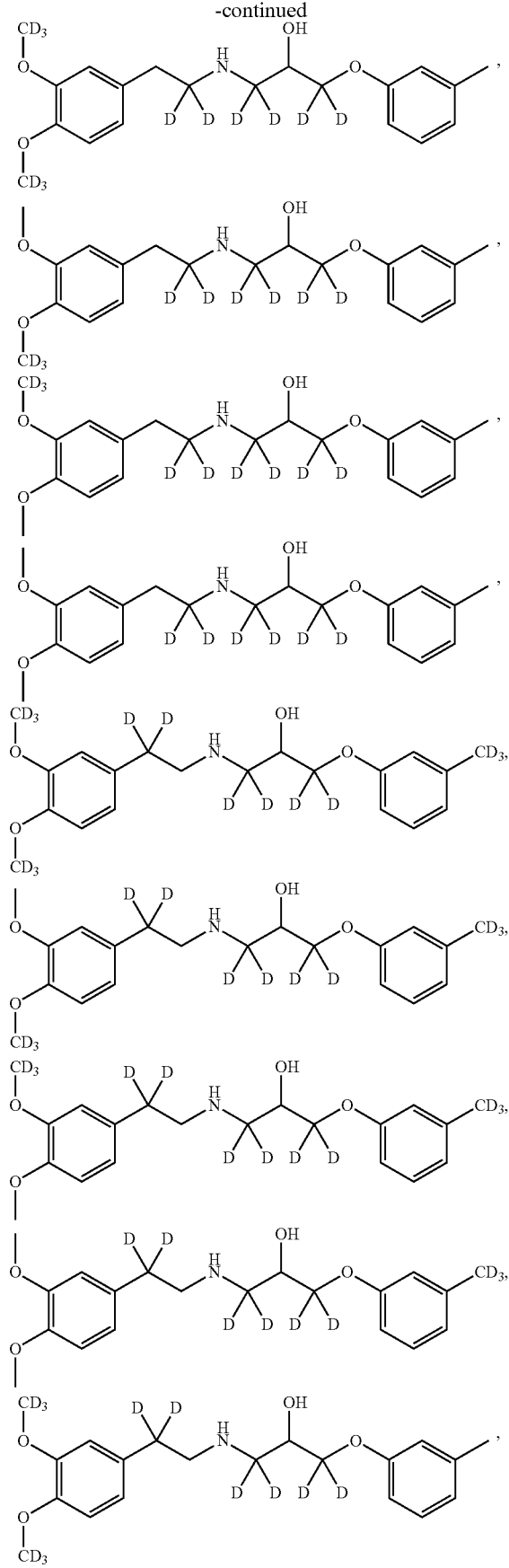
154
-continued
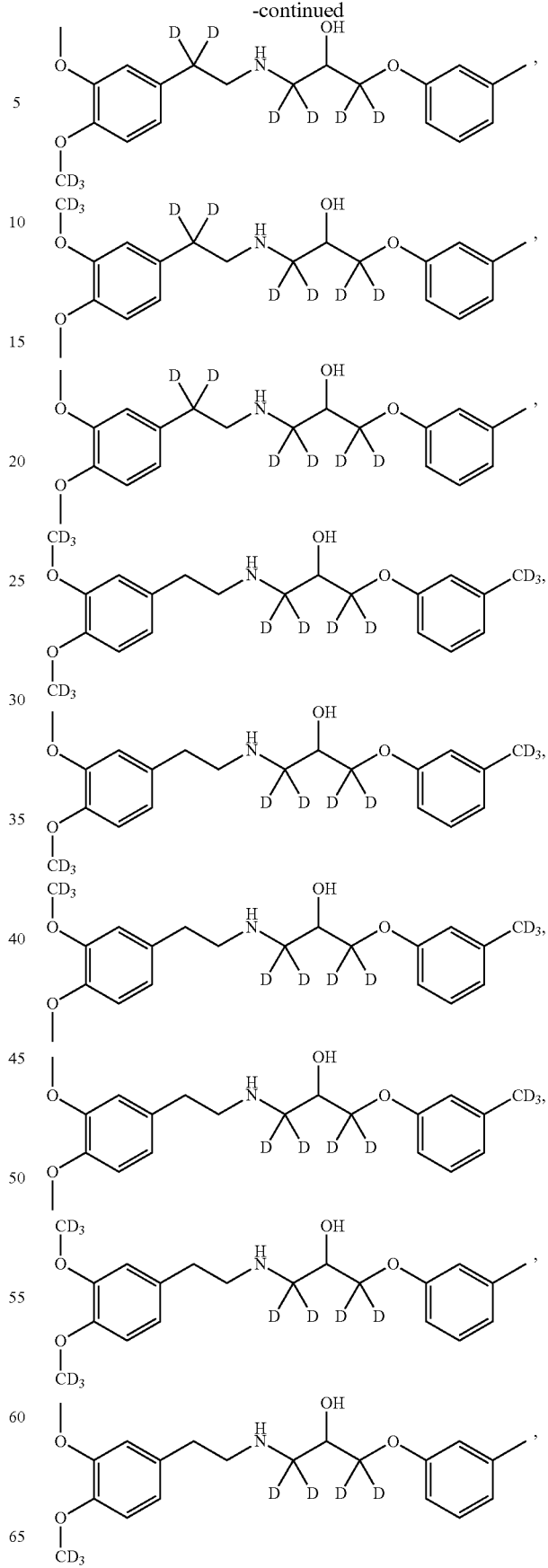

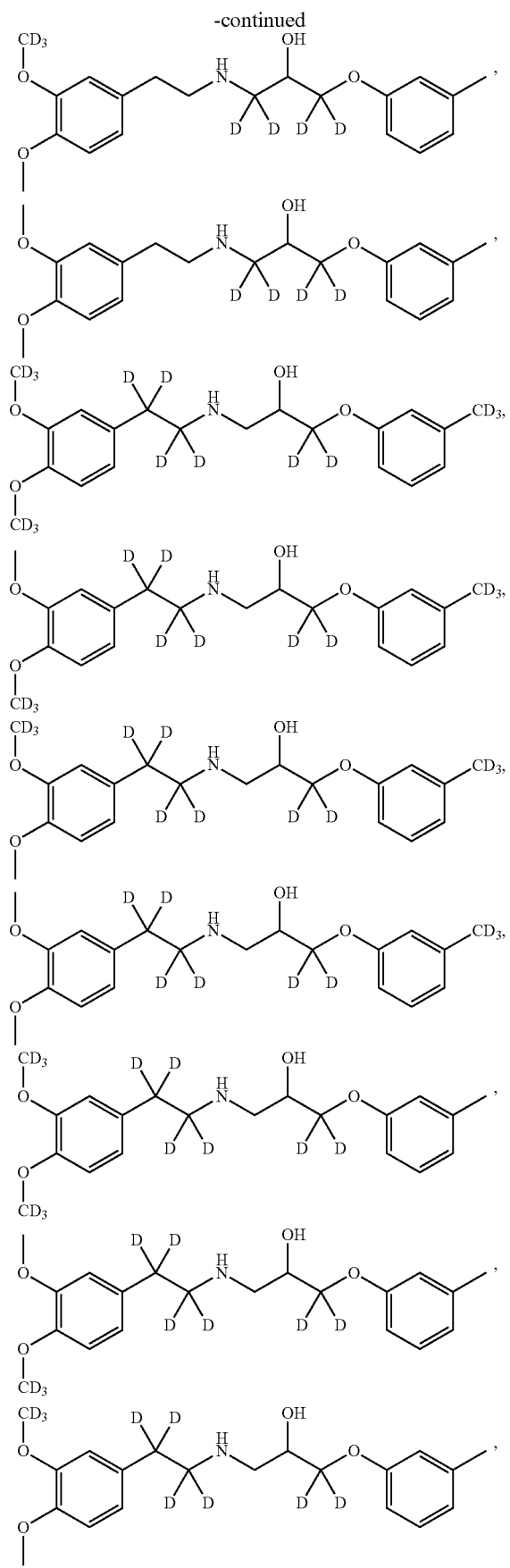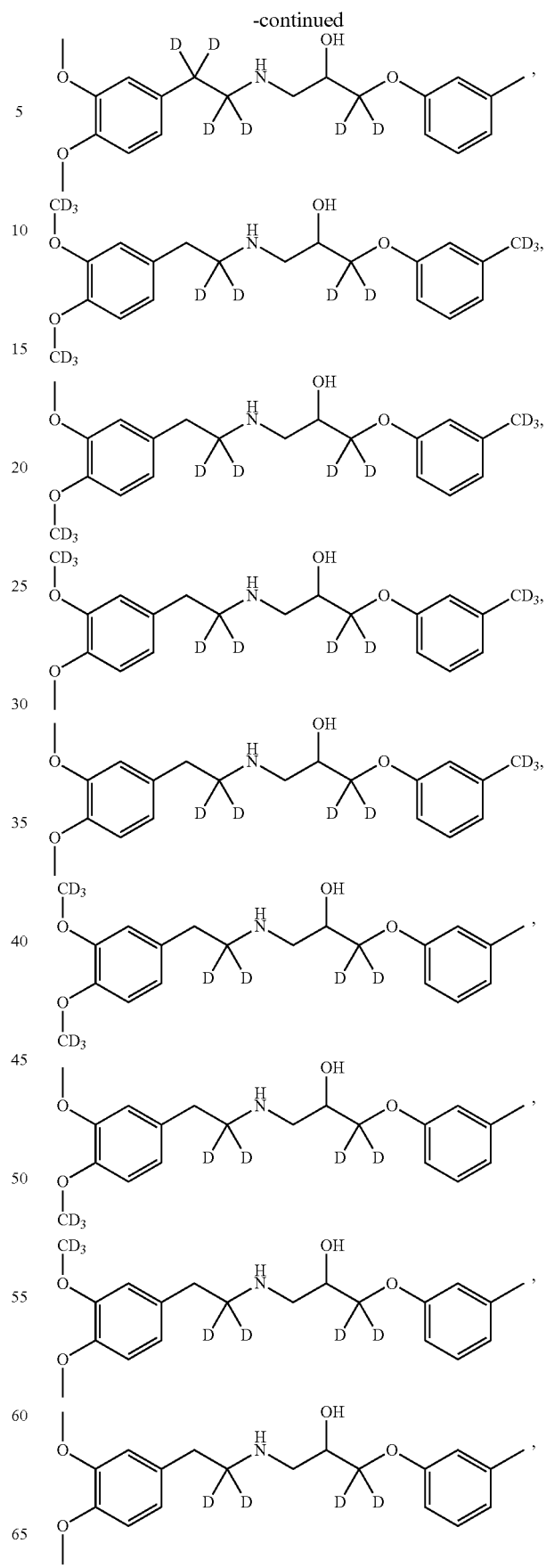

-continued
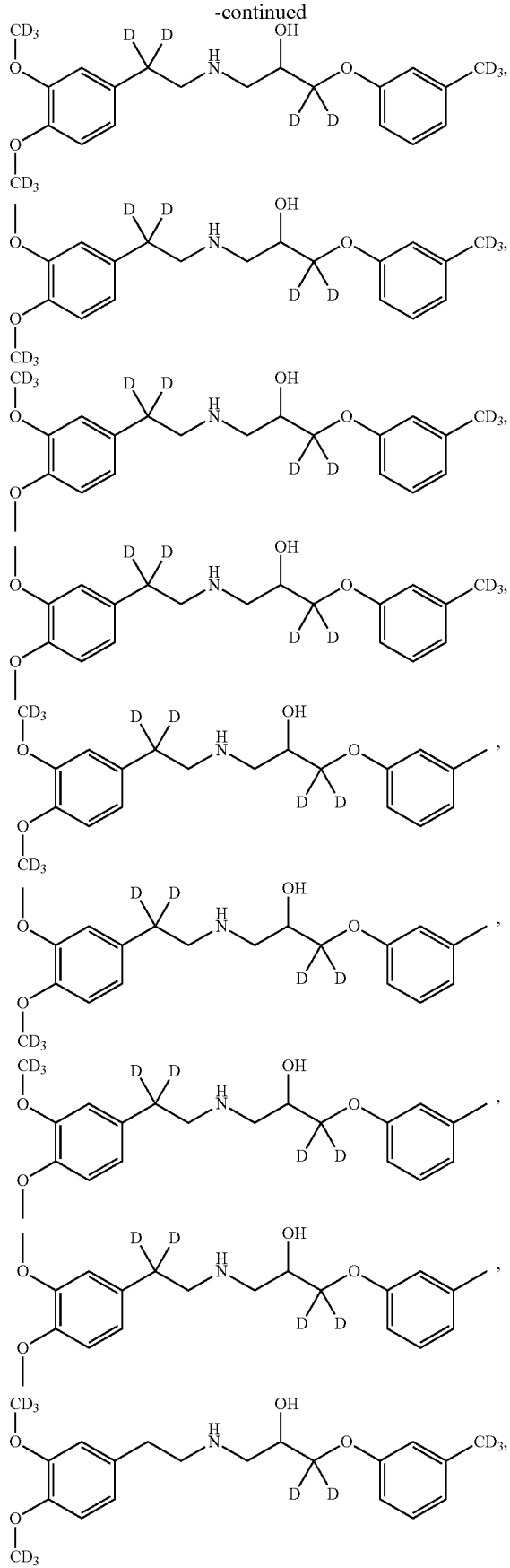
-continued
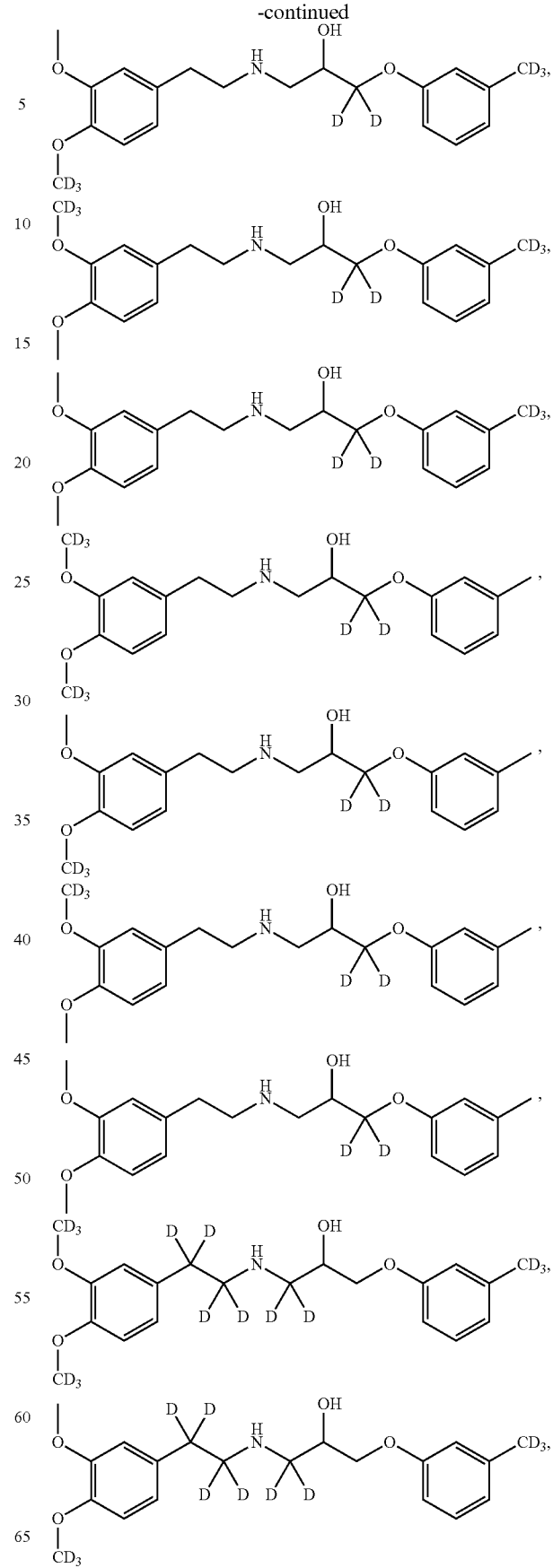

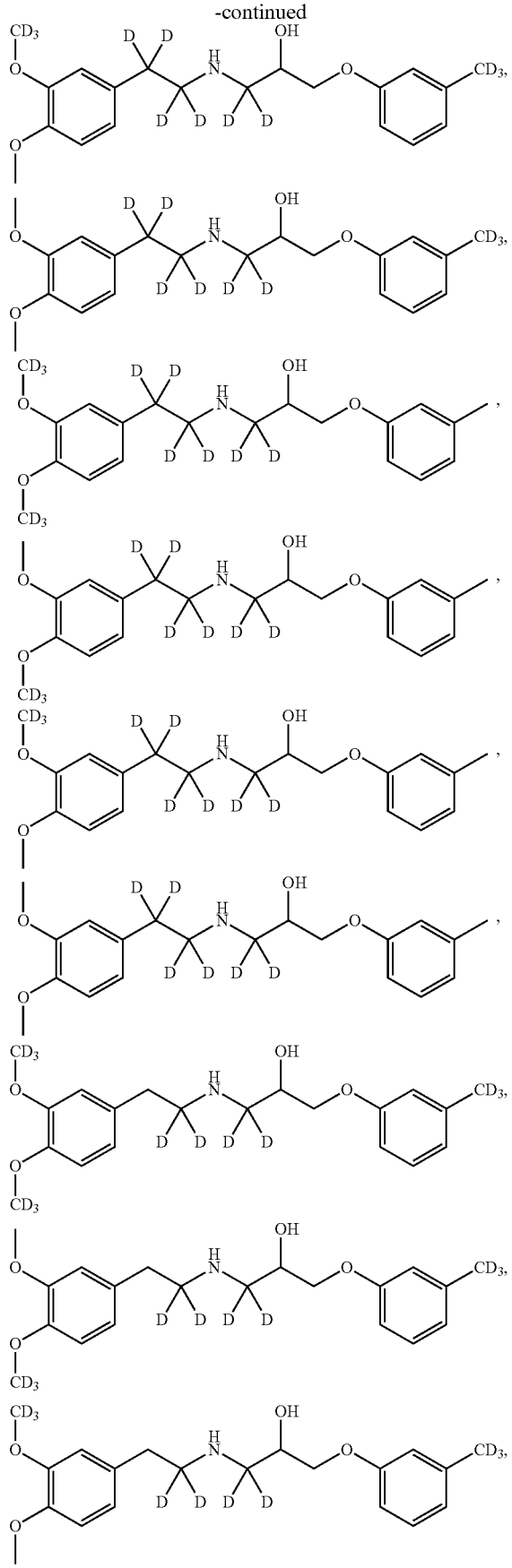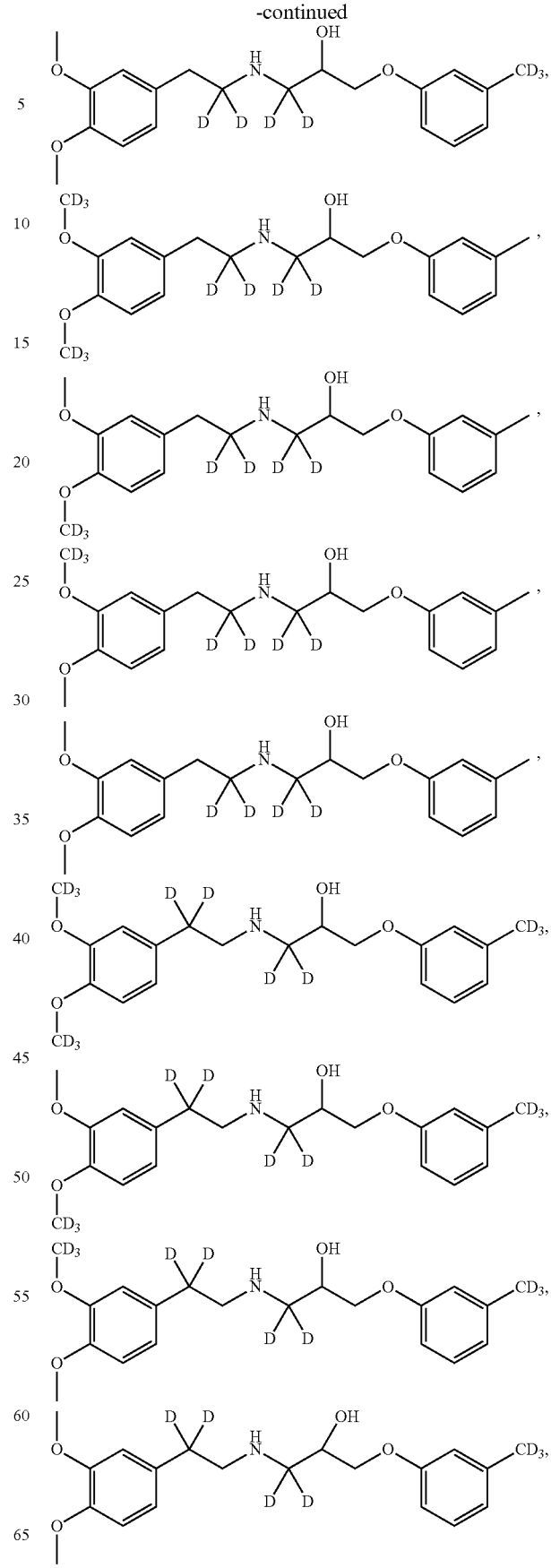

161
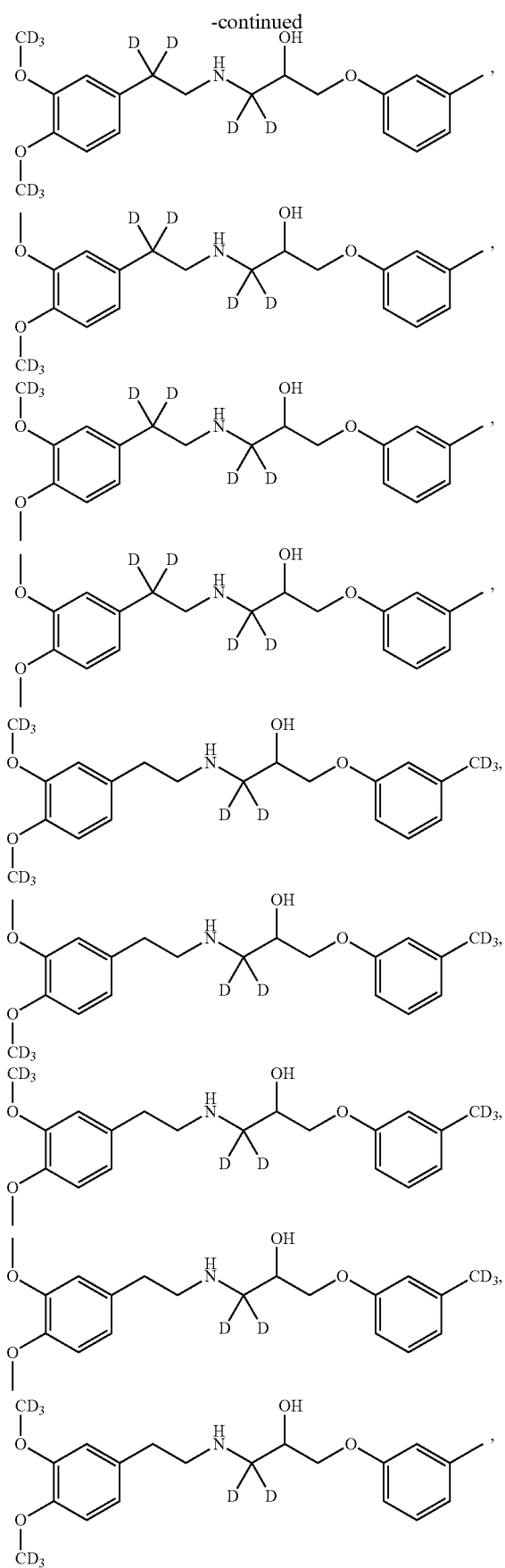
162
-continued
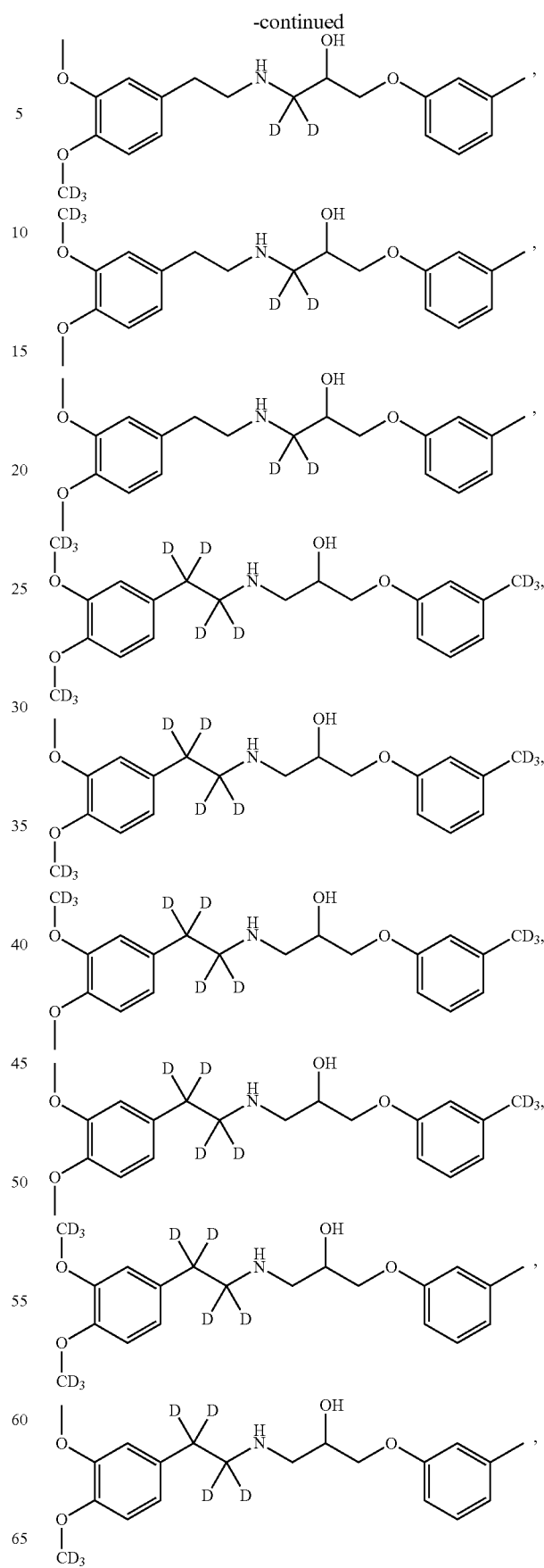

-continued

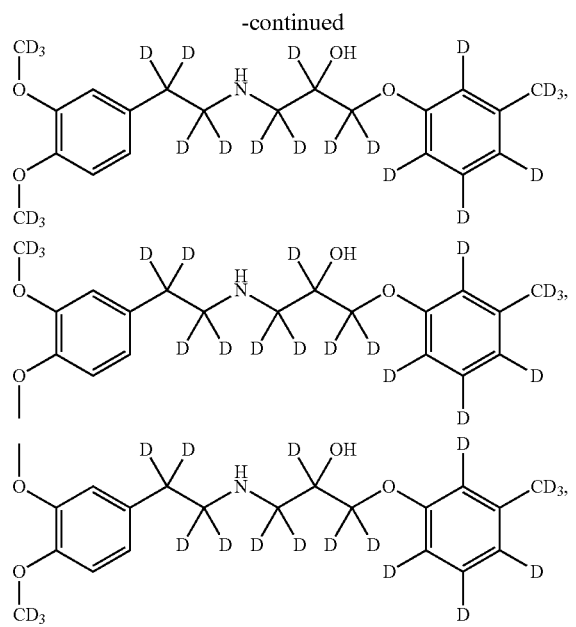
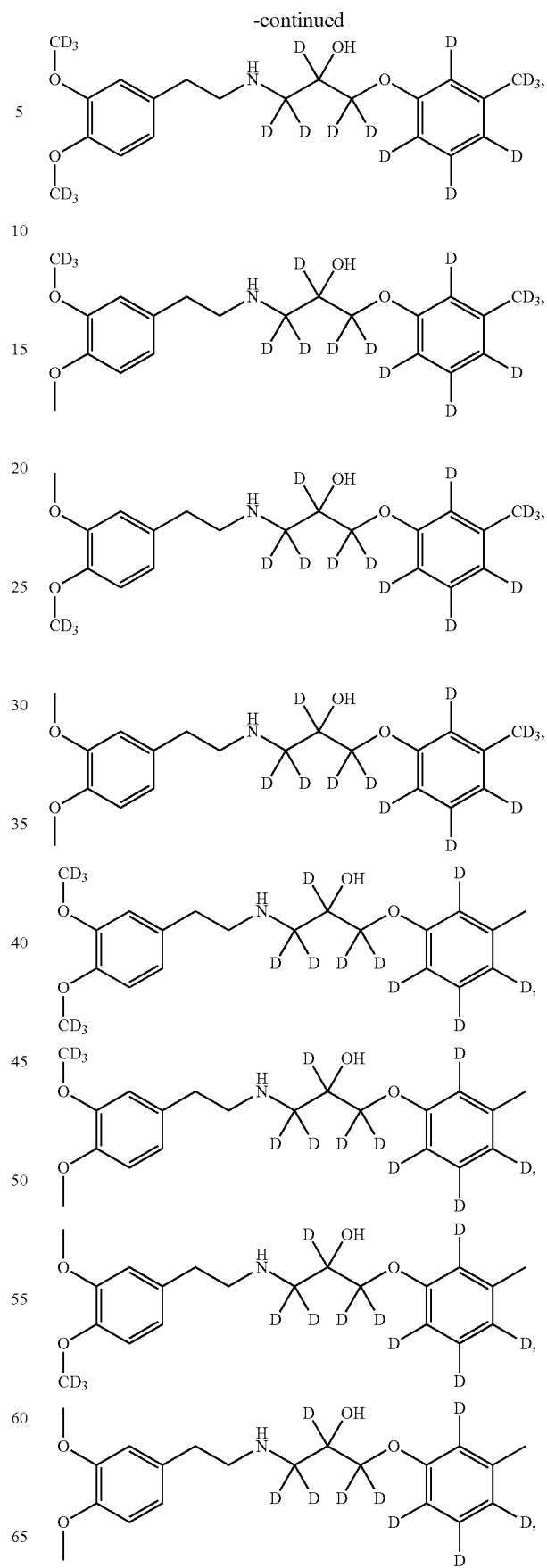

-continued

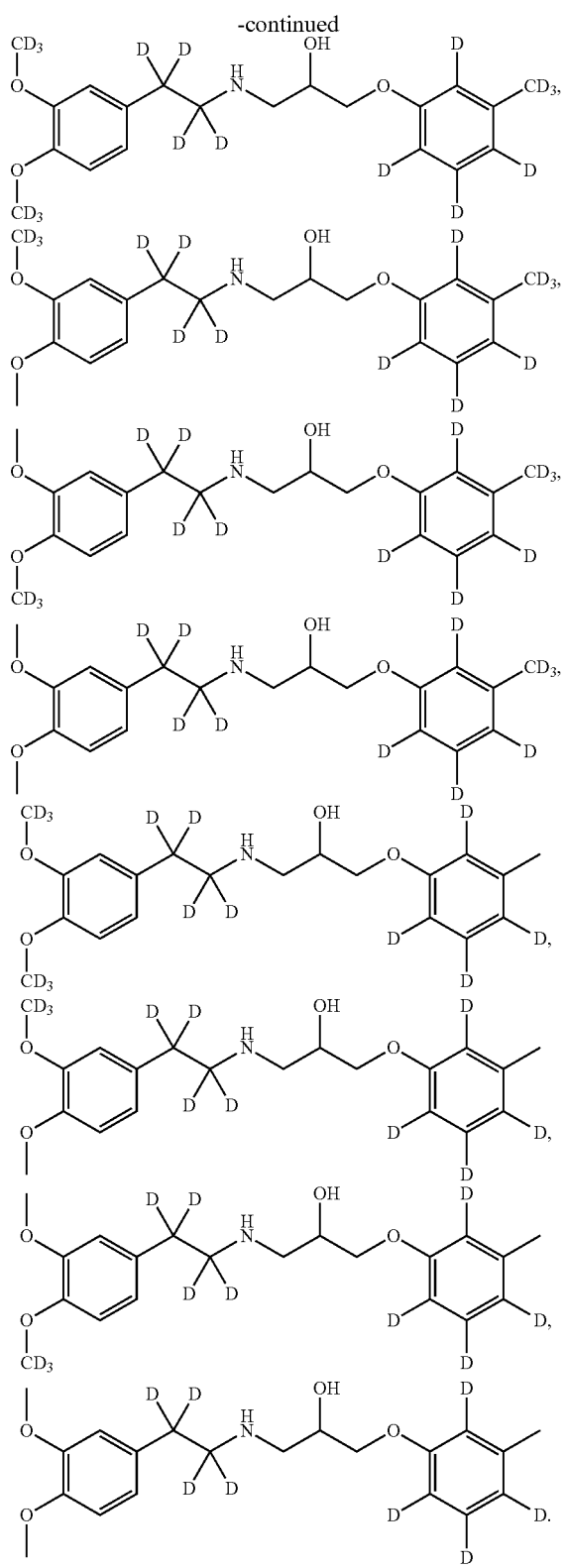

13. The compound as recited in claim 1, wherein each deuterium has deuterium enrichment of no less than about 50%.

14. The compound as recited in claim 1, wherein each deuterium has deuterium enrichment of no less than about 90%.

15. The compound as recited in claim 1, wherein each deuterium has deuterium enrichment of no less than about 98%.

16. A pharmaceutical composition comprising a compound as recited in claim 1 and a pharmaceutically acceptable carrier.

17. A method of treating a VMAT2-mediated disorder comprising the administering to a patient in need thereof a therapeutically effective amount of a compound as recited in claim 1.

18. The method as recited in claim 17, wherein the VMAT2-mediated disorder is a chronic hyperkinetic movement disorder, Tourette's syndrome, Parkinson's disease, Huntington's disease, Huntington's chorea, Sydenham's chorea, tardive dyskinesia/dystonia, Parkinson's disease levodopa-induced dyskinesia, levodopa-induced dyskinesia, ataxia, corticobasal degeneration, dyskinesia (paroxysmal), dystonia, essential tremor, hereditary spastic paraplegia, multiple system atrophy (Shy Drager Syndrome), myoclonus, progressive supranuclear palsy, restless legs syndrome, Rett Syndrome, spasticity due to stroke, cerebral palsy, multiple sclerosis, spinal cord or brain injury, tics, Wilson's Disease, oppositional defiant disorder, Huntington's disease like disease, benign hereditary chorea, neuroacanthocytosis, neurodegeneration with brain iron accumulation (NBIA), athetosis, Friedreich ataxia, spinocerebellar ataxia, multiple system atrophy, dentatorubral-pallidoluysian atrophy, ataxia with oculomotor apraxia, ataxia telangiectasia, dystonia-plus syndrome, Duchenne muscular dystrophy, or Down's syndrome.

19. The method as recited in claim 17 further comprising administering an additional therapeutic agent.

20. The method as recited in claim 19 wherein the additional therapeutic agent is a compound of Formula II:

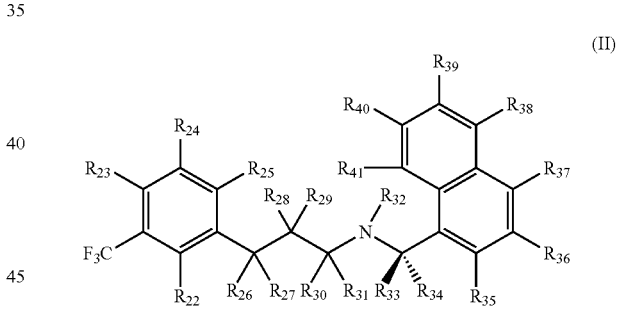

or a salt thereof, wherein:
$R_{22}$-$R_{32}$ and $R_{34}$-$R_{41}$ are independently hydrogen or deuterium;
$R_{33}$ is —$CH_3$, —$CH_2D$, —$CD_2H$, or —$CD_3$; and
at least one of $R_{22}$-$R_{41}$ is deuterium or contains deuterium.

21. The method as recited in claim 19 wherein the additional therapeutic agent is a compound of Formula III:

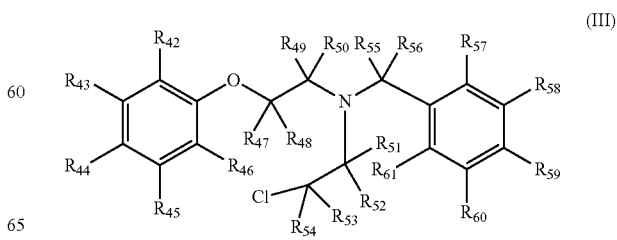

or a salt thereof, wherein:

$R_{42}$-$R_{49}$ and $R_{51}$-$R_{61}$ are independently hydrogen or deuterium;

$R_{50}$ is —CH$_3$, —CH$_2$D, —CD$_2$H, or —CD$_3$; and at least one of $R_{42}$-$R_{61}$ is deuterium or contains deuterium.

22. The method as recited in claim 19 wherein the additional therapeutic agent is tetrabenazine, dihydrotetrabenazine, a deuterated analog of tetrabenazine, or a deuterated analog of dihydrotetrabenazine.

23. The compound as recited in claim 1, wherein the compound is:

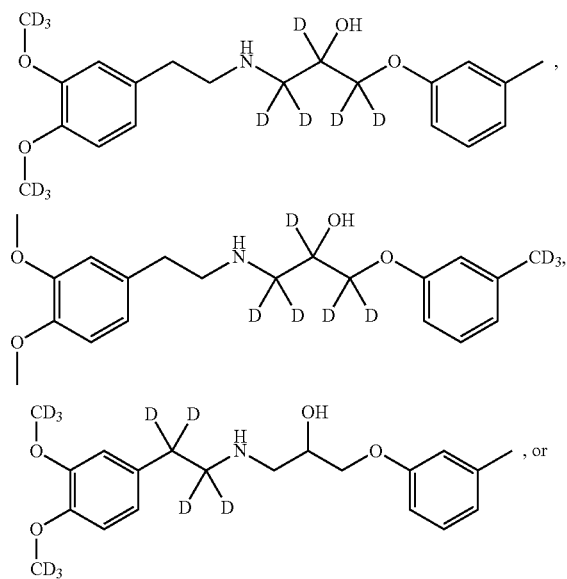

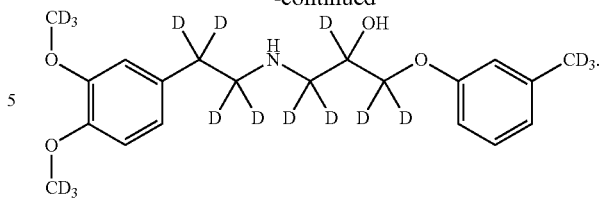

24. The method of claim 18, wherein:

the dystonia is a blepharospasm, spasmodic torticollis (cervical dystonia), writer's cramp (limb dystonia), laryngeal dystonia (spasmodic dysphonia), oromandibular dystonia, a focal dystonia, an idiopathic dystonia, or a secondary dystonia that is Oppenheim dystonia or torticollis; or the Huntington's disease like disease is HDL1, HDL2 or HDL3; or the ataxia with oculomotor apraxia is type 1 or 2.

25. A pharmaceutical composition comprising a compound as recited in claim 12 and a pharmaceutically acceptable carrier.

26. A pharmaceutical composition comprising a compound as recited in claim 14 and a pharmaceutically acceptable carrier.

27. A pharmaceutical composition comprising a compound as recited in claim 23 and a pharmaceutically acceptable carrier.

28. The compound as recited in claim 1, wherein each of $R_1$-$R_{21}$ that is deuterium has a deuterium enrichment of no less than about 50%.

29. The compound as recited in claim 1, wherein each of $R_1$-$R_{21}$ that is deuterium has a deuterium enrichment of no less than about 90%.

30. The compound as recited in claim 1, wherein each of $R_1$-$R_{21}$ that is deuterium has a deuterium enrichment of no less than about 98%.

* * * * *